United States Patent
Anryu et al.

(10) Patent No.: US 9,274,421 B2
(45) Date of Patent: Mar. 1, 2016

(54) SALT AND PHOTORESIST COMPOSITION COMPRISING THE SAME

(71) Applicant: SUMITOMO CHEMICAL COMPANY, LIMITED, Tokyo (JP)

(72) Inventors: Yukako Anryu, Osaka (JP); Koji Ichikawa, Osaka (JP); Masafumi Yoshida, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/519,939

(22) Filed: Oct. 21, 2014

(65) Prior Publication Data

US 2015/0118620 A1 Apr. 30, 2015

(30) Foreign Application Priority Data

Oct. 24, 2013 (JP) ................. 2013-220862

(51) Int. Cl.
*C07C 381/12* (2006.01)
*G03F 7/004* (2006.01)
*G03F 7/039* (2006.01)
*G03F 7/20* (2006.01)

(52) U.S. Cl.
CPC ............ *G03F 7/0045* (2013.01); *C07C 381/12* (2013.01); *G03F 7/0046* (2013.01); *G03F 7/0397* (2013.01); *G03F 7/2041* (2013.01)

(58) Field of Classification Search
CPC ..... C07C 381/12; G03F 7/004; G03F 7/0045; G03F 7/0046; G03F 7/027; G03F 7/038; G03F 7/039; G03F 7/0392; G03F 7/0397; G03F 7/20
See application file for complete search history.

(56) References Cited

U.S. PATENT DOCUMENTS

| 2005/0064333 A1* | 3/2005 | Crivello ............... 430/270.1 |
| 2008/0193874 A1 | 8/2008 | Takata et al. |
| 2009/0023095 A1 | 1/2009 | Hada et al. |
| 2009/0131684 A1* | 5/2009 | Kang et al. ................ 549/20 |
| 2010/0151380 A1 | 6/2010 | Ando et al. |
| 2010/0203446 A1 | 8/2010 | Ichikawa et al. |
| 2012/0088190 A1 | 4/2012 | Ichikawa et al. |
| 2012/0122032 A1 | 5/2012 | Anryu et al. |
| 2012/0172606 A1* | 7/2012 | Joo et al. ................... 549/78 |
| 2012/0270153 A1 | 10/2012 | Ichikawa et al. |
| 2013/0017501 A1 | 1/2013 | Nakamura et al. |
| 2013/0143157 A1 | 6/2013 | Tanaka et al. |

FOREIGN PATENT DOCUMENTS

| JP | 2000-122294 A | 4/2000 |
| JP | 2003-342254 A | 12/2003 |
| JP | 2007-57670 A | 3/2007 |
| JP | 2008-209917 A | 9/2008 |
| JP | 2010-61018 A | 3/2010 |
| JP | 2010-204634 A | 9/2010 |
| JP | 2010-204646 A | 9/2010 |
| JP | 2012-41274 A | 3/2012 |
| JP | 2013-3155 A | 1/2013 |
| JP | 2013-11905 A | 1/2013 |
| JP | 2013-68914 A | 4/2013 |
| WO | WO 2014/034533 A1 | 3/2014 |

OTHER PUBLICATIONS

United States Office Action, dated Aug. 11, 2015, for U.S. Appl. No. 14/519,915.

* cited by examiner

*Primary Examiner* — Anca Eoff
(74) *Attorney, Agent, or Firm* — Birch, Stewart, Kolasch & Birch, LLP

(57) ABSTRACT

A salt represented by formula (I):

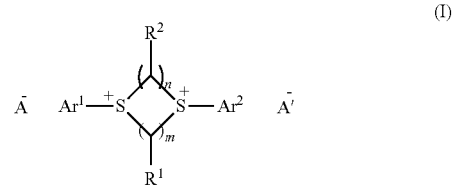

wherein $R^1$ and $R^2$ independently in each occurrence represent a hydrogen atom, a hydroxy group or a C1-C12 hydrocarbon group where a methylene group can be replaced by an oxygen atom or a carbonyl group;
$Ar^1$ and $Ar^2$ each independently represent a C6-C36 aromatic hydrocarbon group which can have a substituent or a C6-C36 heteroaromatic hydrocarbon group which can have a substituent;
$A^-$ and $A'^-$ each independently represent an organic anion; and
"m" and "n" independently each represent an integer of 1 to 2.

5 Claims, No Drawings

SALT AND PHOTORESIST COMPOSITION COMPRISING THE SAME

This nonprovisional application claims priority under 35 U.S.C. §119(a) on Patent Application No. 2013-220862 filed in JAPAN on Oct. 24, 2013, the entire contents of which are hereby incorporated by reference.

FIELD OF THE INVENTION

The present invention relates to a salt and a photoresist composition comprising the same.

BACKGROUND OF THE INVENTION

A photoresist composition is used for semiconductor microfabrication employing a lithography process.

JP2003-342254A1 discloses a photoresist composition comprising a salt represented by the following formula:

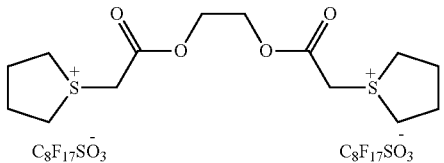

as an acid generator.

SUMMARY OF THE INVENTION

The present invention relates to provide a salt for suitable for an acid generator and a photoresist composition comprising the same.

The present invention relates to the followings:

[1] A salt represented by formula (I):

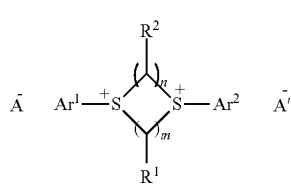

wherein $R^1$ and $R^2$ independently in each occurrence represent a hydrogen atom, a hydroxy group or a C1-C12 hydrocarbon group where a methylene group can be replaced by an oxygen atom or a carbonyl group;
$Ar^1$ and $Ar^2$ each independently represent a C6-C36 aromatic hydrocarbon group which can have a substituent or a C6-C36 heteroaromatic hydrocarbon group which can have a substituent;
$A^-$ and $A'^-$ each independently represent an organic anion; and
"m" and "n" independently each represent an integer of 1 to 2.

[2] The salt according to [1] where at least one of $A^-$ and $A'^-$ is an anion represented by formula

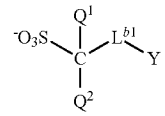

wherein $Q^1$ and $Q^2$ independently each represent a fluorine atom or a C1-C6 perfluoroalkyl group;
$L^{b1}$ represents a C1-C24 divalent saturated hydrocarbon group where a methylene group can be replaced by an oxygen atom or a carbonyl group and where a hydrogen atom can be replaced by a fluorine atom or a hydroxyl group; and
Y represents a methyl group or a C3-C18 alicyclic hydrocarbon group where a methylene group can be replaced by an oxygen atom, a carbonyl group or a sulfonyl group and where a hydrogen atom can be replaced by a substituent.

[3] An acid generator which comprises the salt according to [1] or [2].

[4] A photoresist composition which comprises the salt according to [1] or [2] and a resin having an acid-labile group.

[5] A process for producing a photoresist pattern comprising the following steps (1) to (5):
(1) a step of applying the photoresist composition according to [4] on a substrate,
(2) a step of forming a composition film by conducting drying,
(3) a step of exposing the composition film to radiation,
(4) a step of baking the exposed composition film, and
(5) a step of developing the baked composition film.

Hereinafter, the salt represented by formula (I) is sometimes ref erred to as "Salt (I)" and the cation in formula (I) is sometimes referred to as "Cation (I)".

DESCRIPTION OF PREFERRED EMBODIMENTS

<Salt (I)>
The Salt (I) is represented by formula (I).

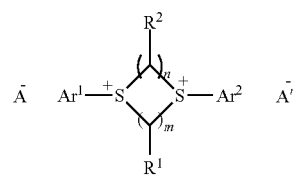

In formula (I), $R^1$ and $R^2$ independently in each occurrence represent a hydrogen atom, a hydroxy group or a C1-C12 hydrocarbon group where a methylene group can be replaced by an oxygen atom or a carbonyl group.

When the compound of formula (I) has two $R^1$s, each of $R^1$ may be the same or different from the other. When the compound has two $R^2$s, each of $R^2$ may be the same or different from the other. Examples of the hydrocarbon group represented by $R^1$ and $R^2$ include a C1-C12 alkyl group, a C3-C12 alicyclic hydrocarbon group, a C6-C12 aromatic hydrocarbon group and a group formed by combining two or more of them.

The alkyl group may be a linear or branched one, examples of which include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group, a nonyl group, an undecyl group and a decyl group. The alicyclic hydrocarbon group may be a monocyclic or polycyclic one, which includes those consisting of an alkyl group and a cycloalkyl group.

Examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group, a cycloheptyl group, a cyclodecyl group, a methylcyclohexyl group and a dimethylcyclohexyl group; and Examples of the polycyclic alicyclic hydrocarbon group include a hydronaphthyl group, an adamantyl group, a norbornyl group, an isobornyl group, 2-alkyladamantane-2-yl group, 1-(adamantane-1-yl)alkane-1-yl group, a methylnorbornyl group.

Examples of the aromatic hydrocarbon groups include a phenyl group, and a naphthyl group.

Examples of the group formed by combining two or more of them include aralkyl groups such as a benzyl group, and a phenethyl group.

Examples of the hydrocarbon group where a methylene group has been replaced by an oxygen atom or a carbonyl group include a C1-C12 alkoxy group such as a methoxy group, an ethoxy group, a butoxy group; a C2-C12 alkylcarbonyl group such as an acetyl group; a C2-C12 alkoxycarbonyl group such as a methoxycarbonyl group; a C2-C12 alkylcarbonyloxy group such as an acetyloxy group, butoxycarbonyloxy group; and a C7-C12 benzyloxy group such as a benzoyloxy group.

$R^1$ preferably represent a hydrogen atom.

$R^2$ preferably represent a hydrogen atom.

Preferably one or both of $R^1$ and $R^2$ represent a hydrogen atom, and more preferably both of them represent a hydrogen atom.

$Ar^1$ and $Ar^2$ each independently represent a C6-C36 aromatic hydrocarbon group which can have a substituent, or a C6-C36 heteroaromatic hydrocarbon group which can have a substituent.

Each of the aromatic hydrocarbon group and heteroaromatic hydrocarbon group has preferably 6 to 24 carbon atoms and more preferably 6 to 18 carbon atoms.

Examples of the aromatic hydrocarbon groups include a C6-C36 aryl group such as a phenyl group, a naphthyl group, an anthracenyl group, a phenanthryl group, a tolyl group, a xylyl group, a cumyl group, a dimethylphenyl group, a trimethylphenyl group, an ethylphenyl group, a propylphenyl group, a butylphenyl group, a biphenyl group, an triphenyl group, an indenyl group, a tetrahydronaphthyl group, p-adamantylphenyl group, a phenanthryl group, a 2,6-diethylphenyl group, 2-methyl-6-ethylphenyl group. Examples of the heteroatoms in the heteroaromatic hydrocarbon group include a nitrogen atom, an oxygen atom, and a sulfur atom.

Examples of the heteroaromatic hydrocarbon groups include a furyl group, and a thiophenyl group.

Examples of substituents in the aromatic or heteroaromatic hydrocarbon group include a hydroxy group, a C1-C12 alkoxy group, a C2-C18 alkylcarbonyloxy group, a C7-C18 arylcarbonyloxy group and a C2-C18 alkoxycarbonyloxy group. In the C1-C12 alkoxy group, a methylene group not attached to its oxygen atom can be replaced by an oxygen atom. The substituent is preferably a hydroxy group.

Examples of the alkoxy groups include a methoxy group, an ethoxy group, a propoxy group, a butoxy group, a pentyloxy group, a hexyloxy group, a heptyloxy group, an octyloxy group, a decyloxy group and a dodecyloxy group, preferably a C1-C6 alkoxy group, more preferably a methoxy group.

Examples of the alkylcarbonyloxy group include a methylcarbonyloxy group, an ethylcarbonyloxy group, a n-propylcarbonyloxy group, an isopropylcarbonyloxy group, a n-butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group, preferably a C2-C12 alkylcarbonyloxy group, and more preferably a methylcarbonyloxy group.

Examples of the arylcarbonyloxy group include a phenylcarbonyloxy group, a tosylcarbonyloxy group, C7-C12 arylcarbonyloxy group and more preferably phenylcarbonyloxy group.

Examples of the alkoxycarbonyloxy group include a methoxycarbonyloxy group, an ethoxycarbonyloxy group, a n-propoxycarbonyloxy group, an isopropoxycarbonyloxy group, a n-butoxycarbonyloxy group, a sec-butoxycarbonyloxy group, a tert-butoxycarbonyloxy group, a pentyloxycarbonyloxy group, a hexyloxycarbonyloxy group, a octyloxycarbonyloxy group and a 2-ethyl hexyloxycarbonyloxy group, preferably a C2-C8 oxycarbonyloxy group, more preferably tert-butyloxycarbonyloxy group.

Preferably, at least one of $Ar^1$ and $Ar^2$ is a C6-C36 aromatic hydrocarbon group which can have a substituent. More preferably, both of $Ar^1$ and $Ar^2$ is a C6-C36 aromatic hydrocarbon group which can have a substituent.

$Ar^1$ and $Ar^2$ are preferably the same group, more preferably C6-C24 aromatic hydrocarbon group which can have a substituent, and still more preferably a phenyl or naphtyl group which can have a substituent. "n" is preferably 2. "m" is preferably 2.

Preferably at least one of "n" and "m" is 2, and more preferably both of them is 2.

Examples of Cation (I) include the following ones.

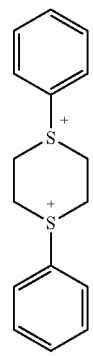

(I-c-1)

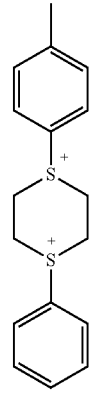

(I-c-2)

(I-c-3)
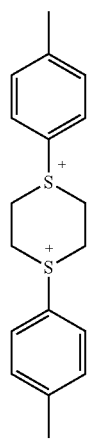
(I-c-4)
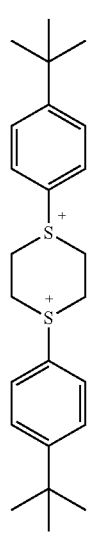
(I-c-5)
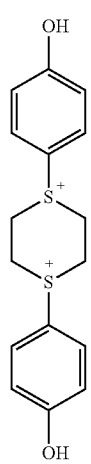
(I-c-6)
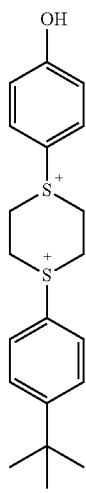
(I-c-7)
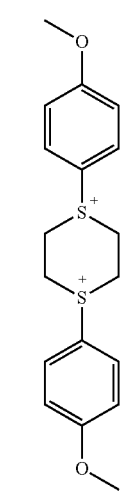
(I-c-8)
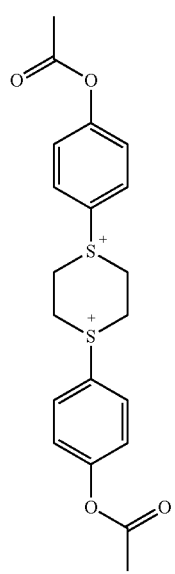

(I-c-9)
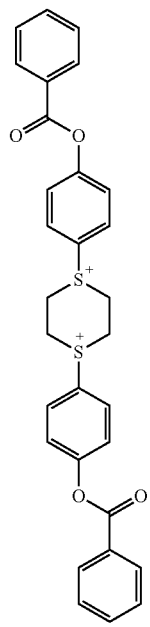
(I-c-10)
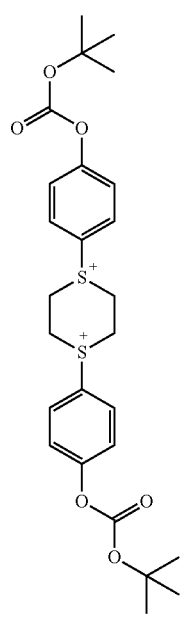
(I-c-11)
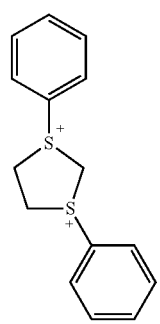
(I-c-12)
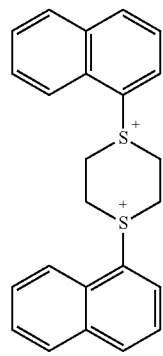
(I-c-13)
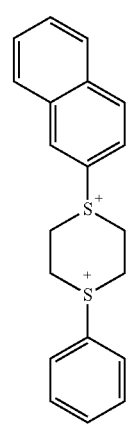
(I-c-14)
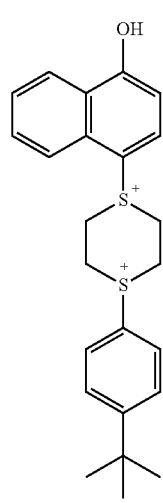

(I-c-15)
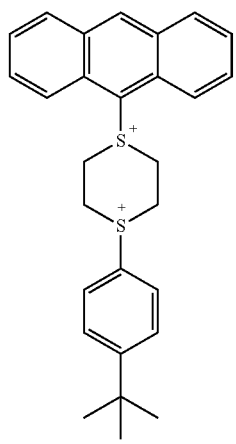
(I-c-16)
(I-c-17)
(I-c-18)
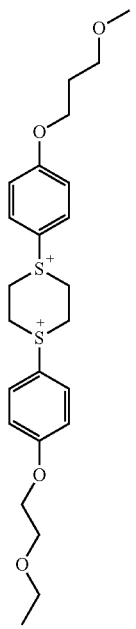
(I-c-19)
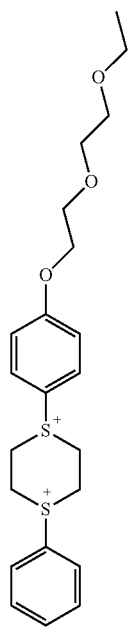

(I-c-20)

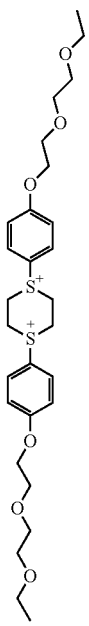

(I-c-21)

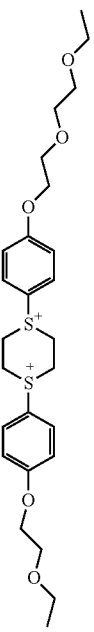

(I-c-22)

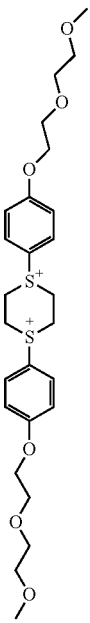

Among them, the cations represented by formulae (I-c-1), (I-c-3), (I-c-4), (I-c-7), (I-c-12), (I-c-14), (I-c-16), (I-c-21) and (I-c-22) are preferred, and the cations represented by formulae (I-c-1), (I-c-3), (I-c-4), (I-c-7), (I-c-12), (I-c-14) and (I-c-16) are more preferred.

In formula (I), $A^-$ and $A'^-$ each independently represent an organic anion.

$A^-$ and $A'^-$ may be the same or different from each other. $A^-$ and $A'^-$ are preferably the same group.

Examples of the organic anion include sulfonic acid anions, sulfonylimide anions, sulfonylmethide anions and carboxylic acid anions.

At least one of $A^-$ and $A'^-$ is preferably a sulfonic acid anion, more preferably represented by formula (I-A):

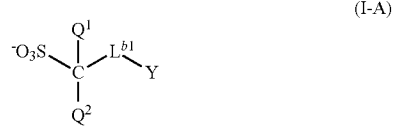

(I-A)

wherein $Q^1$ and $Q^2$ independently each represent a fluorine atom or a C1-C6 perfluoroalkyl group, $L^{b1}$ represents a C1-C24 divalent saturated hydrocarbon group where a methylene group can be replaced by an oxygen atom or a carbonyl group and where a hydrogen atom can be replaced by a fluorine atom or a hydroxyl group; and Y represents a methyl group or a C3-C18 alicyclic hydrocarbon group where a methylene group can be replaced by an oxygen atom, a carbonyl group or a sulfonyl group and where a hydrogen atom can be replaced by a substituent.

Examples of the C1-C6 perfluoroalkyl group represented by $Q^1$ and $Q^2$ include a trifluoromethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group.

$Q^1$ and $Q^2$ independently each represent preferably a fluorine atom or a trifluoromethyl group, more preferably a fluorine atom.

Examples of the divalent saturated hydrocarbon group include a linear alkanediyl groups, branched alkanediyl groups, monocyclic or polycyclic alicyclic saturated hydrocarbon groups, and a group formed by combining two or more of them.

Specific examples of the divalent saturated hydrocarbon group include linear alkanediyl groups such as a methyl group, an ethylene group, a propane-1,3-diyl group, a butane-1,4-diyl group, a pentane-1,5-diyl group, a hexane-1,6-diyl group, a heptane-1,7-diyl group, a octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl groups; branched alkanediyl groups such as an ethane-1,1-diyl group, a propane-1,1-diyl group, a propane-1,2-diyl group, a propane-2,2-diyl group, a pentane-2,4-diyl group, a 2-methyl propane-1,3-diyl group, a 2-methyl propane-1,2-diyl group, a pentane-1,4-diyl group, and a 2-methyl butane-1,4-diyl group; divalent monocyclic alicyclic saturation hydrocarbon group including cycloalkanediyl groups such as a cyclobutane-1,3-diyl group, a cyclopentane-1,3-diyl group, a cyclohexane-1,4-diyl group, and a cyclooctane-1,5-diyl group; and divalent polycyclic saturated hydrocarbon groups such as a norbornane-1,4-diyl group, a norbornane-2,5-diyl group, an adamantane-1,5-diyl group, an adamantane-2,6-diyl group.

Specific examples of the divalent saturated hydrocarbon group where a methylene group has been replaced by an oxygen atom or a carbonyl group include those represented by formulae (b1-1), (b1-2) and (b1-3).

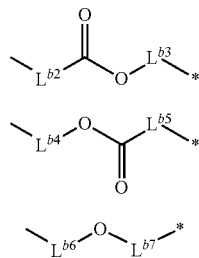

In these formulae, * represents a binding site to Y.
In formula (b1-1), $L^{b2}$ represents a single bond or a C1-C22 divalent saturated hydrocarbon group where a hydrogen atom can be replaced by a fluorine atom;
$L^{b3}$ represents a single bond or a C1-C22 divalent saturated hydrocarbon group where a hydrogen atom may be replaced by a fluorine atom or a hydroxy group, and where a methylene group can be replaced by —O— or —CO—; provided that total carbon atoms in $L^{b2}$ and $L^{b3}$ are 22 or less.
In formula (b1-2), $L^{b4}$ represents a single bond or a C1-C22 divalent saturated hydrocarbon group where a hydrogen atom can be replaced by a fluorine atom;
$L^{b5}$ represents a single bond or a C1-C22 divalent saturated hydrocarbon group where a hydrogen atom may be replaced by a fluorine atom or a hydroxy group, and where a methylene group can be replaced by —O— or —CO—; provided that total carbon atoms in $L^{b4}$ and $L^{b5}$ are 22 or less.
In formula (b1-3), $L^{b6}$ represents a single bond or a C1-C23 divalent saturated hydrocarbon group where a hydrogen atom can be replaced by a fluorine atom or a hydroxy group;
$L^{b7}$ represents a single bond or a C1-C23 divalent saturated hydrocarbon group where a hydrogen atom may be replaced by a fluorine atom or a hydroxy group, and where a methylene group can be replaced by —O— or —CO—; provided that total carbon atoms in $L^{b6}$ and $L^{b7}$ are 23 or less.

In formulae (b1-1) to (b1-3), the number of the carbon atoms in the divalent saturated hydrocarbon groups include that of the carbon atoms in the methylene groups which have been replaced by an oxygen atom or a carbonyl group.

Specific examples of the divalent saturated hydrocarbon groups for $L^{b2}$, $L^{b3}$, $L^{b4}$, $L^{b5}$, $L^{b6}$ and $L^{b7}$ include the same as referred to for $L^{b1}$.
$L^{b2}$ is preferably a single bond.
$L^{b3}$ is preferably a C1-C4 alkanediyl group.
$L^{b4}$ is preferably a C1-C8 divalent saturated hydrocarbon group where a hydrogen atom may be replaced by a fluorine atom.
$L^{b5}$ is preferably a single bond or a C1-C8 divalent saturated hydrocarbon group.
$L^{b6}$ is preferably a single bond or a C1-C4 divalent saturated hydrocarbon group where a hydrogen atom can be replaced by a fluorine atom.
$L^{b7}$ is preferably a single bond or a C1-C18 divalent saturated hydrocarbon group where a hydrogen atom can be replaced by a fluorine atom or a hydroxy group, and where a methylene group can be replaced by —O— or —CO—.

As $L^{b1}$, the divalent saturated hydrocarbon group where a methylene group has been replaced by —O— or —CO— is preferably one represented by formula (b1-1) or (b1-3).
Examples of one represented by formula (b1-1) include those represented by formulae (b1-4) to (b1-8).

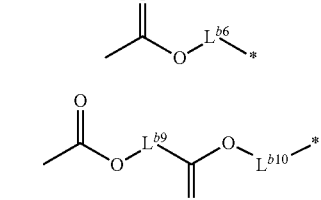

In these formulae, * represents a binding site to Y.
In formula (b1-4), $L^{b8}$ represents a single bond or a C1-C22 divalent saturated hydrocarbon group where a hydrogen atom can be replaced by a fluorine atom or a hydroxy group.
In formula (b1-5), $L^{b9}$ represents a C1-C20 divalent saturated hydrocarbon group and $L^{b10}$ represents a single bond or a C1-C19 divalent saturated hydrocarbon group where a hydrogen atom can be replaced by a fluorine atom or a hydroxy group, provided that total carbon atoms in $L^{b9}$ and $L^{b10}$ are 20 or less.

In formula (b1-6), $L^{b11}$ represents a C1-C21 divalent saturated hydrocarbon group and $L^{b12}$ represents a single bond or a C1-C20 divalent saturated hydrocarbon group where a hydrogen atom can be replaced by a fluorine atom or a hydroxy group, provided that total carbon atoms in $L^{b11}$ and $L^{b12}$ are 21 or less.

In formula (b1-7), $L^{b13}$ represents a C1-C19 divalent saturated hydrocarbon group, $L^{b14}$ represents a single bond or a C1-C18 divalent saturated hydrocarbon group and $L^{b15}$ represents a single bond or a C1-C18 divalent saturated hydrocarbon group where a hydrogen atom can be replaced by a fluorine atom or a hydroxy group, provided that total carbon atoms in $L^{b13}$, $L^{b14}$ and $L^{b15}$ are 19 or less.

In formula (b1-8), $L^{b16}$ represents a C1-C18 divalent saturated hydrocarbon group, $L^{b1}$ represents a C1-C18 divalent saturated hydrocarbon group and $L^{b18}$ represents a single bond or a C1-C17 divalent saturated hydrocarbon group where a hydrogen atom can be replaced by a fluorine atom or a hydroxy group, provided that total carbon atoms in $L^{b16}$, $L^{b17}$ and $L^{b18}$ are 19 or less.

$L^{b8}$ is preferably a C1-C4 alkanediyl group.

$L^{b9}$ is preferably a C1-C8 divalent saturated hydrocarbon group.

$L^{b10}$ is preferably a single bond or a C1-C19 divalent saturated hydrocarbon group, more preferably a single bond or a C1-C8 divalent saturated hydrocarbon group.

$L^{b11}$ is preferably a C1-C8 divalent saturated hydrocarbon group $L^{b12}$ is preferably a single bond or a C1-C8 divalent saturated hydrocarbon group.

$L^{b13}$ is preferably a C1-C12 divalent saturated hydrocarbon group.

$L^{b14}$ is preferably a single bond or a C1-C6 divalent saturated hydrocarbon group.

$L^{b15}$ is preferably a single bond or a C1-C18 divalent saturated hydrocarbon group, more preferably a single bond or a C1-C8 divalent saturated hydrocarbon group.

$L^{b16}$ is preferably a C1-C12 divalent saturated hydrocarbon group.

$L^{b17}$ is preferably a C1-C6 divalent saturated hydrocarbon group.

$L^{b18}$ is preferably a single bond or a C1-C17 divalent saturated hydrocarbon group, more preferably a single bond or a C1-C4 divalent saturated hydrocarbon group.

Examples of the group represented by formula (b1-4) include the following ones.

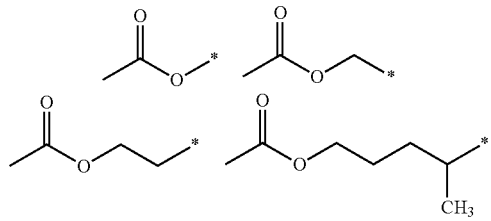

In each formula, * represents a binding site to Y.

Examples of the group represented by formula (b1-5) include the following ones.

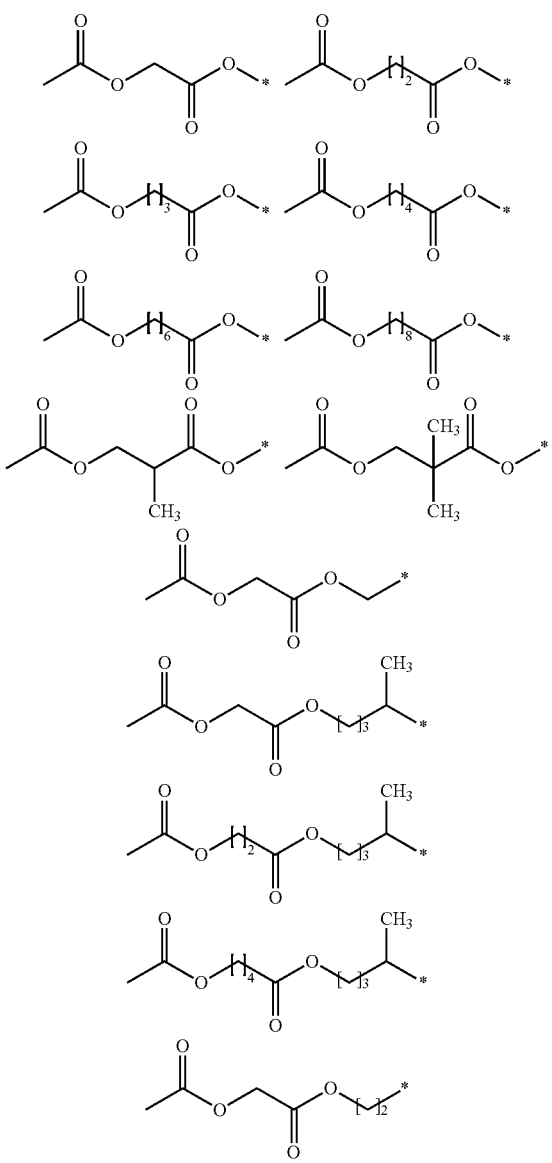

In each formula, * represents a binding site to Y.

Examples of the group represented by formula (b1-6) include the following ones.

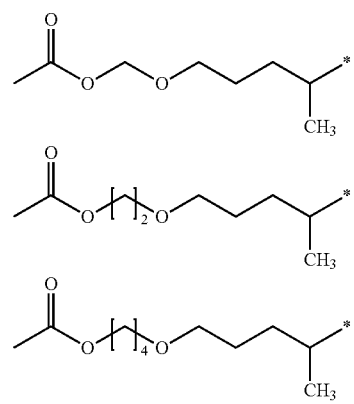

-continued

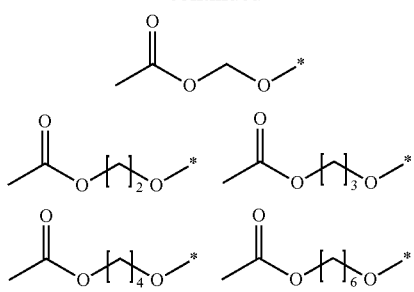

In each formula, * represents a binding site to Y.

Examples of the group represented by formula (b1-7) include the following ones.

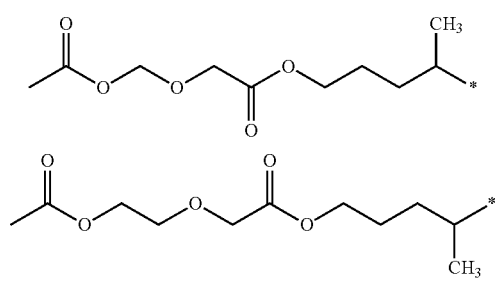

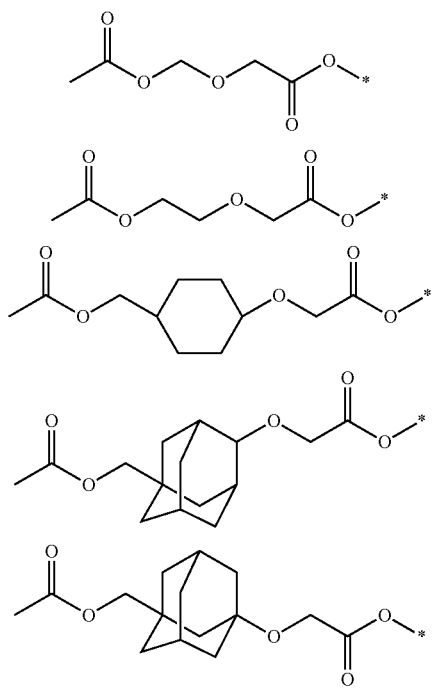

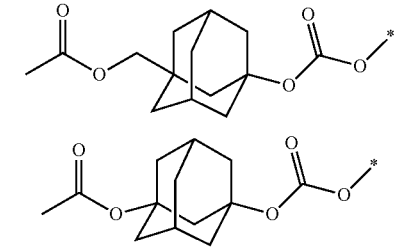

-continued

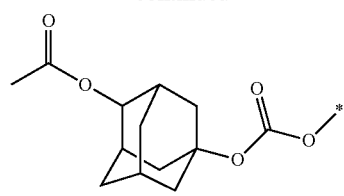

In each formula, * represents a binding site to Y.

Examples of the group represented by formula (b1-8) include the following ones.

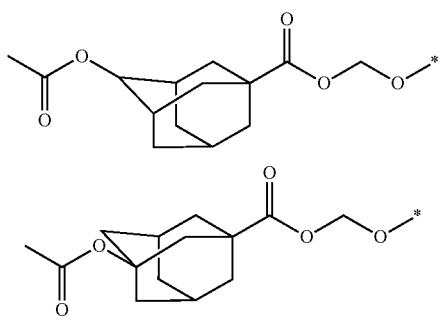

In each formula, * represents a binding site to Y.

Examples of the group represented by formula (b1-2) include the following ones.

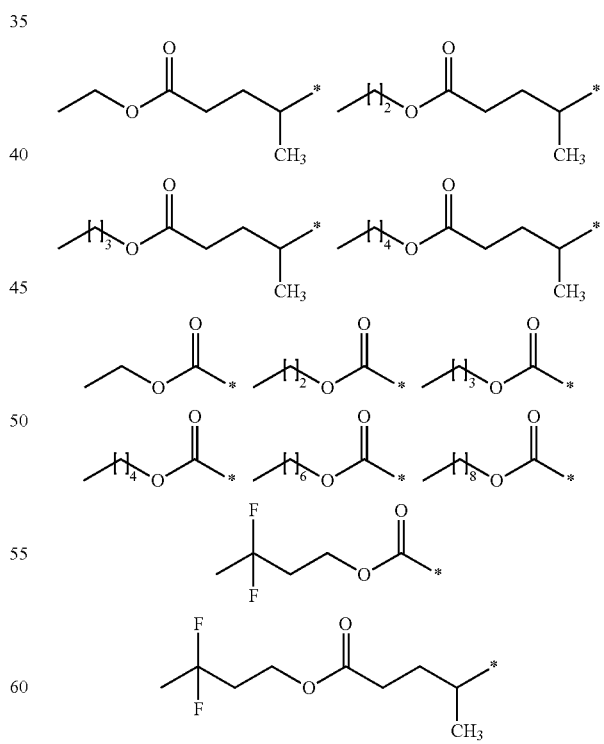

In each formula, * represents a binding site to Y.

Examples of one represented by formula (b1-3) include those represented by formulae (b1-9) to (b1-11).

(b1-9)

(b1-10)

(b1-11)

In these formulae, * represents a binding site to Y.

In formula (b1-9), $L^{b19}$ represents a single bond or a C1-C23 divalent saturated hydrocarbon group where a hydrogen atom can be replaced by a fluorine atom and $L^{b20}$ represents a single bond or a C1-C23 divalent saturated hydrocarbon group where a hydrogen atom can be replaced by a fluorine atom, a hydroxy group or an acyloxy group in which a methylene group can be replaced by an oxygen atom or a carbonyl group and in which a hydrogen atom can be replaced by a hydroxy group, provided that total carbon atoms in $L^{b19}$ and $L^{b20}$ are 23 or less.

In formula (b1-10), $L^{b21}$ represents a single bond or a C1-C21 divalent saturated hydrocarbon group where a hydrogen atom can be replaced by a fluorine atom, $L^{b22}$ represents a single bond or a C1-C21 divalent saturated hydrocarbon group and $L^{b23}$ represents a single bond or a C1-C21 divalent saturated hydrocarbon group where a hydrogen atom can be replaced by a fluorine atom, a hydroxy group or an acyloxy group in which a methylene group can be replaced by an oxygen atom or a carbonyl group and in which a hydrogen atom can be replaced by a hydroxy group, provided that total carbon atoms in $L^{b21}$, $L^{b22}$ and $L^{b23}$ are 21 or less.

In formula (b1-11), $L^{b24}$ represents a single bond or a C1-C20 divalent saturated hydrocarbon group where a hydrogen atom can be replaced by a fluorine atom, $L^{b25}$ represents a C1-C21 divalent saturated hydrocarbon group and $L^{b26}$ represents a single bond or a C1-C20 divalent saturated hydrocarbon group where a hydrogen atom can be replaced by a fluorine atom, a hydroxy group or an acyloxy group in which a methylene group can be replaced by an oxygen atom or a carbonyl group and in which a hydrogen atom can be replaced by a hydroxy group, provided that total carbon atoms in $L^{b24}$, $L^{b25}$ and $L^{b25}$ are 21 or less.

In formulae (b1-9) to (b1-11), the number of the carbon atoms for the divalent saturated hydrocarbon groups include that of the carbon atoms in an acyloxy group, if a hydrogen atom therein has been replaced by the group.

Examples of acyloxy group include an acetyloxy group, a propionyloxy group, a butyryloxy group, a cyclohexylcarbonyloxy group, and an adamantylcarbonyloxy group.

Examples of acyloxy group which has a substituent include an oxoadamantylcarbonyloxy group, a hydroxyadamantylcarbonyloxy group, an oxocyclohexylcarbonyloxy group, and a hydroxycyclohexylcarbonyloxy group.

Examples of the group represented by formula (b1-9) include the following ones.

In each formula, * represents a binding site to Y.

Examples of the group represented by formula (b1-10) include the following ones.

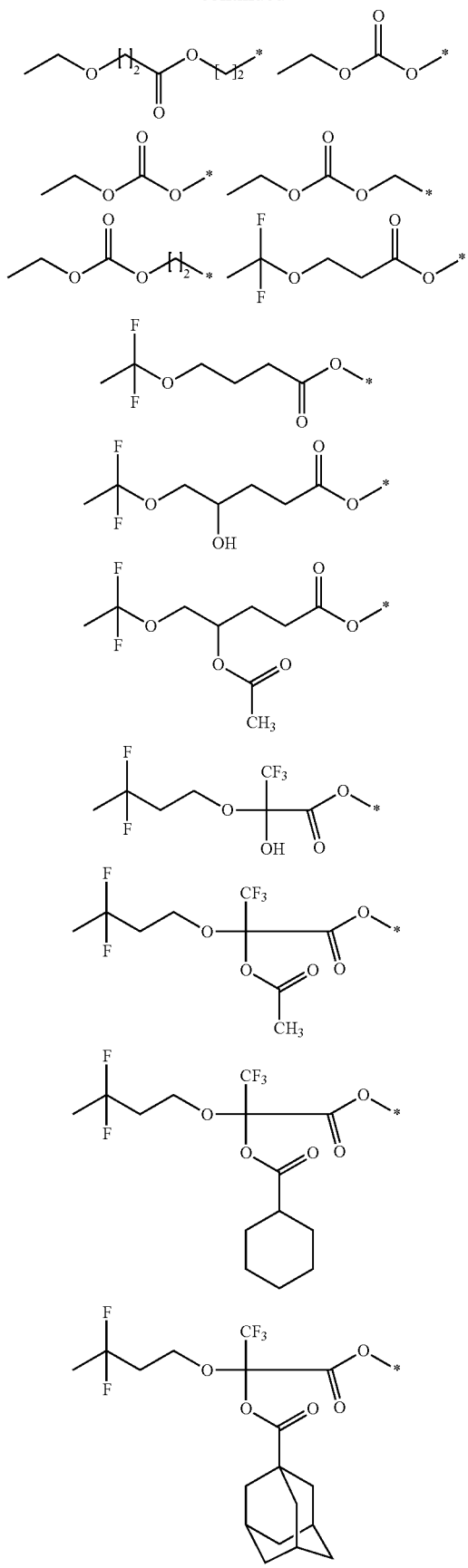
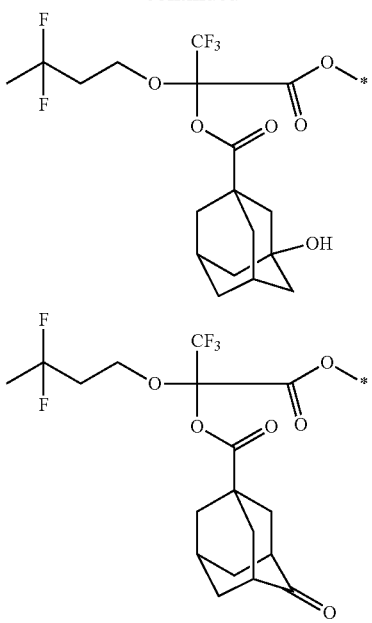
In each formula, * represents a binding site to Y.
Examples of the group represented by formula (b1-11) include the following ones.
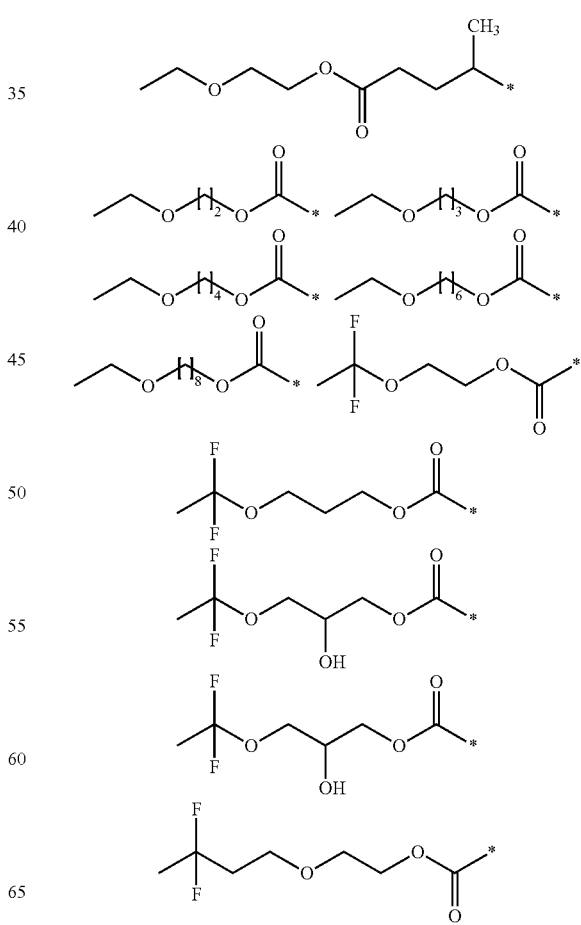

-continued

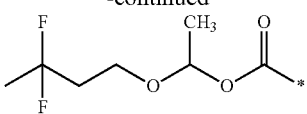
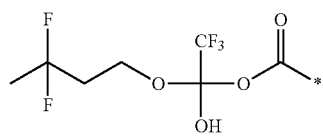
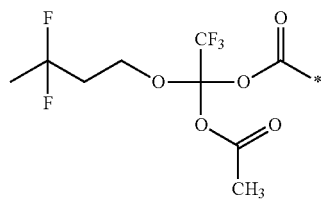
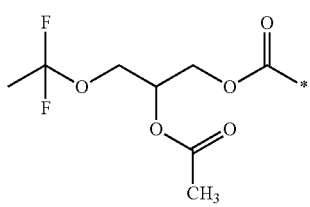
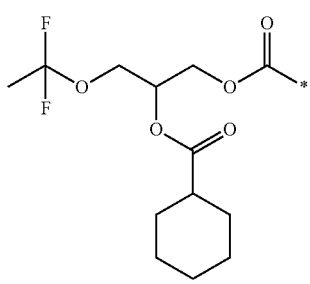
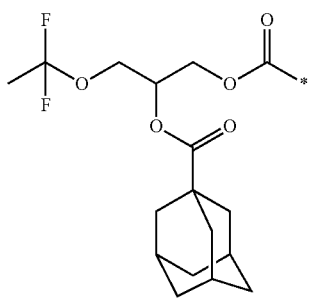
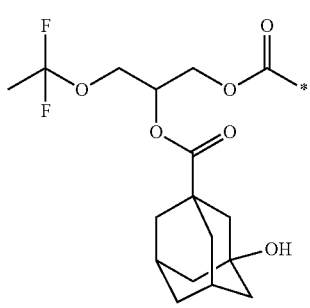

-continued

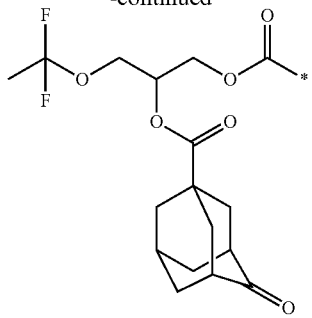

In each formula, * represents a binding site to Y.

Y represents a methyl group or a C3-C18 alicyclic hydrocarbon group where a methylene group can be replaced by an oxygen atom, a carbonyl group or a sulfonyl group and where a hydrogen atom can be replaced by a substituent.

The alicyclic hydrocarbon group may be a monocyclic or polycyclic group.

Preferable examples of the C3-C18 monovalent alicyclic hydrocarbon group include a C3-C18 cycloalkyl group, and a C3-C12 cycloalkyl group is more preferable. The cycloalkyl group may be a monocyclic or a polycyclic. Herein, "cyloalkyl group" contains a cycloalkyl group wherein a C1-C12 alkyl group is bonded to its ring.

Examples of the alicyclic hydrocarbon group include those represented by formulae (Y1) to (Y11).

Examples of the alicyclic hydrocarbon group where a methylene group has been replaced by an oxygen atom, a sulfonyl group or a carbonyl group include those represented by formulae (Y12) to (Y27).

 (Y1)

 (Y2)

 (Y3)

 (Y4)

 (Y5)

 (Y6)

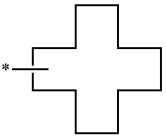 (Y7)

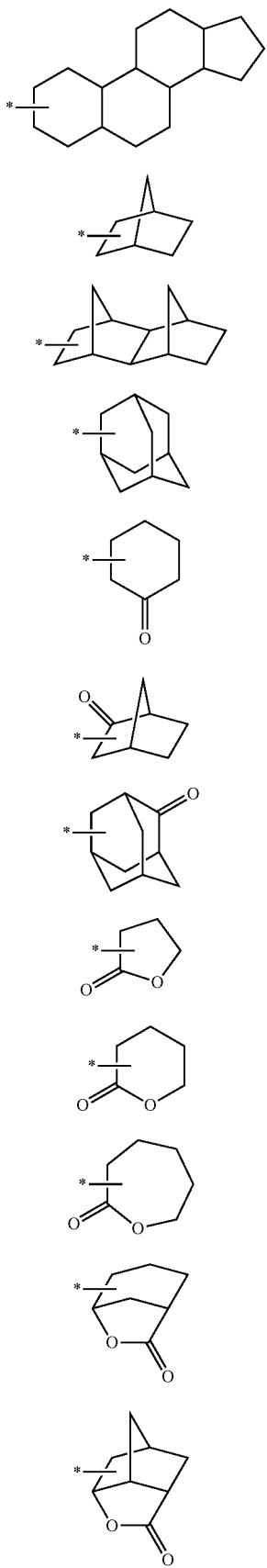
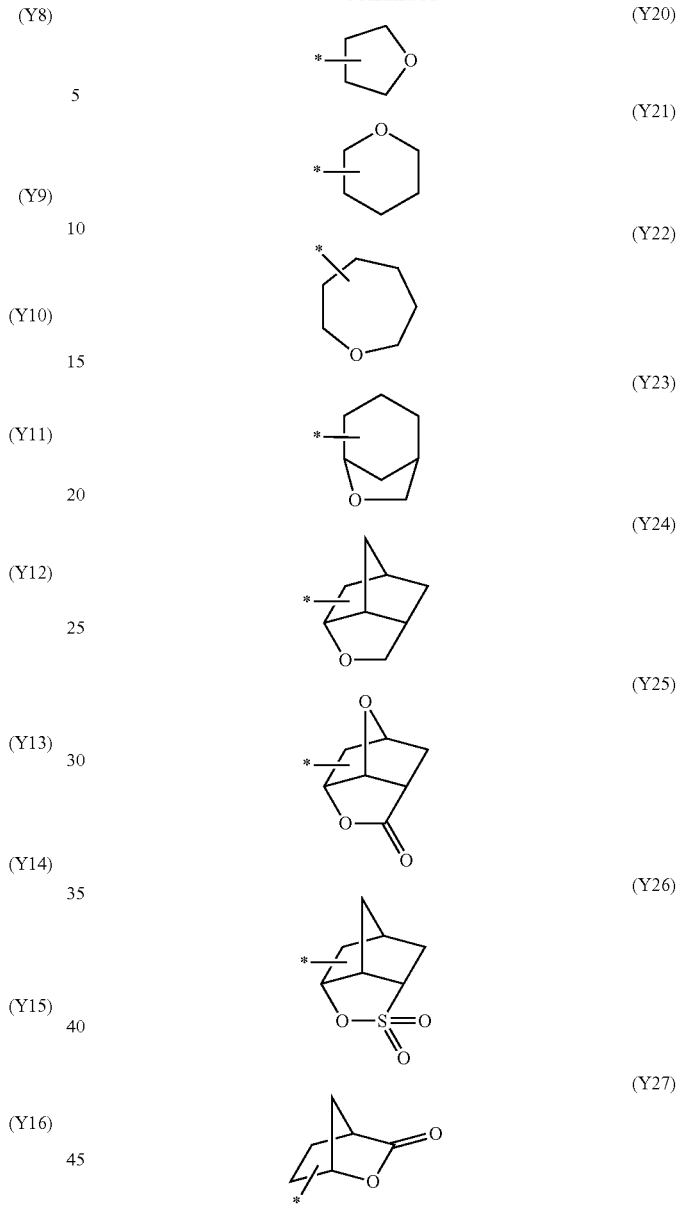

Among them, preferred are groups represented by formulae (Y1) to (Y19), and more preferred are groups represented by formulae (Y11), (Y14), (Y15) and (Y19), and still more preferred are groups represented by formulae (Y11) and (Y14).

The monovalent alicyclic hydrocarbon group can have a substituent.

Examples of the substituent include a halogen atom, a hydroxyl group, a C1-C12 alkyl group which can have a hydroxy group, a C1-C12 alkoxy group, a C3-C16 alicyclic hydrocarbon group or a C6-C18 aromatic hydrocarbon group, a C7-C21 aralkyl group, a C2-C4 acyl group, a glycidyloxy group, and —$(CH_2)_{ja}$—O—CO—$R^{b1}$— in which $R^{b1}$ represents a C1-C16 alkyl group, a C3-C16 alicyclic hydrocarbon group or a C6-C18 aromatic hydrocarbon group and ja represents an integer of 0 to 4.

Examples of the alkyl group which has a hydroxy group include a hydroxymethyl group and a hydroxyethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the aromatic hydrocarbon group include aryl groups such as a phenyl group, a naphthyl group, an anthlyl group, a p-methylphenyl group, p-tert-butylphenyl group, a p-adamantylphenyl group, a tolyl group, a xylyl group, a cumenyl group, a mesityl group, a biphenyl group, a phenanthryl group, a 2,6-diethyl phenyl group, and 2-methyl-6-ethyl phenyl.

Examples of the aralkyl groups include a benzyl group, a phenethyl group, a phenylpropyl group, a naphthylmethyl group and a naphthylethyl group.

Examples of the acyl groups include an acetyl group, propyonyl group and a butylyl group.

Examples of the halogen atom include a fluorine atom, a chlorine atom, a bromine atom and an iodine atom.

Specific examples of Y include the following ones.

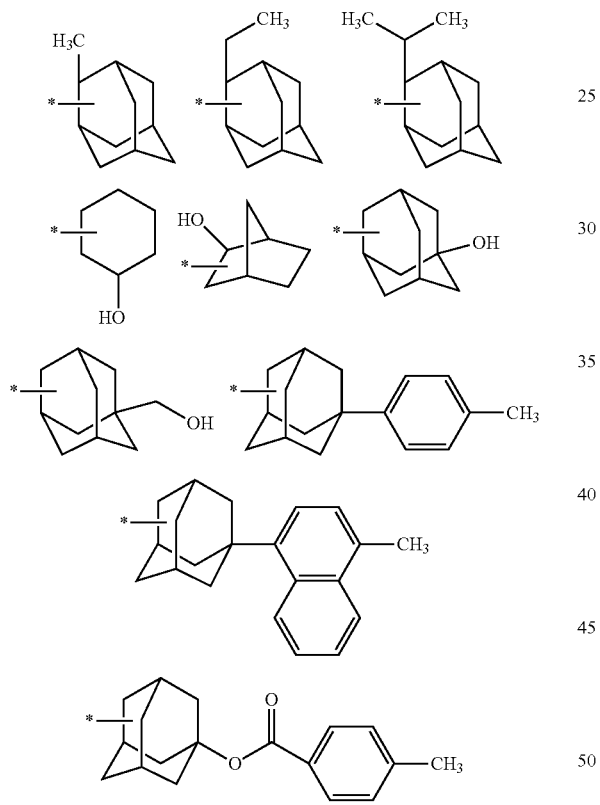

Y is preferably a C3-C18 alicyclic hydrocarbon group which can have a substituent, more preferably an adamantyl group where a hydrogen atom can be replaced by a substituent and where a methylene group can be replaced by an oxygen atom, a sulfonyl group or a carbonyl group, and still more preferably an adamantyl group, a hydroxyadamantyl group or an oxoadamantyl group.

Specific examples of the anion represented by formula (I-A) include the following anions represented by formulae (I-A-1) to (I-A-31). Preferred are those represented by formulae (I-A-1) to (I-A-29), more preferred are those represented by formulae (I-A-1) to (I-A-4), (I-A-9), (I-A-10), and (I-A-24) to (I-A-29).

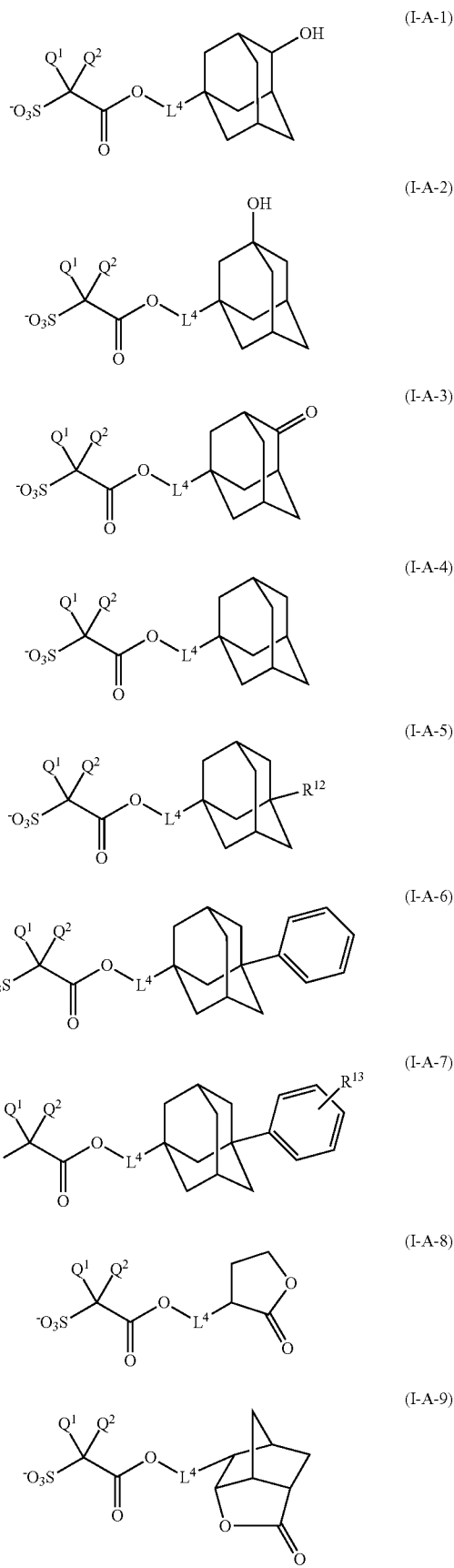

(I-A-10) 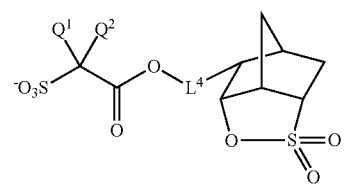
(I-A-11) 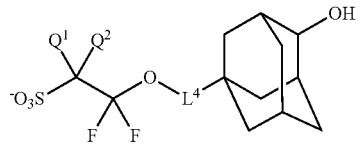
(I-A-12) 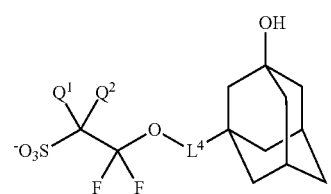
(I-A-13) 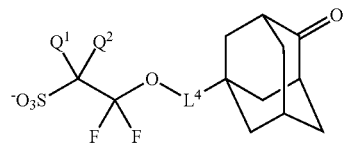
(I-A-14) 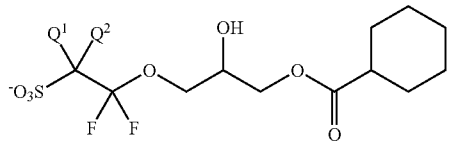
(I-A-15) 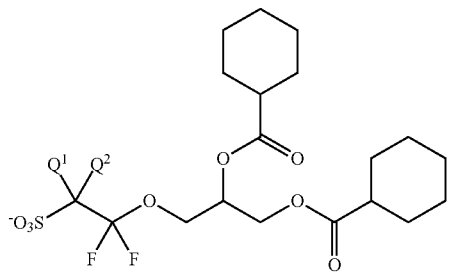
(I-A-16) 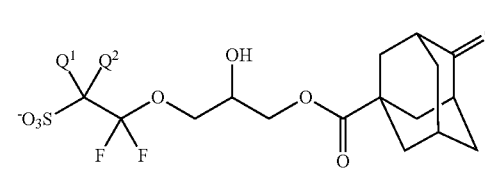
(I-A-17) 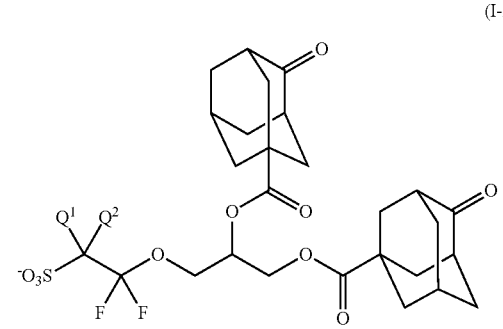
(I-A-18) 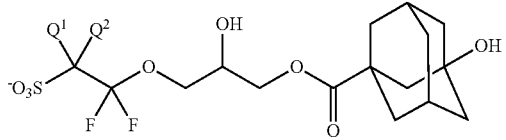
(I-A-19) 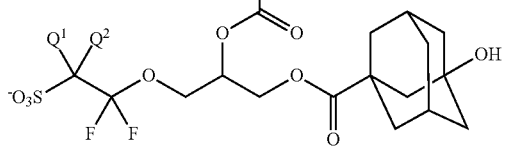
(I-A-20) 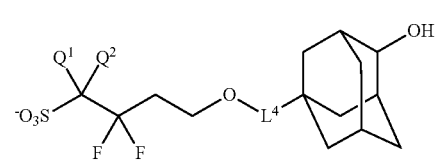
(I-A-21) 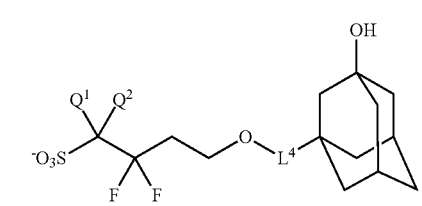
(I-A-22) 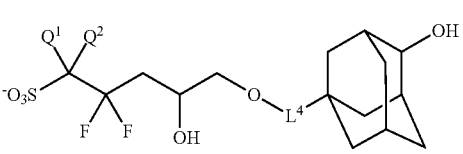
(I-A-23) 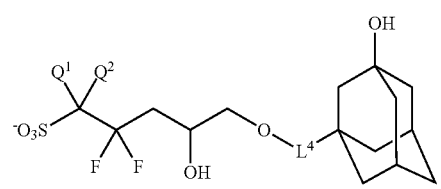
(I-A-24) 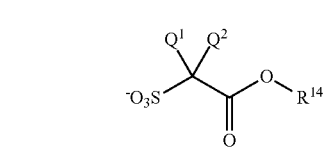
(I-A-25) 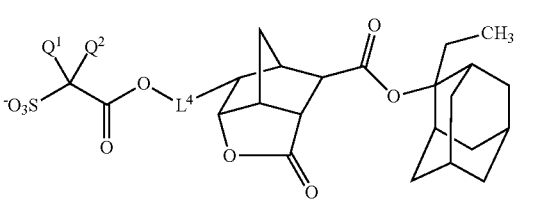

(I-A-26)
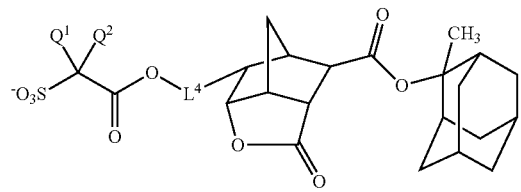

(I-A-27)
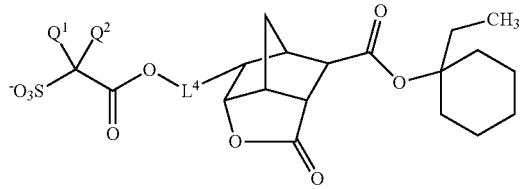

(I-A-28)
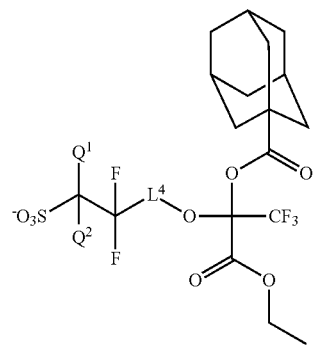

(I-A-29)
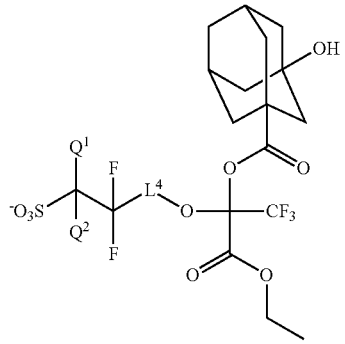

(I-A-30)
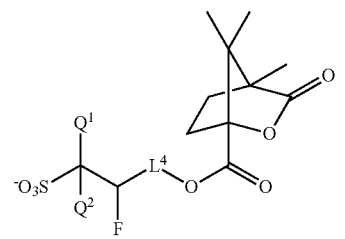

(I-A-31)
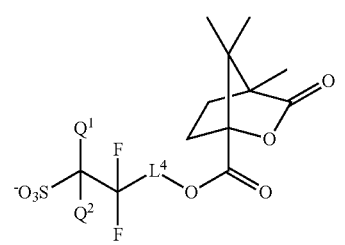

In each formula, $R^{12}$, $R^{13}$ and $R^{14}$ each independently represent a C1-C4 alkyl group, preferably a methyl group. $L^4$ represents a single group, or a C1-C4 alkanediyl group. $Q^1$ and $Q^2$ are each independently as defined above.

Specific examples of the anion represented by formula (I-A) include preferably the following anions represented by formulae (Ia-1) to (Ia-11).

(Ia-1)
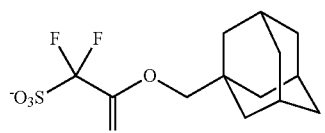

(Ia-2)
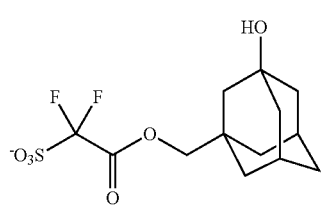

(Ia-3)
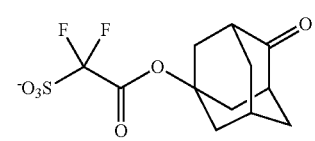

(Ia-4)
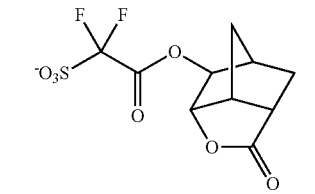

(Ia-5)
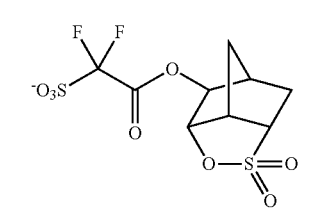

(Ia-6)
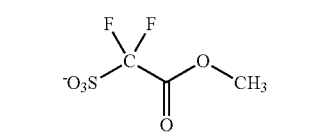

(Ia-7)
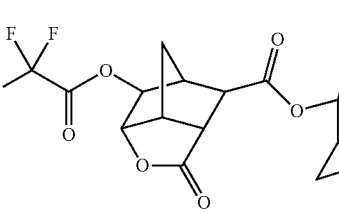

(Ia-8)
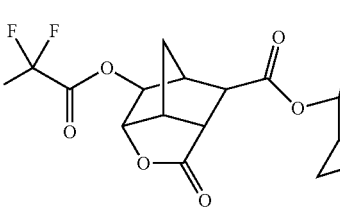

-continued

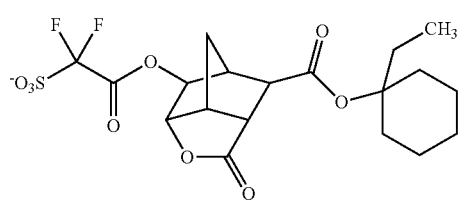
(Ia-9)

(Ia-10)

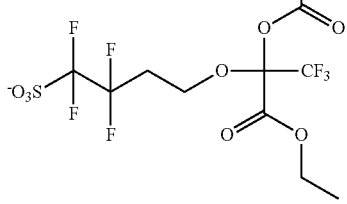
(Ia-10)

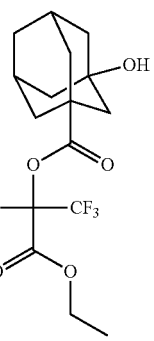
(Ia-11)

Examples of sulfonylimide anions include the following ones.

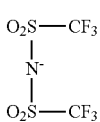
(I-b-1)

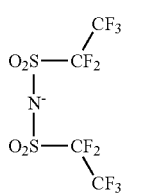
(I-b-2)

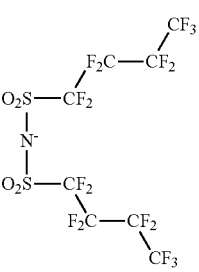
(I-b-3)

-continued

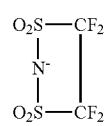
(I-b-4)

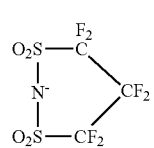
(I-b-5)

As the organic anion represented by A⁻, the anions represented by formulae (Ia-1) to (Ia-3) and (Ia-7) to (Ia-11) are preferred.

Specific examples of Salt (I) include the salts listed in Tables 1 and 2.

In Tables, the symbols recited in columns represent the formulae of anions or cation which each salt has. For example, Salt (I-1) is represented as follow.

TABLE 1

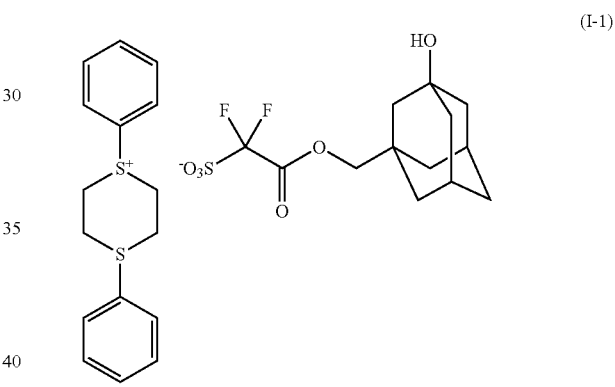
(I-1)

| Salt (I) | A⁻/A⁻ | Cation (I) |
|---|---|---|
| (I-1) | (Ia-2)/(Ia-2) | (I-c-1) |
| (I-2) | (Ia-3)/(Ia-3) | (I-c-1) |
| (I-3) | (Ia-7)/(Ia-7) | (I-c-1) |
| (I-4) | (Ia-8)/(Ia-8) | (I-c-1) |
| (I-5) | (Ia-10)/(Ia-10) | (I-c-1) |
| (I-6) | (Ia-11)/(Ia-11) | (I-c-1) |
| (I-7) | (Ia-2)/(Ia-2) | (I-c-3) |
| (I-8) | (Ia-3)/(Ia-3) | (I-c-3) |
| (I-9) | (Ia-7)/(Ia-7) | (I-c-3) |
| (I-10) | (Ia-8)/(Ia-8) | (I-c-3) |
| (I-11) | (Ia-10)/(Ia-10) | (I-c-3) |
| (I-12) | (Ia-11)/(Ia-11) | (I-c-3) |
| (I-13) | (Ia-2)/(Ia-2) | (I-c-4) |
| (I-14) | (Ia-3) (Ia-3) | (I-c-4) |
| (I-15) | (Ia-7)/(Ia-7) | (I-c-4) |
| (I-16) | (Ia-8)/(Ia-8) | (I-c-4) |
| (I-17) | (Ia-10)/(Ia-10) | (I-c-4) |
| (I-18) | (Ia-11)/(Ia-11) | (I-c-4) |
| (I-19) | (Ia-2)/(Ia-2) | (I-c-7) |
| (I-20) | (Ia-3)/(Ia-3) | (I-c-7) |
| (I-21) | (Ia-7)/(Ia-7) | (I-c-7) |
| (I-22) | (Ia-8)/(Ia-8) | (I-c-7) |
| (I-23) | (Ia-10)/(Ia-10) | (I-c-7) |
| (I-24) | (Ia-11)/(Ia-11) | (I-c-7) |

TABLE 2

| Salt (I) | A⁻ | Cation (I) |
|---|---|---|
| (I-25) | (Ia-2)/(Ia-2) | (I-c-12) |
| (I-26) | (Ia-3)/(Ia-3) | (I-c-12) |
| (I-27) | (Ia-7)/(Ia-7) | (I-c-12) |
| (I-28) | (Ia-8)/(Ia-8) | (I-c-12) |
| (I-29) | (Ia-10)/(Ia-10) | (I-c-12) |
| (I-30) | (Ia-11)/(Ia-11) | (I-c-12) |
| (I-31) | (Ia-2)/(Ia-2) | (I-c-14) |
| (I-32) | (Ia-3)/(Ia-3) | (I-c-14) |
| (I-33) | (Ia-7)/(Ia-7) | (I-c-14) |
| (I-34) | (Ia-8)/(Ia-8) | (I-c-14) |
| (I-35) | (Ia-10)/(Ia-10) | (I-c-14) |
| (I-36) | (Ia-11)/(Ia-11) | (I-c-14) |
| (I-37) | (Ia-2)/(Ia-2) | (I-c-16) |
| (I-38) | (Ia-3)/(Ia-3) | (I-c-16) |
| (I-39) | (Ia-7)/(Ia-7) | (I-c-16) |
| (I-40) | (Ia-8)/(Ia-8) | (I-c-16) |
| (I-41) | (Ia-10)/(Ia-10) | (I-c-16) |
| (I-42) | (Ia-11)/(Ia-11) | (I-c-16) |
| (I-43) | (Ia-2)/(Ia-3) | (I-c-1) |
| (I-44) | (Ia-2)/(Ia-3) | (I-c-3) |
| (I-45) | (Ia-2)/(Ia-3) | (I-c-4) |
| (I-46) | (Ia-2)/(Ia-3) | (I-c-7) |
| (I-47) | (Ia-2)/(Ia-3) | (I-c-12) |
| (I-48) | (Ia-2)/(Ia-2) | (I-c-22) |
| (I-49) | (Ia-3)/(Ia-3) | (I-c-22) |
| (I-50) | (Ia-7)/(Ia-7) | (I-c-22) |
| (I-51) | (Ia-8)/(Ia-8) | (I-c-22) |
| (I-52) | (Ia-10)/(Ia-10) | (I-c-22) |
| (I-53) | (Ia-11)/(Ia-11) | (I-c-22) |

As Salt (I), salt (I-1), salt (I-2), salt (I-4), salt (I-5), salt (I-7), salt (I-8), salt (I-10), salt (I-11), salt (I-13), salt (I-14), salt (I-16), salt (I-17), salt (I-19), salt (I-20), salt (I-22), salt (I-23), salt (I-43), salt (I-44), salt (I-48) and salt (I-49) are preferred, and salt (I-1), salt (I-2), salt (I-4), salt (I-5), salt (I-7), salt (I-8), salt (I-10), salt (I-11), salt (I-13), salt (I-14), salt (I-16), salt (I-17), salt (I-19), salt (I-20), salt (I-22) and salt (I-23) are more preferred.

Salt (I) can be produced by reacting a salt represented by formula (I-a) with a salt represented by formula (I-b), in the presence of a catalyst, in a solvent such as chloroform:

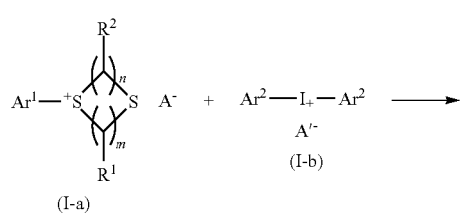

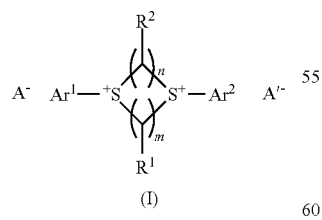

wherein $R^1$, $R^2$, $Ar^1$, $Ar^2$, $A^-$, $A'^-$, m and n are the same as defined above.

Examples of the catalyst for the reaction include copper (II) acetate. Examples of the salt represented by formula (I-a) include the following ones.

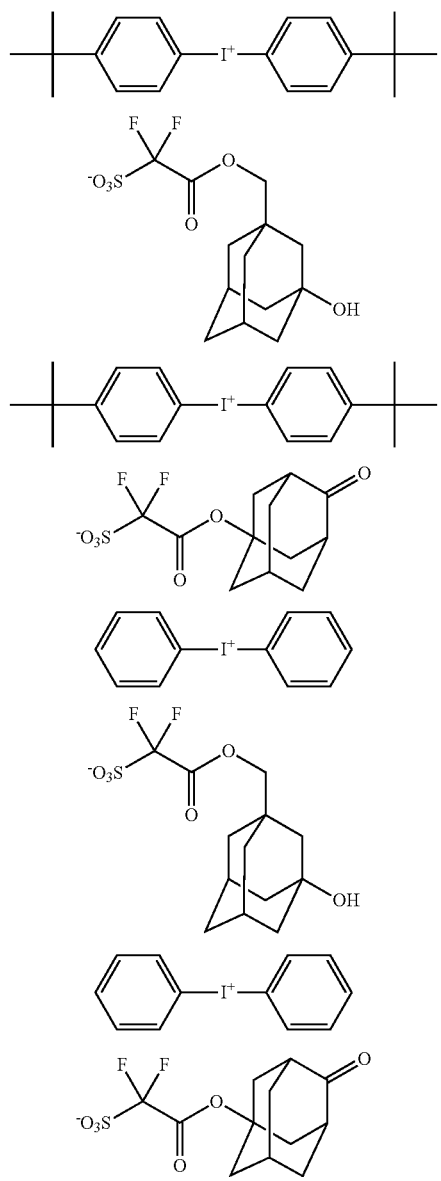

The salt represented by formula (I-a) can be produced by reacting a salt represented by formula (I-c) with a salt represented by formula (I-d), in the presence of a catalyst, in a solvent such as chloroform:

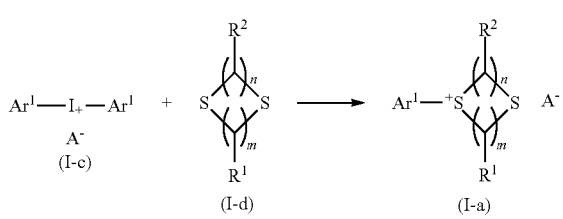

wherein $R^1$, $R^2$, $Ar^1$, $A^-$, m and n are the same as defined above. Examples of the catalyst for the reaction include copper (II) acetate. Examples of the salt represented by formula (I-c) include the following ones.

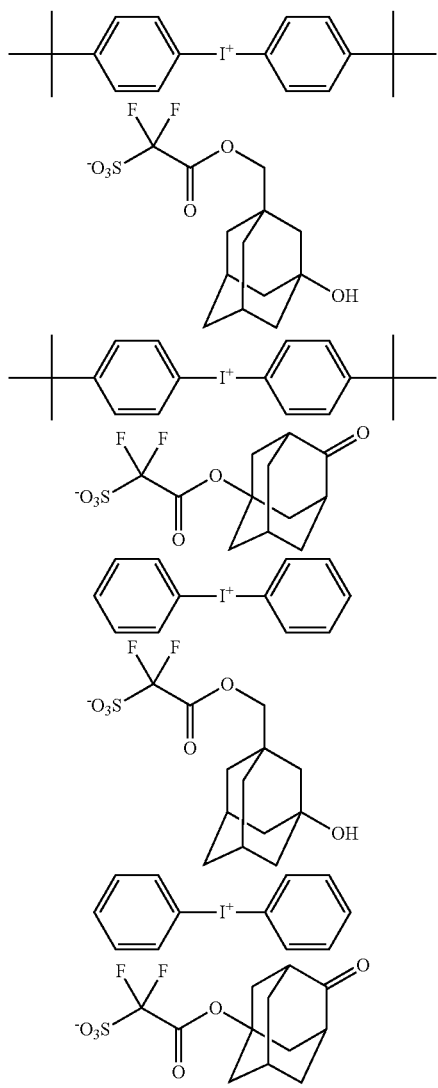

Examples of the salt represented by formula (I-d) include the salt in which $R^1$ and $R^2$ are hydrogen atoms and n and m are each independently 1 or 2, specifically the following one.

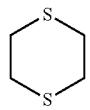

<Acid Generator>

The acid generator of the present invention comprises Salt (I). The acid generator of the present invention can comprise two or more kinds of Salt (I).

Here, the acid generator of the present invention means salts capable of generating an acid with a developer described later.

The acid generator can comprise one or more known acid generators in addition to Salt (I).

The known acid generators may be an ionic acid generator or a nonionic acid generator, which is preferably an ionic acid generator.

Examples of the acid generator include a salt which consists of an organic sulfonium and an organic sulfonic acid, and acid generators as mentioned in JP2013-68914A1, JP2013-3155A1 and JP2013-11905A1.

Examples of the salt which consists of an organic sulfonium and an organic sulfonic acid include those which consist of an arylsulfonium cation, preferably a triarylsulfonium cation, and the anion of formula (I-A).

Specific examples of the acid generator include the following salts represented by formulae (B1-1) to (B1-28). Among them, those which comprise anarylsulfoniumcation are preferred, the salts represented by formulae (B1-1), (B1-2), (B1-3), (B1-6), (B1-11), (B1-12), (B1-13), (B1-14), (B1-20), (B1-21), (B1-22), (B1-23), (B1-24), (B1-25) and (B1-26) are more preferred, and the salts represented by formulae (B1-1), (B1-2), (B1-3), (B1-6), (B1-11), (1-12), (1-13), (B1-14), (B1-20), (B1-21), (B1-22), (B1-23) and (B1-24) are still more preferred.

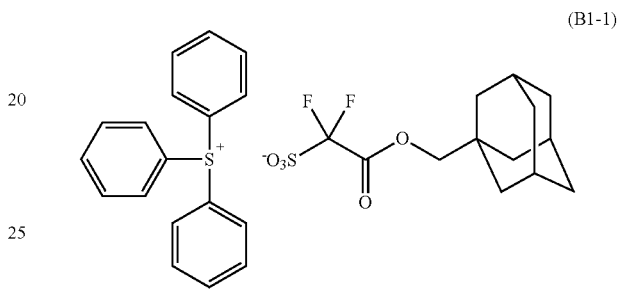

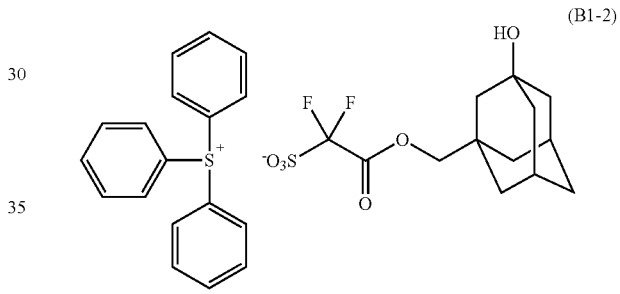

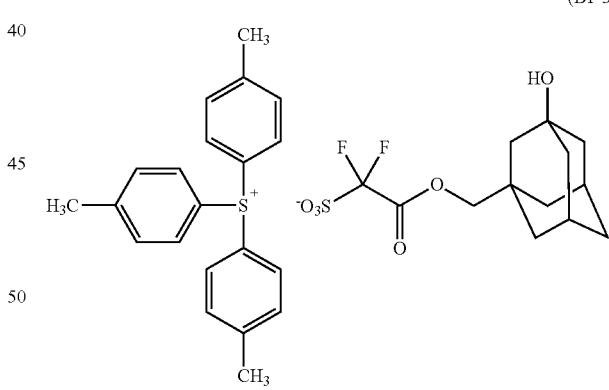

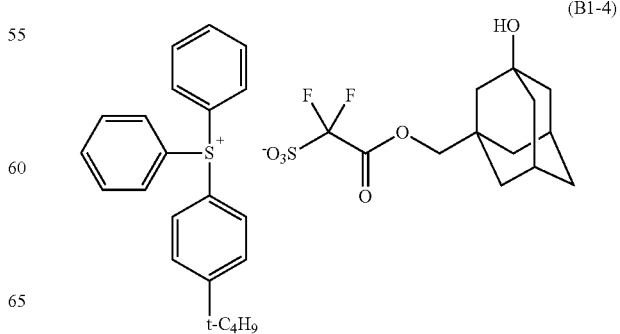

-continued
(B1-5)
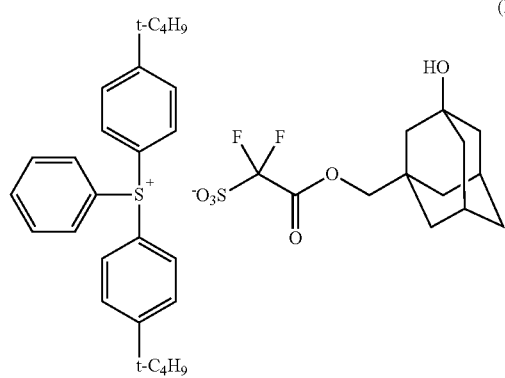
(B1-6)
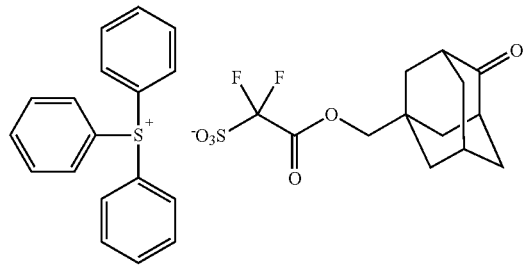
(B1-7)
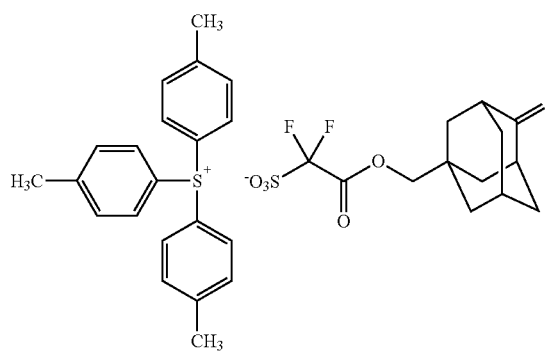
(B1-8)
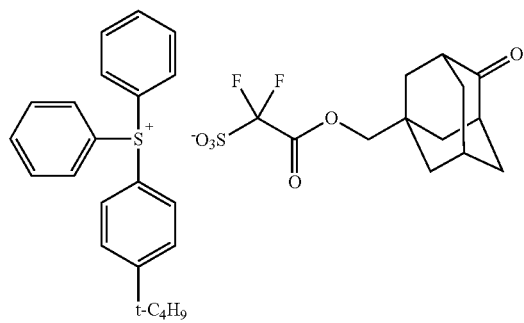
(B1-9)
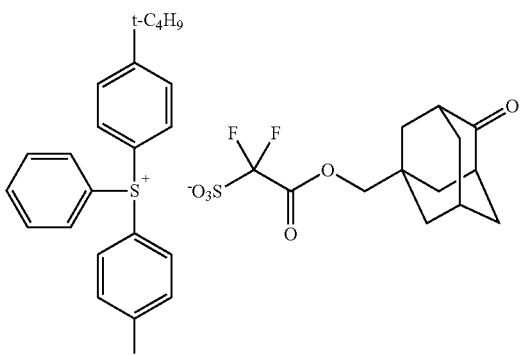
(B1-10)
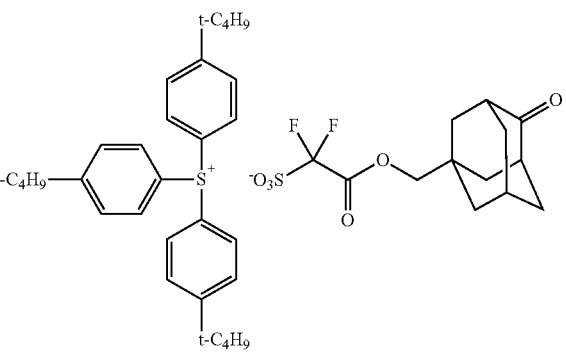
(B1-11)
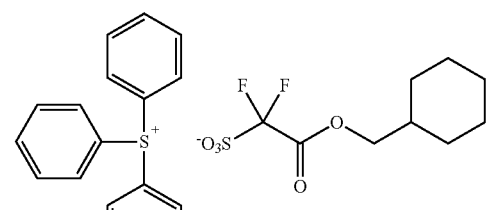
(B1-12)
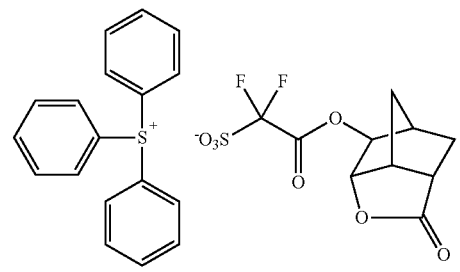
(B1-13)

(B1-14)
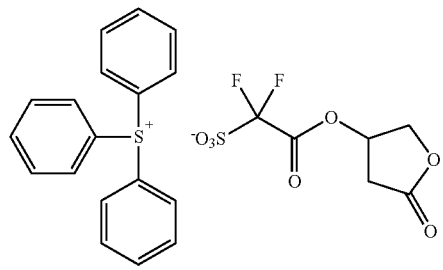
(B1-15)
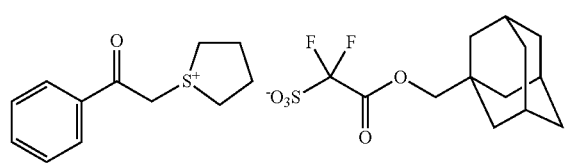
(B1-16)
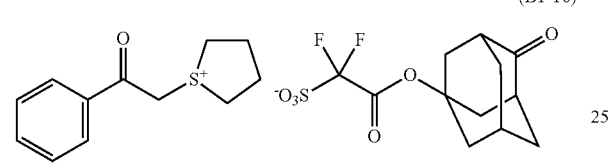
(B1-17)
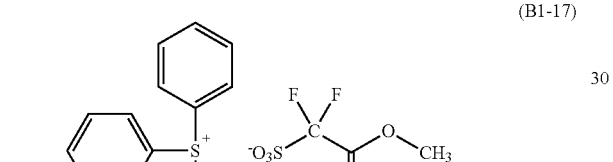
(B1-18)
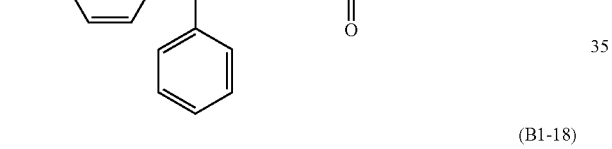
(B1-19)
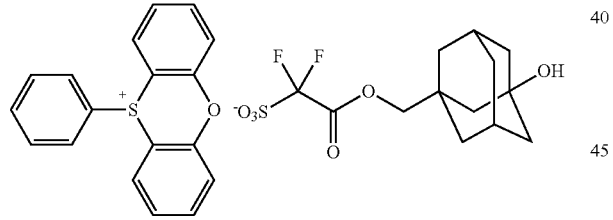
(B1-20)
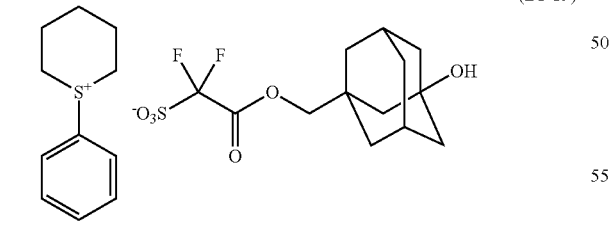
(B1-21)
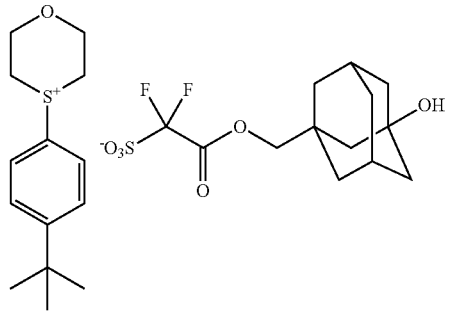
(B1-22)
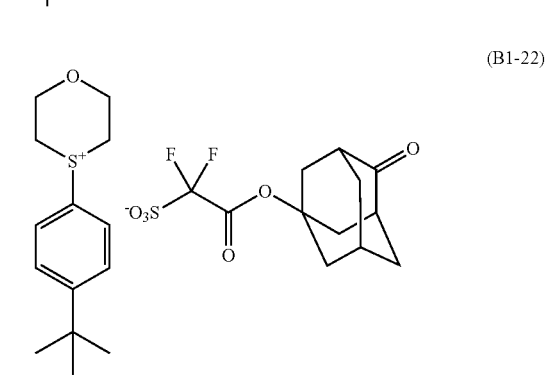
(B1-23)
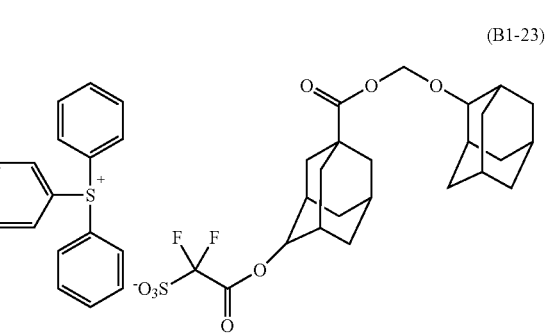
(B1-24)
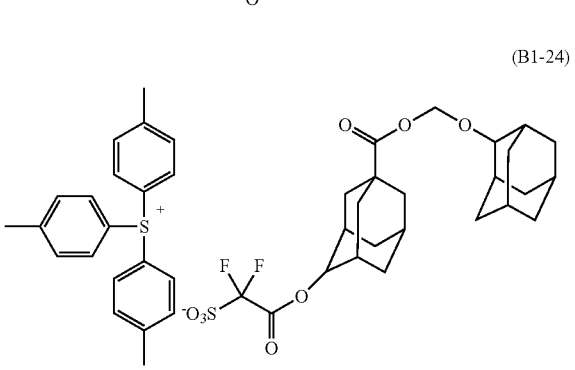
(B1-25)
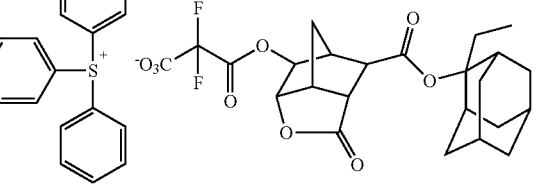

-continued

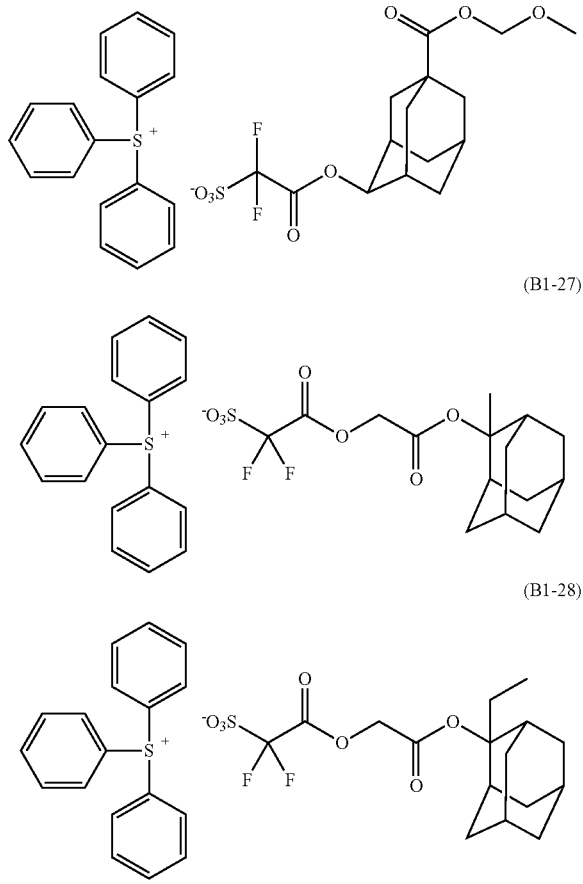

(B1-26)
(B1-27)
(B1-28)

The acid generator of the present invention may consist of Salt (I). When the acid generator of the present invention comprises Salt (I) and the acid generator other than Salt (I), the content of Salt (I) is preferably 10 parts by mass or more and more preferably 30 parts by mass or more, per 100 parts by mass of the acid generator of the present invention.

<Photoresist Composition>

The photoresist composition of the present invention comprises Salt (I) and a resin having an acid-labile group which resin is sometimes referred to as "Resin (A)".

The photoresist composition may comprise a known acid generator as mentioned above, a quencher, or a solvent.

The photoresist composition comprises preferably a quencher, or a solvent, more preferably both of them.

The content of Salt (I) is usually 1 part by mass or more, preferably 2 parts by mass or more, per 100 parts by mass of the resin. The content of the acid generator is usually 20 parts by mass or less, preferably 15 parts by mass or less, per 100 parts by mass of the resin.

The content of known acid generators is usually 1 part by mass or more, preferably 2 parts by mass or more, per 100 parts by mass of the resin. The content of the acid generator is usually 20 parts by mass or less, preferably 15 parts by mass or less, per 100 parts by mass of the resin.

The total content of known acid generators and Salt (I) is usually 1.5 part by mass or more, preferably 3 parts by mass or more, per 100 parts by mass of the resin. The total content of them is usually 40 parts by mass or less, preferably 35 parts by mass or less, per 100 parts by mass of the resin.

Resin (A) usually comprises a structural unit having an acid-labile group. Hereinafter, the structural unit is sometimes referred to as "structural unit (a1)".

Preferably Resin (A) further Comprises another structural unit than the structural unit (a1), i.e. a structural unit having no acid-labile group, which is sometimes referred to as "structural unit (s)".

The resin has an acid-labile group. In this specification, "an acid-labile group" means a group which has a hydrophilic group, such as a hydroxyl group or a carboxy group, resulting from removing a leaving group therefrom by the action of an acid.

Examples of the acid-labile group include a group represented by formula (1):

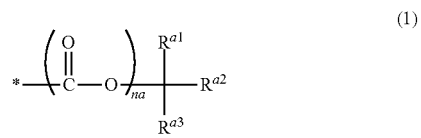

(1)

wherein $R^{a1}$, $R^{a2}$ and $R^{a3}$ independently each represent a C1-C8 alkyl group, a C3-C20 alicyclic hydrocarbon group or a group consisting of them, and $R^{a1}$ and $R^{a2}$ can be bonded each other to form a C2-C20 divalent hydrocarbon group, na represents an integer of 0 or 1, and * represents a binding site; and a group represented by formula (2):

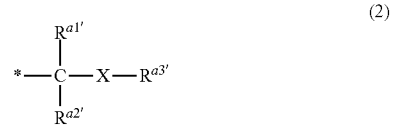

(2)

wherein $R^{a1'}$ and $R^{a2'}$ independently each represent a hydrogen atom or a C1-C12 hydrocarbon group, and $R^{a3'}$ represents a C1-C20 hydrocarbon group, and $R^{a2'}$ and $R^{a3'}$ can be bonded each other to form a C2-C20 divalent hydrocarbon group, and one or more —CH$_2$— in the hydrocarbon group and the divalent hydrocarbon group can be replaced by —O—, —S— or —CO—, X represents an oxygen atom or a sulfur atom, and * represents a binding site.

For $R^{a1}$, $R^{a2}$ and $R^{a3}$, specific examples of the alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3-C20 cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, and the followings:

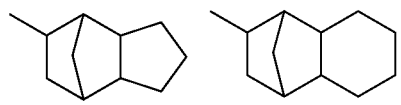

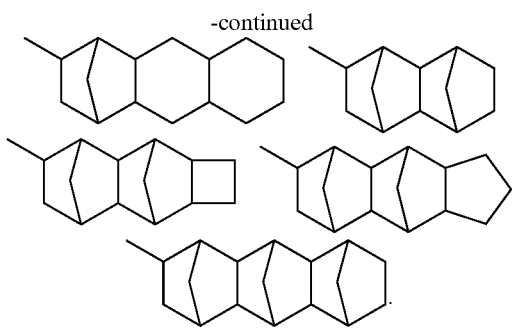

The alicyclic hydrocarbon group preferably has 3 to 16 carbon atoms.

Examples of the group consisting of alkyl and alicyclic hydrocarbon group include a methylcyclohexyl group, a dimethylcyclohexyl group, a methylnorbornyl group, an adamantylmethyl group, and a norbornylethyl group.

The "na" is preferably 0.

When the divalent hydrocarbon group is formed by bonding $R^{a1}$ and $R^{a2}$ each Other, examples of the moiety —C($R^{a1}$)($R^{a2}$)($R^{a3}$) include the following groups and the divalent hydrocarbon group preferably has 3 to 12 carbon atoms.

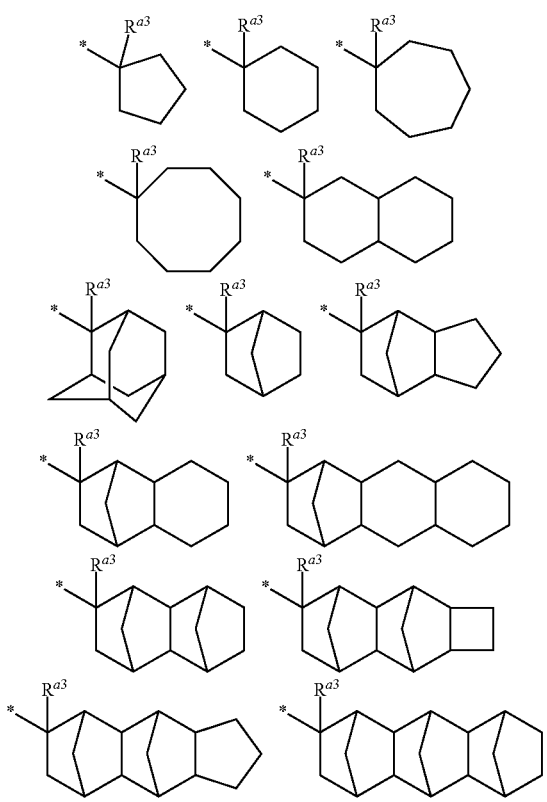

wherein $R^{a3}$ is the same as defined above.

The group represented by formula (I) wherein $R^{a1}$, $R^{a2}$ and $R^{a3}$ independently each represent a C1-C8 alkyl group such as a tert-butyl group, the group represented by formula (I) wherein $R^{a1}$ and $R^{a2}$ are bonded each other to form an adamantyl ring and $R^{a3}$ is a C1-C8 alkyl group such as a 2-alkyl-2-adamantyl group, and the group represented by formula (I) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

For formula (2), examples of the hydrocarbon group include an alkyl group, an alicyclic hydrocarbon group, an aromatic hydrocarbon group and a group consisting of two or more of them.

Examples of the aliphatic hydrocarbon group and the alicyclic hydrocarbon group include the same as described above. Examples of the aromatic hydrocarbon group include an aryl group such as a phenyl group, a naphthylgroup, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

Examples of the divalent hydrocarbon group formed by bonding $R^{a2'}$ and $R^{a3'}$ each other include those formed by removing a hydrogen atom from the hydrocarbon group represented by $R^{a1'}$, $R^{a2'}$ and $R^{a3'}$.

It is preferred that at least one of $R^{a1'}$ and $R^{a2'}$ is a hydrogen atom.

Examples of the group represented by formula (2) include the following.

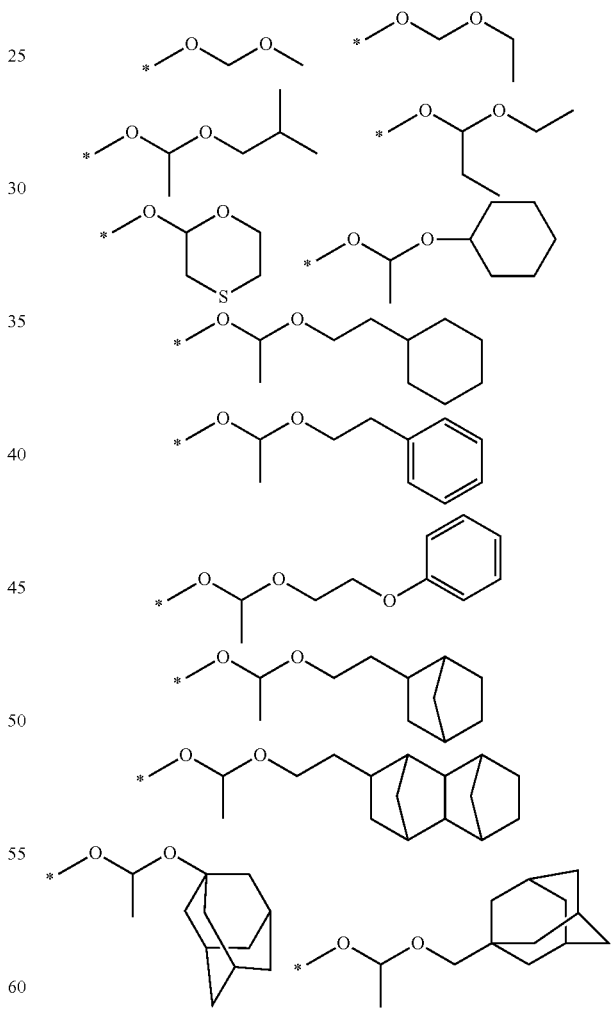

The structural unit (a1) is derived from a compound having an acid-labile group which compound is sometimes referred to as "Monomer (a1)".

Monomer (a1) is preferably a monomer having an acid-labile group in its side chain and an ethylenic unsaturated group, more preferably a (meth)acrylate monomer having an acid-labile group in its side chain, and still more preferably a (meth)acrylate monomer having the group represented by formula (1) or (2).

The (meth)acrylate monomer having an acid-labile group in its side chain is preferably those which comprise a C5-C20 alicyclic hydrocarbon group. The resin which comprises a structural unit derived from such monomers can provide improved resolution for a photoresist pattern to be prepared therefrom.

The structural unit derived from a (meth)acrylate monomer having the group represented by formula (1) is preferably one of structural units represented by formulae (a1-0), (a1-1) and (a1-2).

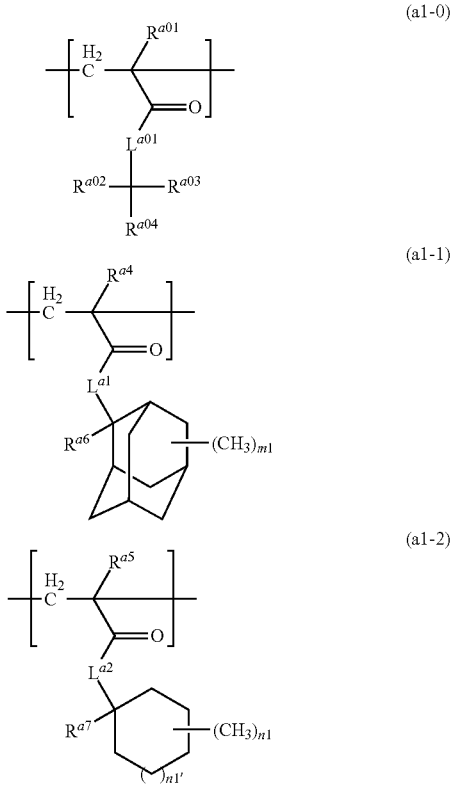

where $L^{a01}$, $L^{a1}$ and $L^{a2}$ each independently represent —O— or *—O—(CH$_2$)$_{k1}$—CO—O— in which k1 represents an integer of 1 to 7 and * represents a binding site to —CO—, $R^{a01}$, $R^{a4}$ and $R^{a5}$ each independently represent a hydrogen atom or a methyl group,
$R^{a02}$, $R^{a03}$, $R^{a04}$, $R^{a4}$, $R^{a6}$ and $R^{a7}$ each independently represent a C1-C8 alkyl group, a C3-C18 alicyclic hydrocarbon group, or a group formed by combining them,
m1 represents an integer of 0 to 14,
n1 represents an integer of 0 to 10, and
n1' represents an integer of 0 to 3.

Hereinafter, the structural units represented by formulae (a1-0), (a1-1) and (a1-2) are respectively referred to as "structural unit (a1-0)", "structural unit (a1-1)" and "structural unit (a1-2)". Resin (A) may comprise two or more of such structural units.

$L^{a01}$ is preferably *—O— or *—O—(CH$_2$)$_{f1}$—CO—O— in which * represents a binding site to —CO—, and f1 represents an integer of 1 to 4, and is more preferably *—O— or *—O—CH$_2$—CO—O—, and is especially preferably *—O—.

$R^{a01}$ is preferably a methyl group.

For $R^{a02}$, $R^{a03}$ and $R^{a04}$, examples of the alkyl group, the alicyclic hydrocarbon group and the group formed by combining them include the same as referred for $R^{a1}$, $R^{a2}$ and $R^{a3}$.

The alkyl group preferably has 1 to 6 carbon atoms.

The alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

The group formed by combining them preferably has 18 carbon atoms or less in total, examples of which include a methylcyclohexyl group, a dimethylcyclohexyl group, and a methylnorbornyl group. Each of $R^{a02}$ and $R^{a03}$ is preferably a C1-C6 alkyl group, more preferably a methyl group and an ethyl group.

$R^{a04}$ is preferably a C1-C6 alkyl group and a C5-C12 alicyclic hydrocarbon group, more preferably a methyl group, an ethyl group, a cyclohexyl group, and an adamantyl group.

Each of $L^{a1}$ and $L^{a2}$ is preferably *—O— or *—O—(CH$_2$)$_{f1}$—CO—O— in which * represents a binding site to —CO—, and f1 is the same as defined above, and is more preferably *—O— or *—O—CH$_2$—CO—O—, and is especially preferably *—O—.

Each of $R^{a4}$ and $R^{a5}$ is preferably a methyl group.

For $R^{a6}$ and $R^{a7}$, examples of the alkyl group include a methyl group, an ethyl group, a propyl group, an isopropyl group, a butyl group, a tert-butyl group, a pentyl group, a heptyl group, a 2-ethylheptyl group and an octyl group.

For $R^{a6}$ and $R^{a7}$, examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic alicyclic hydrocarbon group such as a decahydronaphthyl group, an adamantyl group, a norbornyl group, a methylnorbornyl group and the following. For $R^{a6}$ and $R^{a7}$, examples of the group consisting of an alkyl group and an alicyclic hydrocarbon group include an aralkyl group such as a benzyl group, and a phenethyl group.

The alkyl group represented by $R^{a6}$ and $R^{a7}$ is preferably a C1-C6 alkyl group.

The alicyclichydrocarbon group represented by $R^{a6}$ and $R^{a7}$ is preferably a C3-C8 alicyclichydrocarbon group, more preferably a C3-C6 alicyclic hydrocarbon group.

The "m1" is preferably an integer of 0 to 3, and is more preferably 0 or 1.

The "n1" is preferably an integer of 0 to 3, and is more preferably 0 or 1.

The "n1'" is preferably 0 or 1.

Examples of the monomers from which the structural units (a1-0), (a1-1) and (a1-2) are derived include those represented by formulae (a1-0-1) to (a1-0-12), preferably those represented by formulae (a1-0-1) to (a1-0-10).

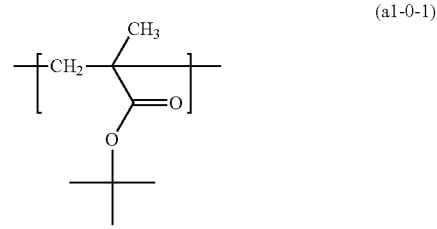

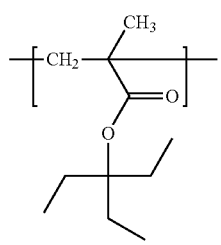 (a1-0-2)
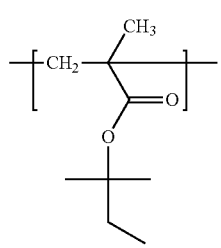 (a1-0-3)
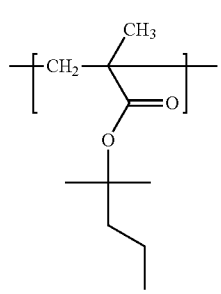 (a1-0-4)
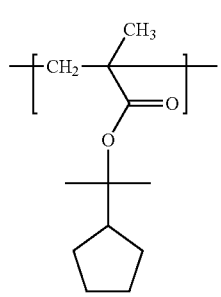 (a1-0-5)
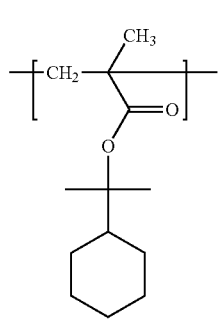 (a1-0-6)
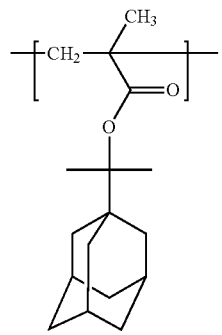 (a1-0-7)
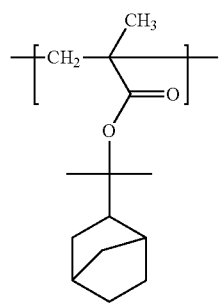 (a1-0-8)
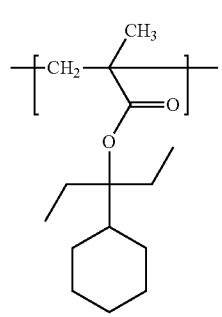 (a1-0-9)
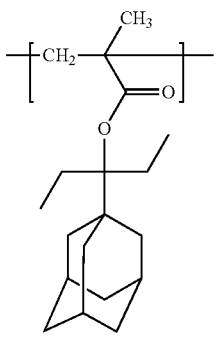 (a1-0-10)
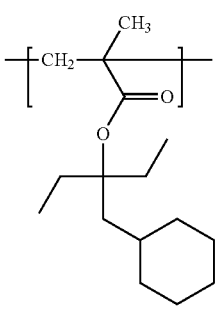 (a1-0-11)

(a1-0-12)

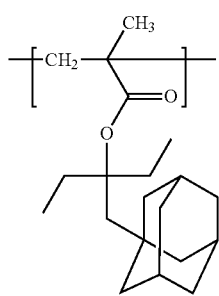

Examples of the monomers from which the structural units (a1-0), (a1-1) and (a1-2) are derived further include such groups that a methyl group is replaced by a hydrogen atom in any one of formulae (a1-0-1) to (a1-0-12).

Examples of the monomer from which the structural unit (a1-1) is derived include the monomers described in JP 2010-204646 A, and the following monomers represented by formulae (a1-1-1) to (a1-1-8), preferably the following monomers represented by formulae (a1-1-1) to (a1-1-4).

(a1-1-1)

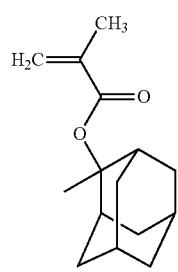

(a1-1-2)

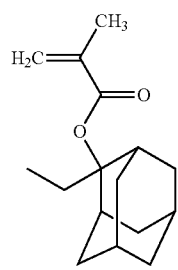

(a1-1-3)

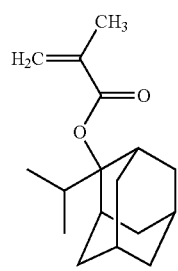

(a1-1-4)

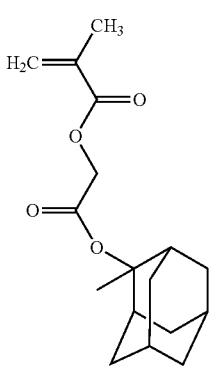

(a1-1-5)

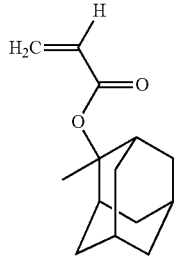

(a1-1-6)

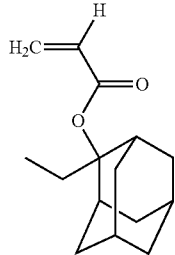

(a1-1-7)

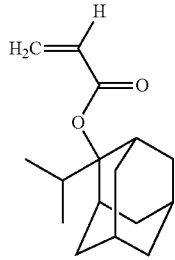

(a1-1-8)

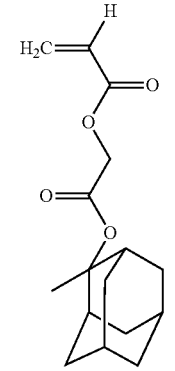

Examples of the monomer from which the structural unit (a1-2) is derived include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate, preferably the monomers represented by formulae (a1-2-1) to (a1-2-12), more preferably the monomers represented by formulae (a1-2-3), (a1-2-4), (a1-2-9) and (a1-2-10), still more preferably the monomers represented by formulae (a1-2-3) and (a1-2-9).

(a1-2-1)
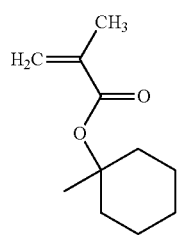

(a1-2-2)
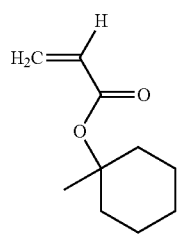

(a1-2-3)
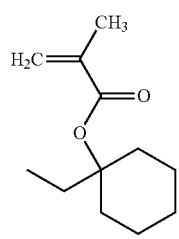

(a1-2-4)
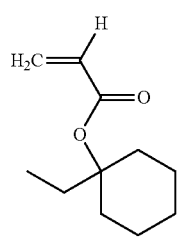

(a1-2-5)
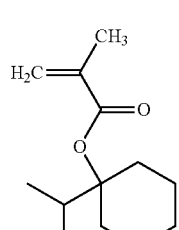

-continued (a1-2-6)
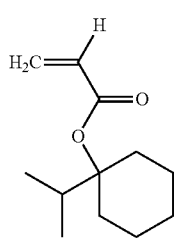

(a1-2-7)
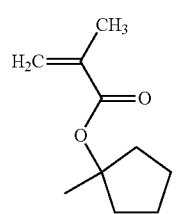

(a1-2-8)
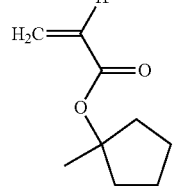

(a1-2-9)
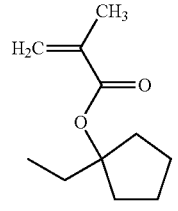

(a1-2-10)
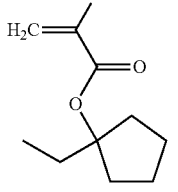

(a1-2-11)
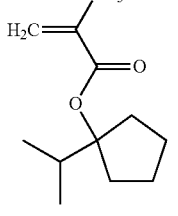

(a1-2-12)
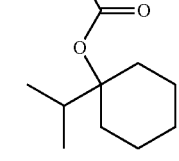

The content of the structural unit having an acid-labile group in the resin is usually 10 to 95% by mole, preferably 15 to 90% by mole and more preferably 20 to 85% by mole based on 100% by mole of all the structural units of the resin. The content of the structural unit having an acid-labile group in the resin can be adjusted by adjusting the amount of the monomer having an acid-labile group based on the total amount of the monomers used for producing the resin.

When the resin comprises one or more of the structural units represented by formulae (a1-0), (a1-1) and (a1-2), the total content of the structural units is usually 10 to 95% by mole, preferably 15 to 90% by mole and more preferably 15 to 90% by mole and still more preferably 20 to 85% by mole based on 100% by mole of all the structural units of the resin.

Other examples of the structural unit (a) having a group represented by formula (I) include a structural unit represented by formula (a1-3):

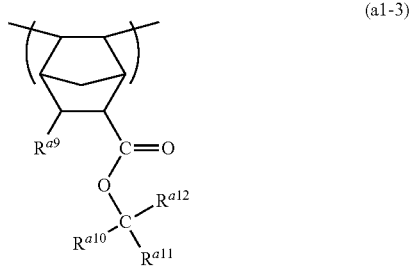

(a1-3)

wherein $R^{a9}$ represents a hydrogen atom, a carboxyl group, a cyano group, a C1-C3 aliphatic hydrocarbon group which can have a hydroxyl group, or a group represented by —COOR$^{a13}$ group in which R$^{a13}$ represents a C1-C8 alkyl group or a C3-C20 alicyclic hydrocarbon group, and a group composed of a C1-C8 aliphatic hydrocarbon group and a C3-C20 alicyclic hydrocarbon group, and the aliphatic hydrocarbon group and the alicyclic hydrocarbon group can have a hydroxyl group, and a methylene in the alkyl group and the alicyclic hydrocarbon group can be replaced by —O— or —CO—, $R^{a10}$, $R^{a11}$ and $R^{a12}$ each independently represent a C1-C12 alkyl group or a C3-C20 alicyclic hydrocarbon group, and $R^{a10}$ and $R^{a11}$ can be bonded each other to form a C3-C20 ring together with the carbon atom to which $R^{a10}$ and $R^{a11}$ are bonded, and the alkyl group and the alicyclic hydrocarbon group can have a hydroxyl group, and a methylene group in alkyl group and the alicyclic hydrocarbon group can be replaced by —O— or —CO—.

As $R^{a9}$, examples of the alkyl group which can have a hydroxyl group include a methyl group, an ethyl group, a propyl group, a hydroxymethyl group and a 2-hydroxyethyl group.

Examples of the aliphatic hydrocarbon group represented by $R^{a13}$ include a methyl group, an ethyl group, a propyl group.

Examples of the alicylic hydrocarbon group represented by $R^{a13}$ include a cyclopropyl group, a cyclobutyl group, an adamantyl group, an adamantylmethyl group, a 1-adamantyl-1-methylethyl group, a 2-oxo-oxolan-3-yl group and a 2-oxo-oxolan-4-yl group.

Examples of the alkyl group represented by $R^{a10}$, $R^{a11}$ and $R^{a12}$ include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group.

The alicylic hydrocarbon group represented by $R^{a10}$, $R^{a11}$ and $R^{a12}$, which may be a monocyclic or polycyclic group. Examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group, a cycloheptyl group, a cyclodecyl group. Examples of the polycyclic alicyclic hydrocarbon group include a hydronaphthyl group, an adamantyl group, a 2-alkyladamantane-2-yl group, a 1-(adamantane-1-yl)alkane-1-yl group, a norbornyl group, a methylnorbornyl group, and an isobornyl group.

When the divalent hydrocarbon group is formed by bonding $R^{a10}$ and $R^{a11}$, examples of —C($R^{a10}$) ($R^{a11}$) ($R^{a12}$) include the following ones;

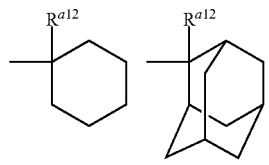

where $R^{a12}$ is as defined above.

Examples of the monomer from which the structural unit represented by formula (a1-3) is derived include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin has a structural unit represented by formula (a1-3), the photoresist composition having excellent resolution and higher dry-etching resistance tends to be obtained.

When Resin (A) comprises the structural unit represented by formula (a1-3), the content of the structural unit is usually 10 to 95% by mole and preferably 15 to 90% by mole and more preferably 20 to 85% by mole based on total molar of all the structural units of the resin.

Other examples of the structural unit (a) having a group represented by formula (2) include one represented by formula (a1-4):

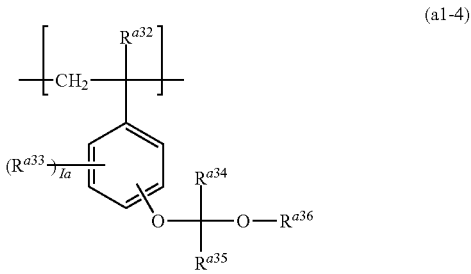

(a1-4)

wherein $R^{a32}$ represents a hydrogen atom, a halogen atom, a C1-C6 alkyl group or a C1-C6 halogenated alkyl group, $R^{a33}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, $1^{a}$ represents an integer of 0 to 4, $R^{a34}$ and $R^{a35}$ each independently represent a hydrogen atom or a C1-C12 hydrocarbon group, $R^{a36}$ represents a C1-C20 aliphatic hydrocarbon group in which a methylene group can be replaced by —O— or —S—, and $R^{a35}$ and $R^{a36}$ are bonded to each other to jointly represent a C2-C20 divalent hydrocarbon group in which a methylene group can be replaced by —O— or —S—.

Examples of the alkyl group represented by $R^{a32}$ and $R^{a33}$ include a methyl group, an ethyl group, a propyl group, a butyl group, a pentyl group, and a hexyl group, preferably a C1-C4 alkyl group, more preferably a methyl group and an ethyl group, and still more preferably a methyl group.

Examples of the alkoxy group represented by $R^{a33}$ include a methoxy group, an ethoxy group, a propoxy group, an isopropoxy group, a butoxy group, an isobutoxy group, a sec-butoxy group, a tert-butoxy group, a pentyloxy group and a hexyloxy group. Examples of the acyl group represented by $R^{a33}$ include an acetyl group, a propyonyl group and a butyryl group, and examples of the acyloxy group represented by $R^{a33}$ include an acetyloxy group, a propyonyloxy group and a butyryloxy group.

Examples of halogen atom represented by $R^{a32}$ and $R^{a33}$ include a fluorine atom, a chlorine atom, and a bromine atom.

Examples of the groups represented by $R^{a34}$ and $R^{a35}$ include those as referred to for $R^{a1'}$ and $R^{2'}$.

Examples of the groups represented by $R^{36}$ include those as referred to for $R^{a3'}$.

$R^{a32}$ preferably represents a hydrogen atom.

$R^{a33}$ is preferably a C1-C4 alkoxy group, more preferably a methoxy group and an ethoxy group, and still more preferably a methoxy group.

The symbol "1a" preferably represents 0 or 1, more preferably 1.

$R^{a34}$ preferably represents a hydrogen atom.

$R^{a35}$ is preferably a C1-C12 monovalent hydrocarbon group, more preferably a methyl group and an ethyl group.

The hydrocarbon group represented by $R^{a36}$ includes a C1-C18 alkyl group, a C3-C18 monovalent alicyclic hydrocarbon group, a C6-C18 monovalent aromatic hydrocarbon group, and any combination of them, and preferably a C1-C18 alkyl group, a C3-C18 monovalent alicyclic hydrocarbon group and a C7-C18 aralkyl group. These groups may be unsubstituted or substituted. The alkyl group and the monovalent alicyclic hydrocarbon group are preferably unsubstituted. As the substituent for the monovalent aromatic hydrocarbon group, a $C6-C_{10}$ aryloxy group is preferred.

Examples of the monomer from which the structural unit (a1-4) is derived include monomers recited in JP2010-204646A1. Among them, the monomers represented by formulae (a1-4-1), (a1-4-2), (a1-4-3), (a1-4-4), (a1-4-5), (a1-4-6) and (a1-4-7) are preferred, and the monomers represented by formulae (a1-4-1), (a1-4-2), (a1-4-3), (a1-4-4) and (a1-4-5) are more preferred.

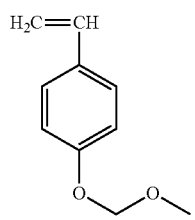

(a1-4-1)

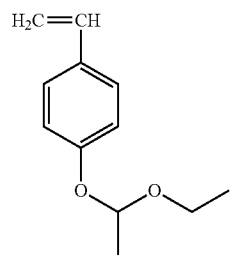

(a1-4-2)

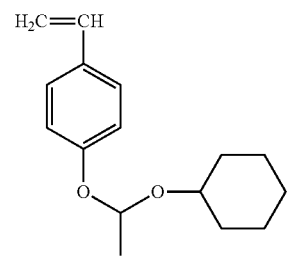

(a1-4-3)

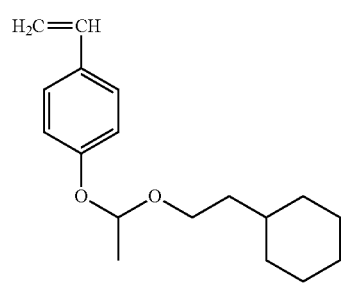

(a1-4-4)

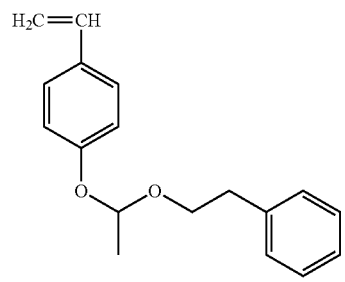

(a1-4-5)

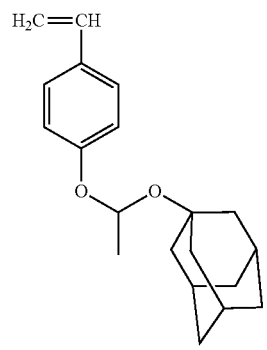

(a1-4-6)

-continued (a1-4-7)

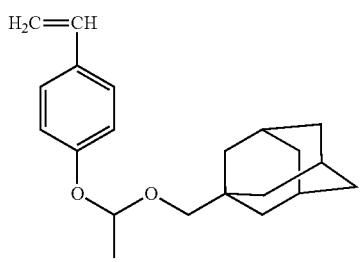

When Resin (A) comprises a structural unit represented by formula (a1-4), its content is usually 10 to 95% by mole, preferably 15 to 90% by mole and more preferably 20 to 85% by mole based on 100% by mole of all the structural units of the resin.

Other examples of the structural unit having an acid-labile group include one represented by formula (a1-5):

(a1-5)

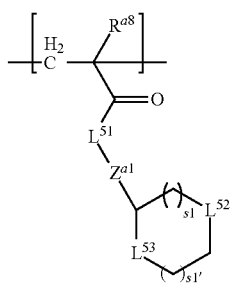

In formula (I-5), $R^{a8}$ represents a hydrogen atom, a halogen atom, or a C1-C6 alkyl group which may have a halogen atom, $Z^{a1}$ represents a single bond or *—$(CH_2)_{k3}$—CO— $L^{54}$- in which k1 represents an integer of 1 to 4 and * represents a binding site to $L^{54}$, $L^{51}$, $L^{52}$, $L^{53}$ and $L^{54}$ each independently represent an oxygen atom or a sulfur atom, s1 represents an integer of 1 to 3, and s1' represents an integer of 0 to 3.

Herein, the structural unit represented by formula (a-5) is sometimes referred to as "structural unit (a-5)".

Examples of halogen atoms include a fluorine atom and chlorine atom, preferably a fluorine atom.

Examples of the alkyl group which may have a halogen atom include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group, a fluoromethyl group, and a trifluoromethyl group.

In the formula (a-5), $R^{a8}$ preferably represents a hydrogen atom, a methyl group, or trifluoromethyl group.

$L^{51}$ represents preferably an oxygen atom.

It is preferred that one of $L^{52}$ and $L^{53}$ represents an oxygen atom, while the other represents a sulfur atom.

s1 preferably represents 1. s1' represents an integer of 0 to 2.

$Z^{a1}$ preferably represents a single bond or *—$CH_2$—CO—O— wherein * represents a binding site to $L^{51}$.

Examples of the monomer from which the structural unit (a-5) is derived include the following ones:

(a1-5-1)

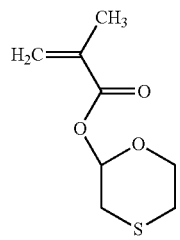

(a1-5-2)

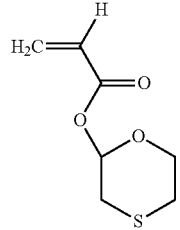

(a1-5-3)

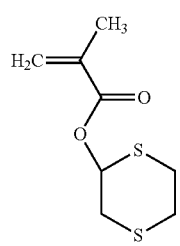

(a1-5-4)

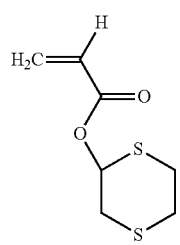

When Resin (A) comprises a structural unit (a-5), its content is usually 1 to 50% by mole, preferably 3 to 45% by mole and more preferably 5 to 40% by mole based on 100% by mole of all the structural units of the resin.

Resin (A) comprises preferably one or more of the structural units (a-0), (a-1), (a-2) and (a-5), more preferably two or more of the structural units (a-1), (a-2) and (a-5).

Specifically, it comprises preferably the structural units (a-1) and (a-2), the structural units (a-1) and (a-5), the structural units (a-1) and (a-0), the structural units (a-5) and (a-0), the structural units (a-0), (a-1) and (a-2), or the structural units (a-0), (a-1) and (a-5), more preferably the structural units (a-1) and (a-2) or the structural units (a-1) and (a-5).

Resin (A) comprises preferably the structural unit (a-1).

The content of the structural unit having an acid-labile group is usually 10 to 80% by mole and preferably 20 to 60% by mole, based on total molar of all the structural units of Resin (A).

As to a monomer having no acid-labile group, monomers which have been known to in the art can be used as such monomer, and they are not limited to any specific one provided that it has no acid-labile group.

The structural unit having no acid-labile group preferably has a hydroxyl group or a lactone ring. When the resin comprises the structural unit derived from the monomer having no acid-labile group and having a hydroxyl group or a lactone ring, a photoresist composition capable of providing a photoresist film with good resolution and adhesiveness of photoresist to a substrate can be obtained.

Hereinafter, the structural unit having no acid-labile group and having a hydroxy group is referred to as "structural unit (a2)", and the structural unit having no acid-labile group and having a lactone ring is referred to as "structural unit (a3)".

The hydroxy group which the structural unit (a2) has may be an alcoholic hydroxy group or a phenolic hydroxy group.

When KrF excimer laser (wavelength: 248 nm) lithography system, or a high energy laser such as electron beam and extreme ultraviolet is used as an exposure system, the resin which comprises the structural unit (a2) having a phenolic hydroxy group is preferred. When ArF excimer laser (wavelength: 193 nm) is used as an exposure system, the resin which comprises the structural unit (a2) having an alcoholic hydroxy group is preferred and the resin which comprises the structural unit (a2-1) described later is more preferred.

Resin (A) may comprise one or more of the structural units (a2).

Examples of the structural unit (a2) having a phenolic hydroxy group include one represented by formula (a2-0):

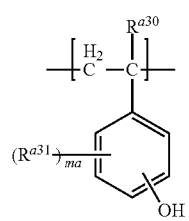

(a2-0)

In formula (a2-0), $R^{a30}$ represents a hydrogen atom, a halogen atom, a C1-C6 alkyl group or a C1-C6 halogenated alkyl group, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, In the formula (a2-0), examples of the halogen atom include a fluorine atom, a chlorine atom, a bromine atom or iodine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferred and a C1-C2 alkyl group is more preferred and a methyl group is especially preferred. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferred and a C1-C2 alkoxy group is more preferred and a methoxy group is especially preferred. Examples of the C2-C4 acyl group include an acetyl group, a propyonyl group and a butyryl group, and examples of the C2-C4 acyloxy group include an acetyloxy group, a propyonyloxy group and a butyryloxy group.

In the formula (a2-0), ma is preferably 0, 1 or 2, and is more preferably 0 or 1, and especially preferably 0.

Examples of the monomer from which the structural unit (a2-0) is derived include compounds mentioned in JP2010-204634A. Among them, the structural units represented by formulae (a2-0-1), (a2-0-2), (a2-0-3) and (a2-0-4) are preferred as the structural unit (a2-0), and those represented by formulae (a2-0-1) and (a2-0-2) are more preferred.

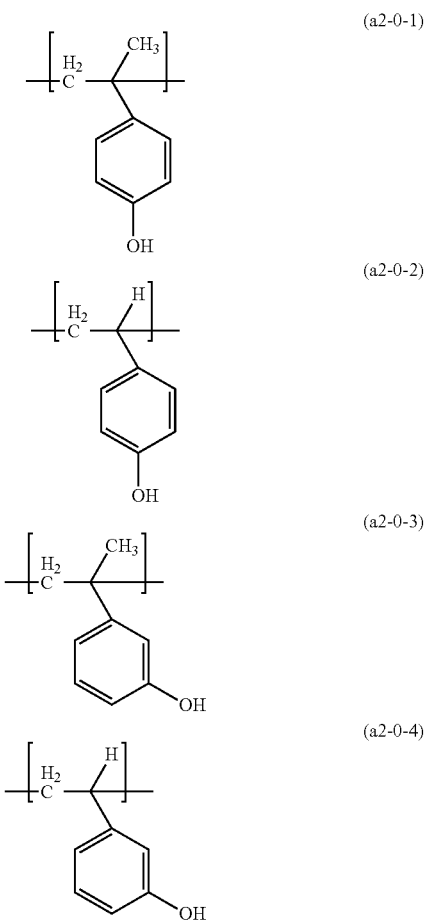

Resin (A) which comprises a structural unit represented by formula (a2-0) can be produced, for example, by polymerizing a monomer where its phenolic hydroxyl group has been protected with a suitable protecting group, followed by deprotection. Examples of the protecting group for a phenolic hydroxyl group include an acetyl group.

When Resin (A) comprises the structural unit represented by formula (a2-0), its content is usually 5 to 95% by mole and preferably 10 to 85% by mole and more preferably 15 to 80% by mole based on total molar of all the structural units of the resin.

Examples of the structural unit (a2) having an alcoholic hydroxy group include one represented by formula (a2-1):

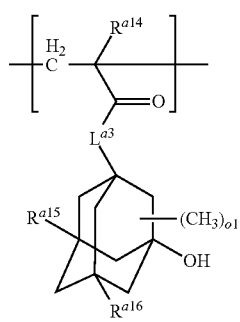
(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding site to —CO—, and k2 represents an integer of 1 to 7, and o1 represents an integer of 0 to 10.

Hereinafter, the structural unit represented by formula (a2-1) is referred to as "structural unit (a2-1)".

In the formula (a2-1), $R^{a14}$ is preferably a methyl group. $R^{a15}$ is preferably a hydrogen atom. $R^{a16}$ is preferably a hydrogen atom or a hydroxyl group. $L^{a3}$ is preferably *—O— or *—O—$(CH_2)_{f2}$—CO—O— in which * represents a binding site to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

Examples of monomers from which the structural unit (a2-1) is derived include compounds mentioned in JP2010-204646A.

Preferred examples of the monomer from which the structural unit (a2-1) is derived include those represented by formulae (a2-1-6)

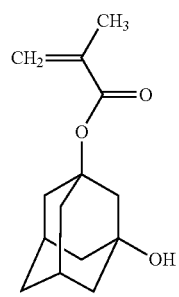
(a2-1-1)

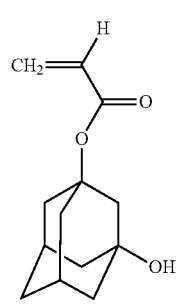
(a2-1-2)

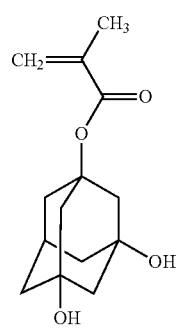
(a2-1-3)

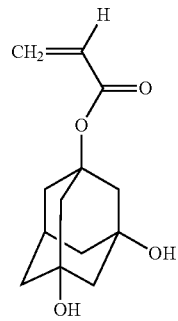
(a2-1-4)

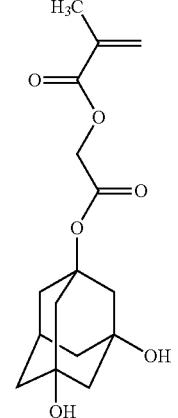
(a2-1-5)

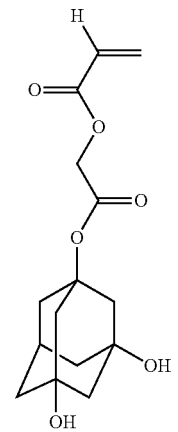
(a2-1-6)

Among them, more preferred are the monomer represented by formulae (a2-1-1), (a2-1-2), (a2-1-3) and (a2-1-4), still more preferred are the monomer represented by formulae (a2-1-1) and (a2-1-3).

When Resin (A) comprises the structural unit (a2-1), its content is usually 1 to 45% by mole, preferably 1 to 40% by mole, and more preferably 1 to 35% by mole, and especially preferably 2 to 20% by mole, based on total molar of all the structural units of the resin.

Examples of the lactone ring of the structural unit (a3) include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the structural unit (a3) include the monomers represented by formulae (a3-1), (a3-2), (a3-3) and (a3-4);

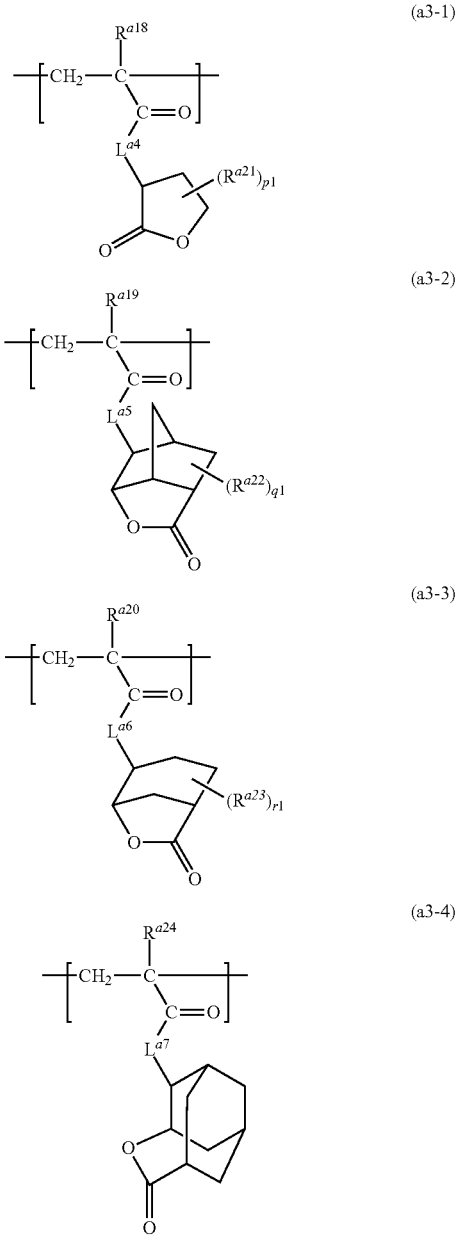

In formulae, $L^{a4}$, $L^{a5}$ and $L^{a6}$ each independently represent *—O— or *—O—$(CH_2)_{k3}$—CO—O— in which * represents a binding site to —CO— and k3 represents an integer of 1 to 7, $R^{a18}$, $R^{a19}$ and $R^{a20}$ each independently represent a hydrogen atom or a methyl group, $R^{a21}$ represents a C1-C4 monovalent aliphatic hydrocarbon group, $R^{a22}$ and $R^{a23}$ are independently in each occurrence a carboxyl group, a cyano group or a C1-C4 monovalent aliphatic hydrocarbon group, $R^{a24}$ each independently represent a hydrogen atom, a halogen atom, or a C1-C6 alkyl group which may have a halogen atom, $L^{a7}$ represents a single bond, $*^1$-$L^{a8}$-O—, $*^1$-$L^{a8}$-CO—O—, $*^1$-$L^{a8}$-CO—O-$L^{a9}$-CO—O— or $*^1$-$L^{a8}$-CO—O-$L^{a9}$-O— in which $L^{a8}$ and $L^{a9}$ each independently represent C1-C6 divalent alkanediyl group, $*^1$ represents a binding site to —O—, and p1 represents an integer of 0 to 5, q1 and r1 independently each represent an integer of 0 to 3.

Examples of halogen atom represented by $R^{a24}$ include a fluorine atom, a chlorine atom, a bromine atom and an iodine atom.

Examples of the alkyl group represented by $R^{a24}$ include a methyl group, an ethyl group, a propyl group, a butyl group, a pentyl group, and a hexyl group, preferably a C1-C4 alkyl group, and more preferably a methyl group and an ethyl group.

As to $R^{a24}$, examples of the alkyl group which has an halogen atom include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a trichloromethyl group, a tribromomethyl group, and a triiodomethyl group.

As to $L^{a8}$ and $L^{a9}$, examples of the alkanediyl group include a methylene group, an ethylene group, a propane-1,3-diyl group, a butane-1,4-diyl group, a pentane-1,5-diyl group and a hexane-1,6-diyl group, a butane-1,3-diyl group, 2-methylpropane-1,3-diyl group, a 2-methylpropane-1,2-diyl group, a pentane-1,4-diyl group and a 2-methylbutane-1,4-diyl group.

It is preferred that $L^{a4}$, $L^{a5}$ and $L^{a6}$ each independently represent *—O— or *—O—$(CH_2)_{d1}$—CO—O— in which * represents a binding site to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group.

It is preferred that p1, q1 and r1 each independently represent an integer of 0 to 2, and it is more preferred that p1, q1 and r1 each independently represent 0 or 1.

$R^{a24}$ is preferably a hydrogen atom or a C1-C4 alkyl group, more preferably a hydrogen atom, a methyl group or an ethyl group, and still more preferably a hydrogen atom or a methyl group.

$L^{a7}$ represents preferably a single bond or $*^1$-$L^{a8}$-CO—O—, more preferably a single bond, $*^1$—$CH_2$—CO—O— or $*^1$—$C_2H_4$—CO—O—.

Examples of the monomer from which the structural unit (a3) is derived include those mentioned in JP2010-204646A, JP2000-122294A and JP2012-41274A. As the structural unit (a3), preferred are those represented by formulae (a3-1-1) to (a3-1-4), the formulae (a3-2-1) to (a3-2-4), the formulae (a3-3-1) to (a3-3-4) and the formulae (a3-4-1) to (a3-4-6), more preferred are those represented by formulae (a3-1-1), (a3-1-2), (a3-2-3) and (a3-2-4), and still more preferred are those represented by formulae (a3-1-1) and (a3-2-3).
(a3-1-1)
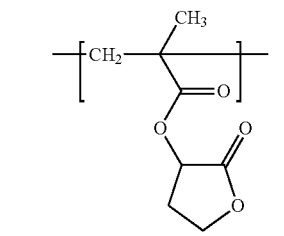
(a3-1-2)
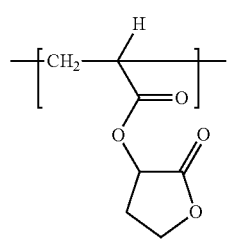
(a3-1-3)
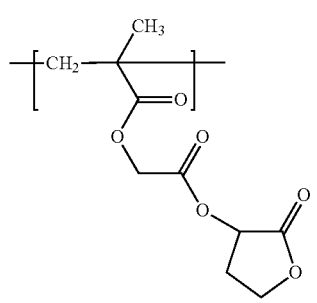
(a3-1-4)
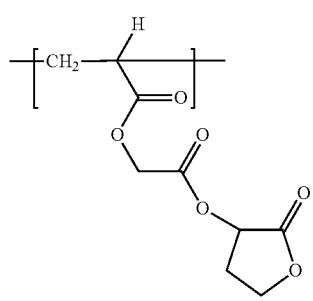
(a3-2-1)
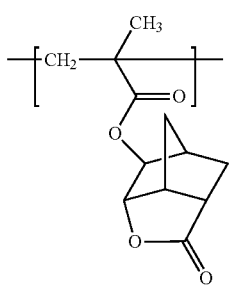
(a3-2-2)
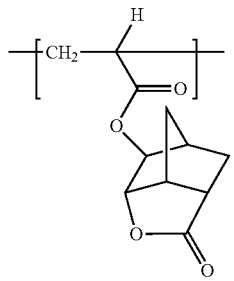
(a3-2-3)
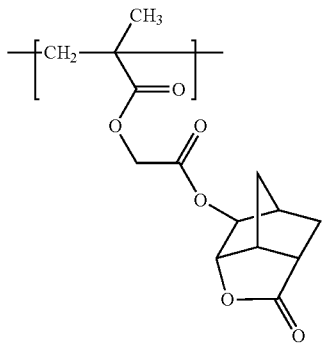
(a3-2-4)
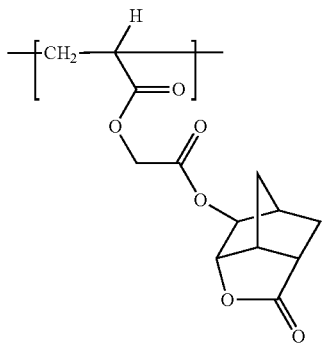
(a3-3-1)
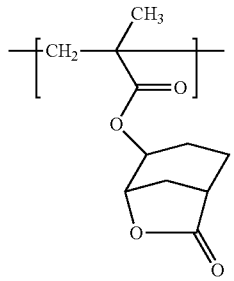
(a3-3-2)
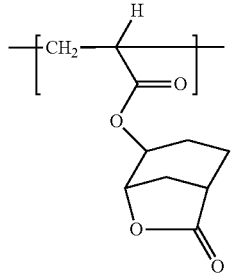

(a3-3-3)
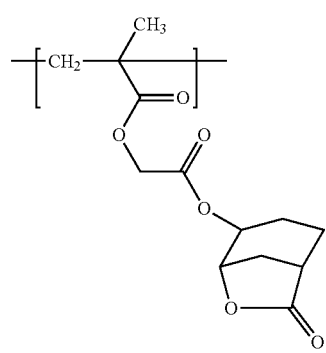
(a3-3-4)
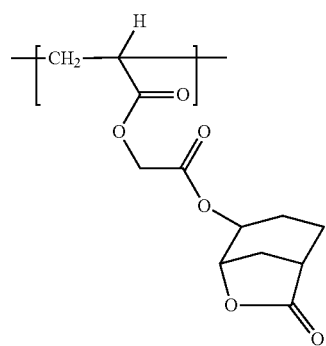
(a3-4-1)
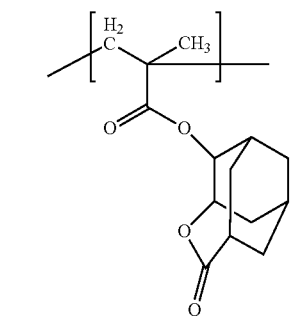
(a3-4-2)
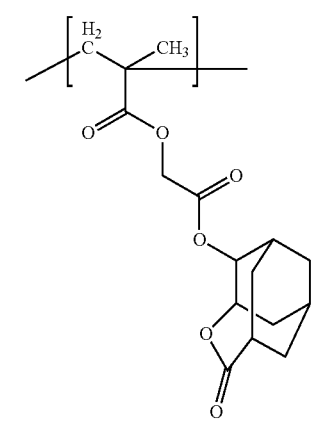
(a3-4-3)
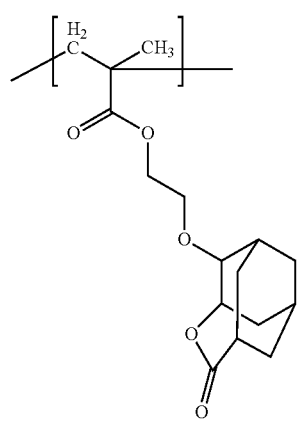
(a3-4-4)
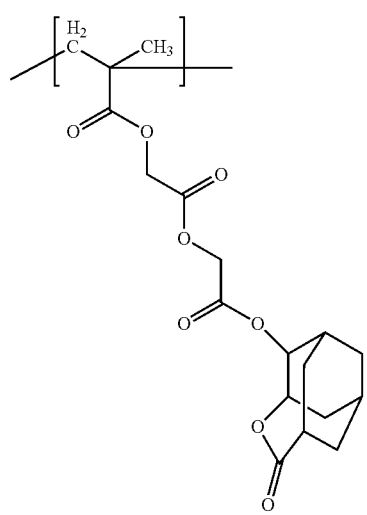
(a3-4-5)
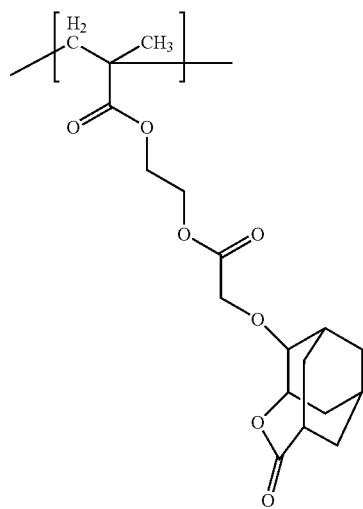

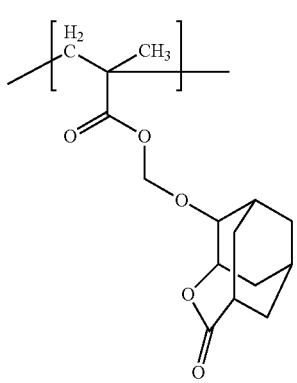
(a3-4-6)

Specific examples of the structural unit (a3) include those where methyl groups of formulae (a3-4-1) to (a3-4-6) are replaced by hydrogen atoms.

When Resin (A) comprises the structural unit (a3), its content thereof is preferably 5 to 70% by mole, and more preferably 10 to 65% by mole and more preferably 10 to 60% by mole, based on total molar of all the structural units of the resin.

When Resin (A) comprises the structural unit represented by formula (a3-1), (a3-2), (a3-3) or (a3-4), the total content of them is preferably 5 to 60% by mole, and more preferably 5 to 50% by mole and more preferably 10 to 50% by mole, based on total molar of all the structural units of the resin.

Examples of another structural unit having no acid-labile group include a structural unit having a fluorine atom and a structural unit which has a hydrocarbon not being removed therefrom by action of an acid.

Examples of the structural unit having a fluorine atom include the following one.

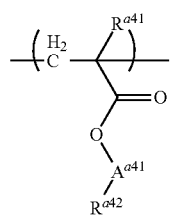
(a4-1)

In formula (a4-1), $R^{a41}$ represents a hydrogen atom or a methyl group; $A^{a41}$ represents a single bond or a C1-C6 divalent alkanediyl group where a methylene group can be replaced by a carbonyl group or an oxygen atom; and $A^{a42}$ represents a C1-C20 fluorine-containing saturated hydrocarbon group, preferably a C1-C10 saturated perfluorohydrocarbon group, more preferably C1-C6 perfluoroalkyl group. Examples of $A^{a41}$ include a single bond, —CH$_2$—, —CH$_2$—CH$_2$—, —CH$_2$—CH$_2$—CH$_2$—, —CH$_2$—O—CO— and —CH$_2$—CH$_2$—O—CO—. Examples of $A^{a42}$ include a C1-C20 fluoroalkyl group such as a fluoromethyl group, a fluoroethyl group, a fluoropropyl group, a fluorobutyl group, a fluoropentyl group, a fluorohexyl group, a perfluoroheptyl group, and a perfluorooctyl group; a C3-C20 fluorocycloalkyl group such as fluorocyclohexyl group; and a C5-C20 fluoropolycyclic hydrocarbon group such as fluoroadamantyl group.

Specific examples of the structural unit having a fluorine atom include the following ones.

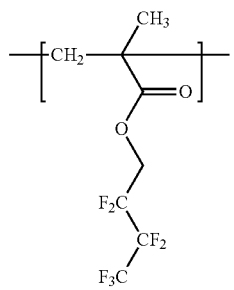
(a4-0-1)

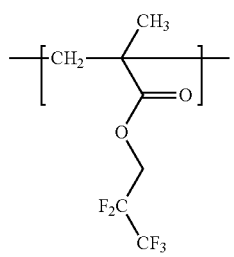
(a4-0-2)

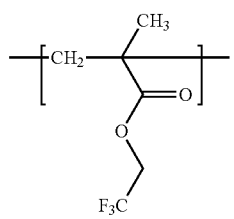
(a4-0-3)

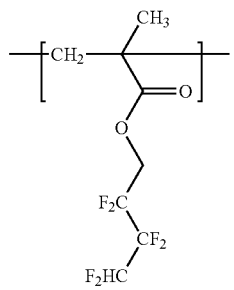
(a4-0-4)

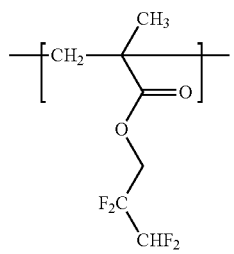
(a4-0-5)

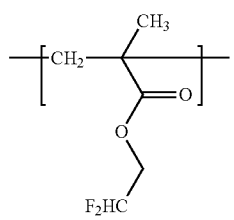
(a4-0-6)

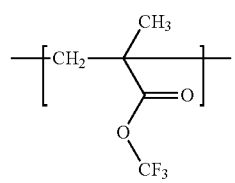 (a4-0-7)
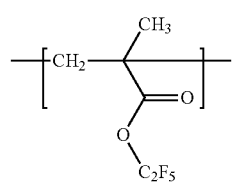 (a4-0-8)
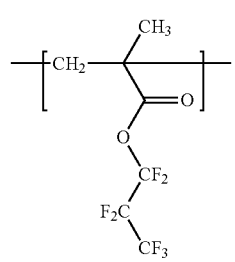 (a4-0-9)
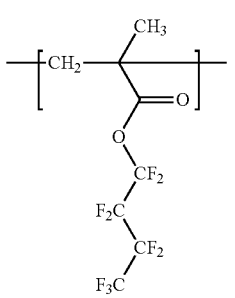 (a4-0-10)
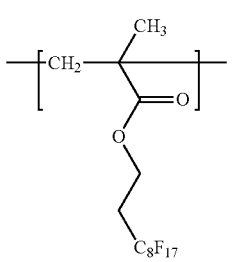 (a4-0-11)
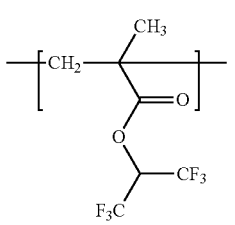 (a4-0-12)
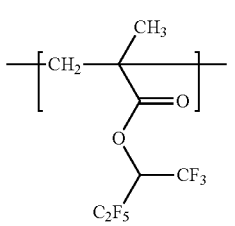 (a4-0-13)
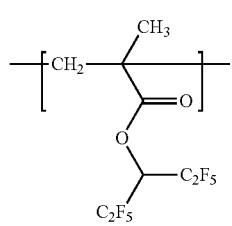 (a4-0-14)
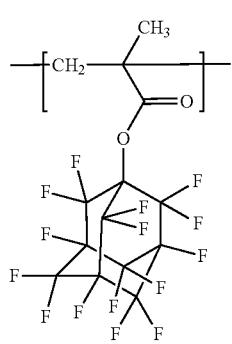 (a4-0-15)
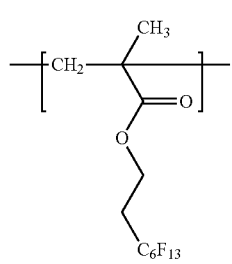 (a4-0-16)
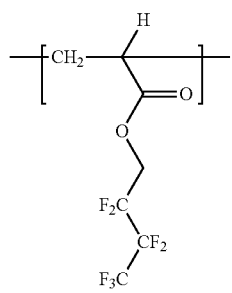 (a4-0-17)
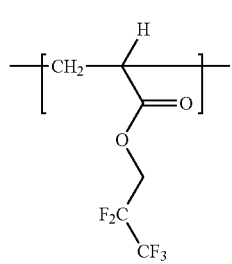 (a4-0-18)
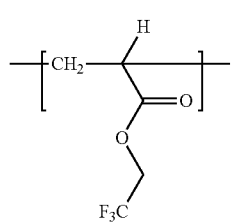 (a4-0-19)

-continued
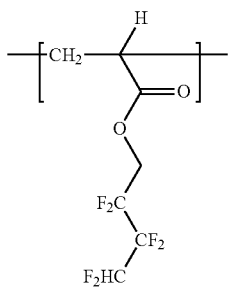 (a4-0-20)
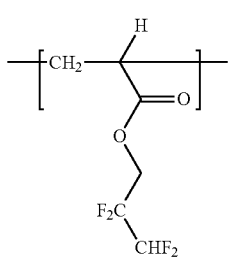 (a4-0-21)
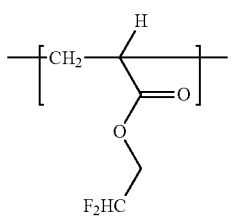 (a4-0-22)
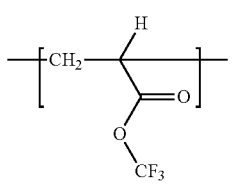 (a4-0-23)
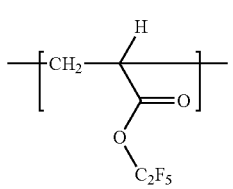 (a4-0-24)
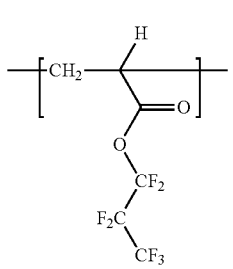 (a4-0-25)
-continued
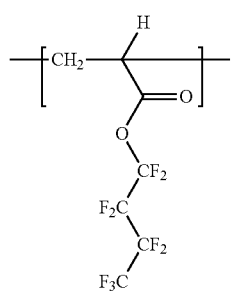 (a4-0-26)
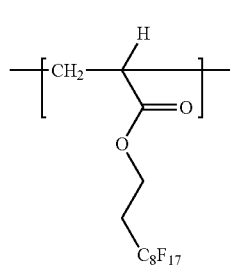 (a4-0-27)
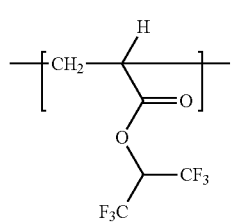 (a4-0-28)
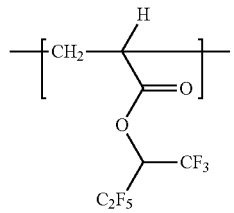 (a4-0-29)
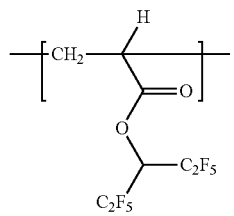 (a4-0-30)
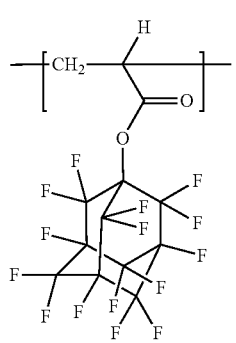 (a4-0-31)

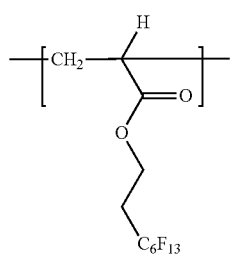
(a4-0-32)
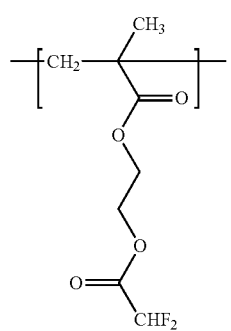
(a4-1-1)
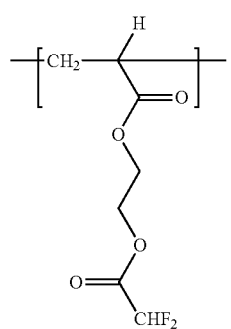
(a4-1-2)
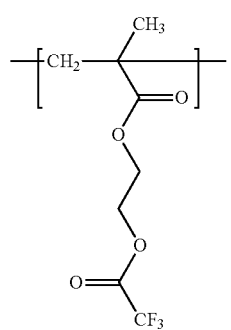
(a4-1-3)
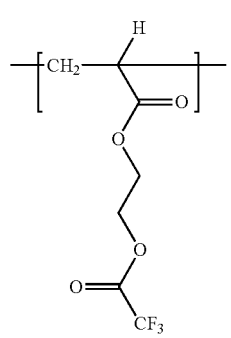
(a4-1-4)
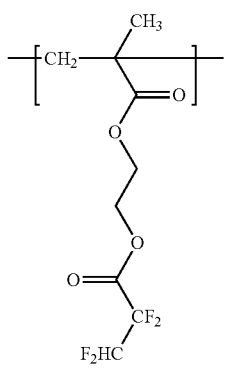
(a4-1-5)
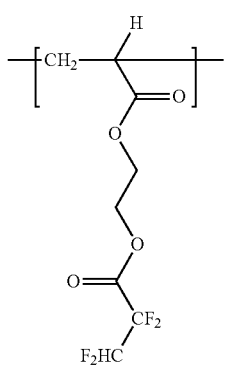
(a4-1-6)
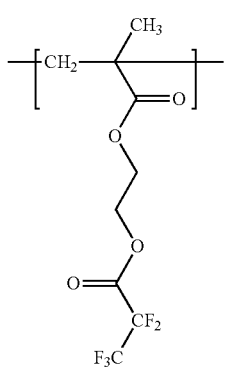
(a4-1-7)
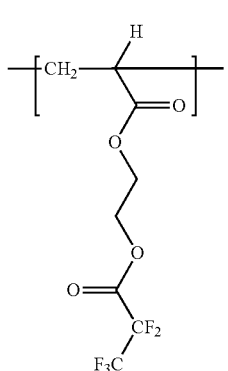
(a4-1-8)

(a4-1-9)
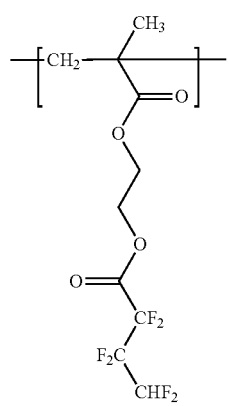
(a4-1-10)
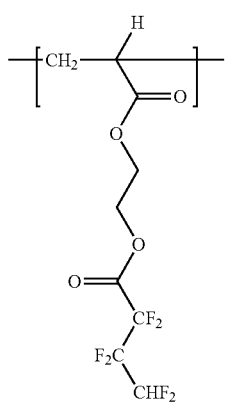
(a4-1-11)
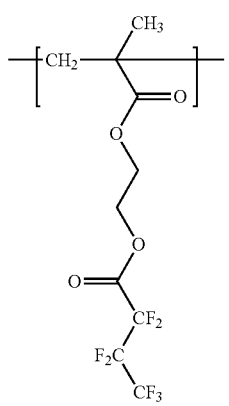
(a4-1-12)
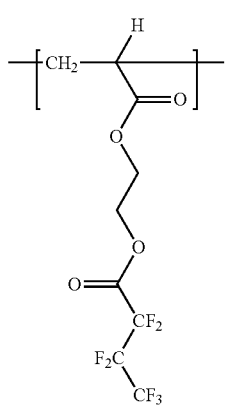
(a4-1-13)
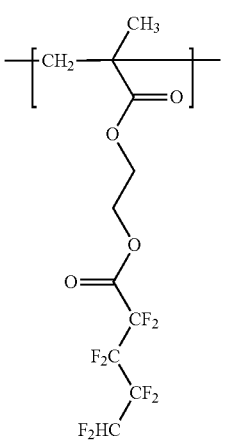
(a4-1-14)
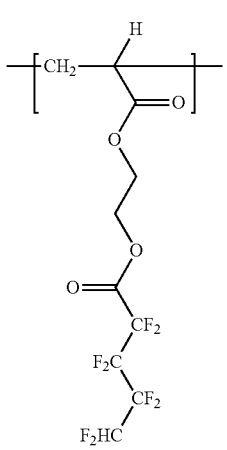
(a4-1-15)
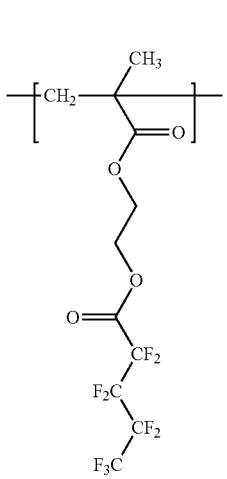

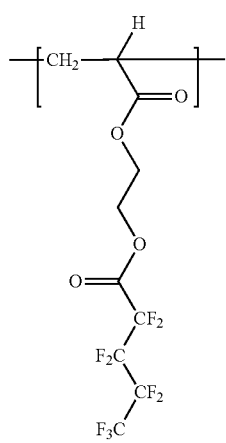 (a4-1-16)
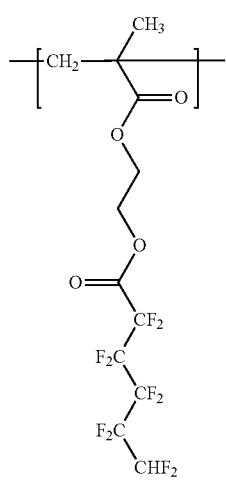 (a4-1-17)
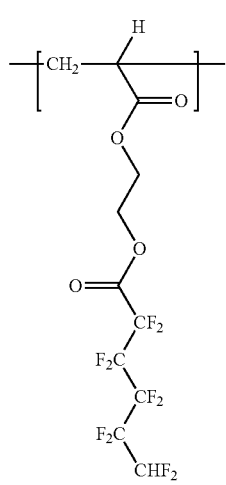 (a4-1-18)
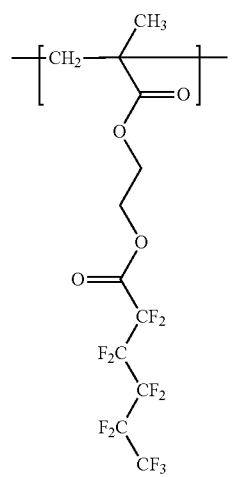 (a4-1-19)
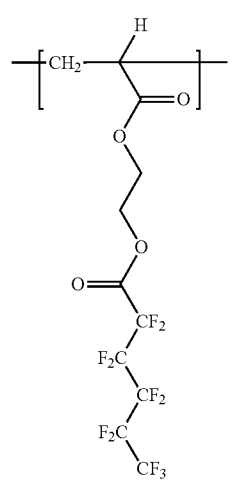 (a4-1-20)
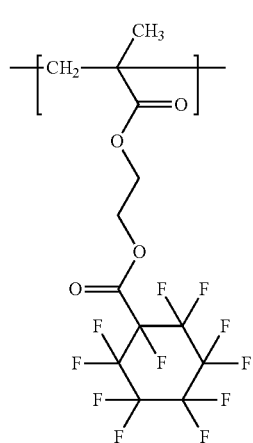 (a4-1-21)

(a4-1-22)
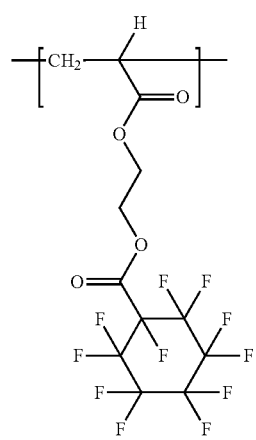
(a4-1'-1)
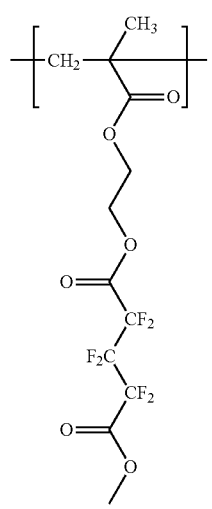
(a4-1'-2)
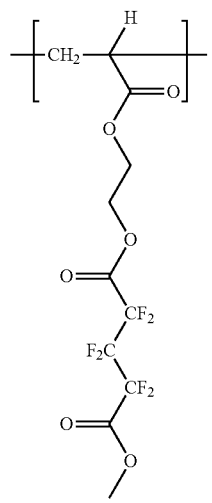
(a4-1'-3)
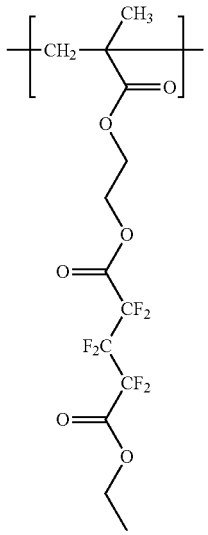
(a4-1'-4)
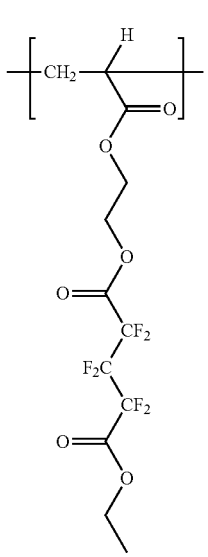
(a4-1'-5)
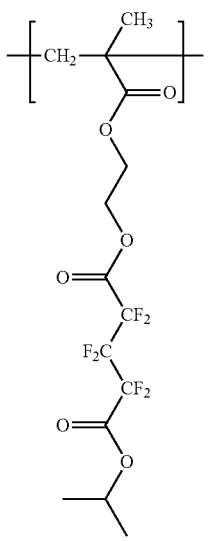

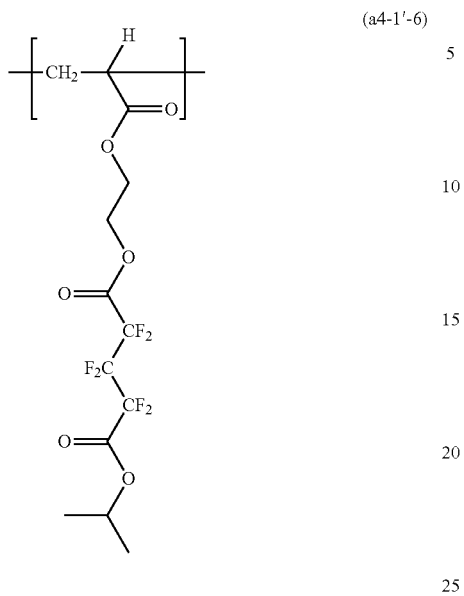
(a4-1'-6)
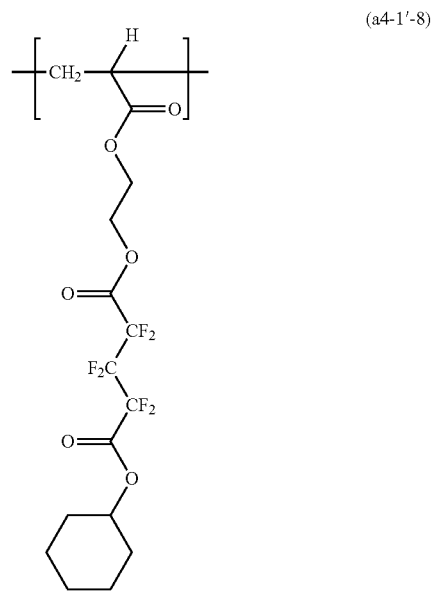
(a4-1'-8)
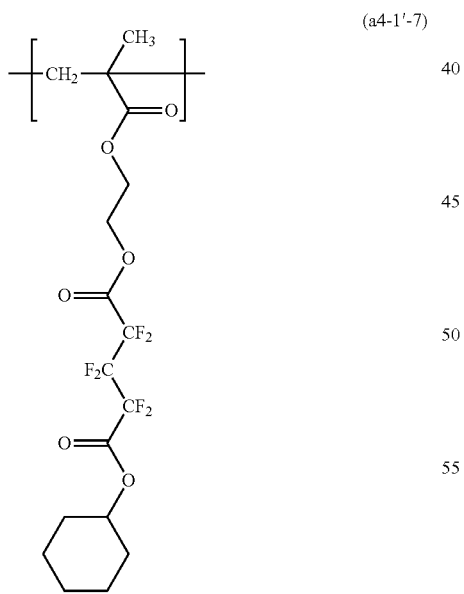
(a4-1'-7)
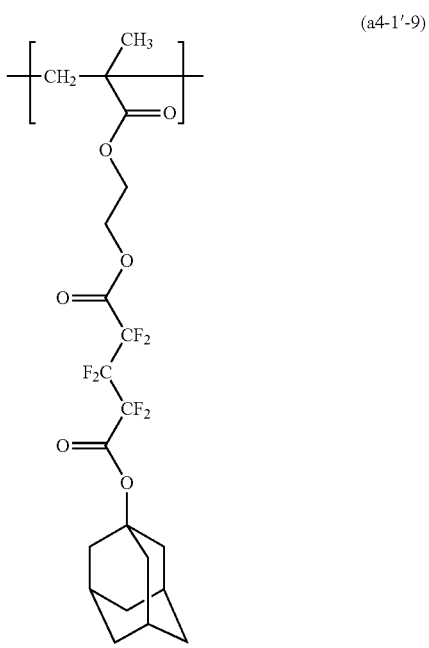
(a4-1'-9)

(a4-1'-10)
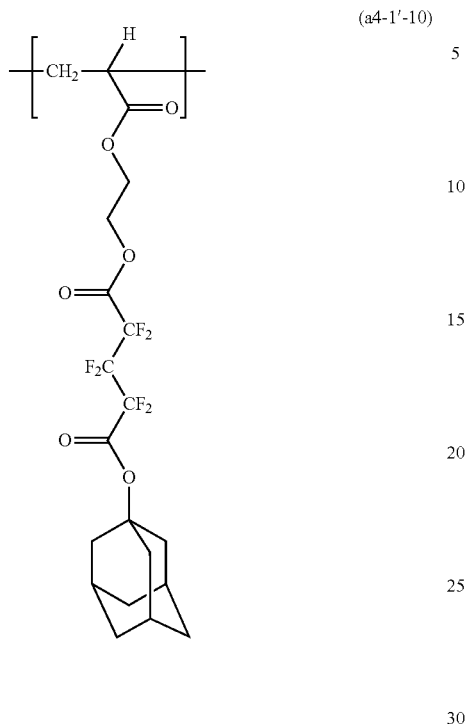
(a4-1'-12)
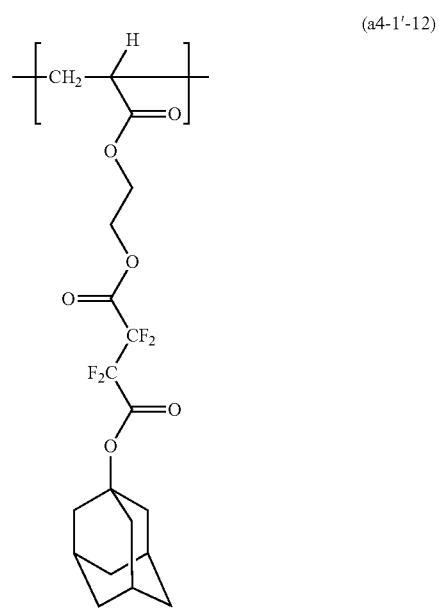
(a4-1'-11)
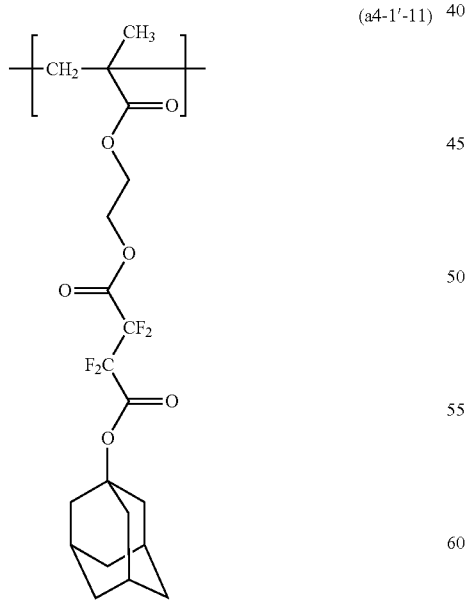
(a4-1'-13)
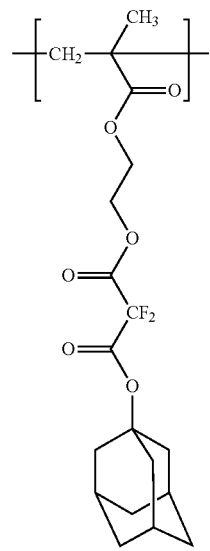

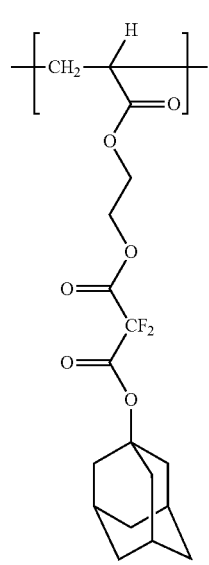
(a4-1'-14)
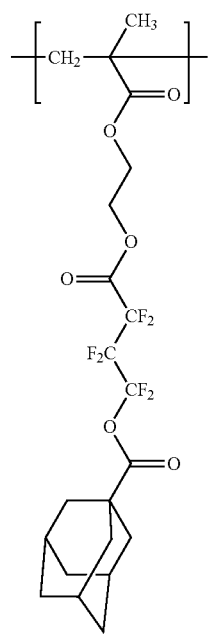
(a4-1'-15)
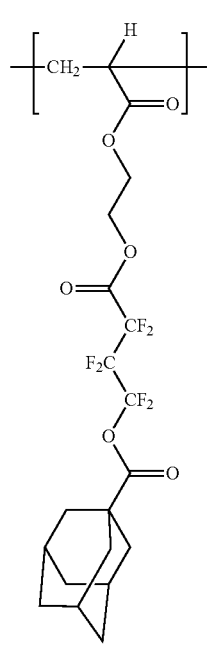
(a4-1'-16)
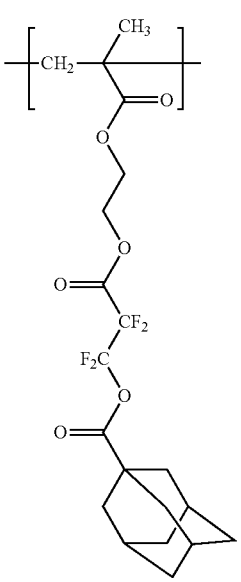
(a4-1'-17)

(a4-1'-18)
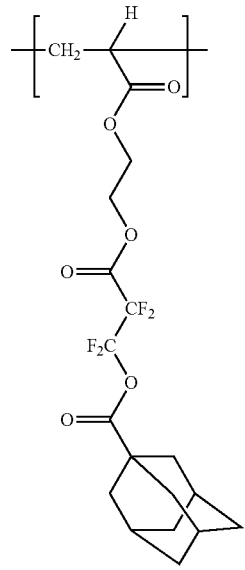
(a4-1'-19)
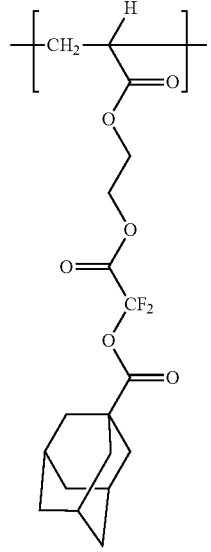
(a4-1'-20)
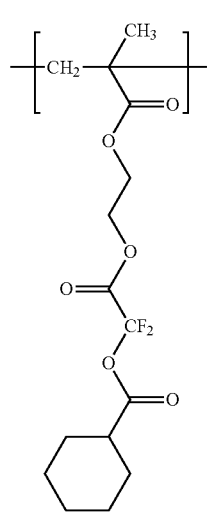
(a4-1'-21)
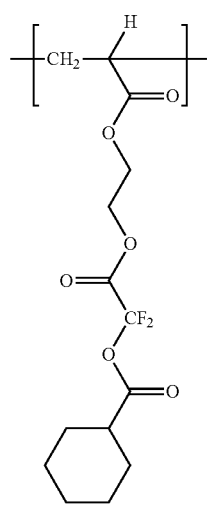
(a4-1'-22)

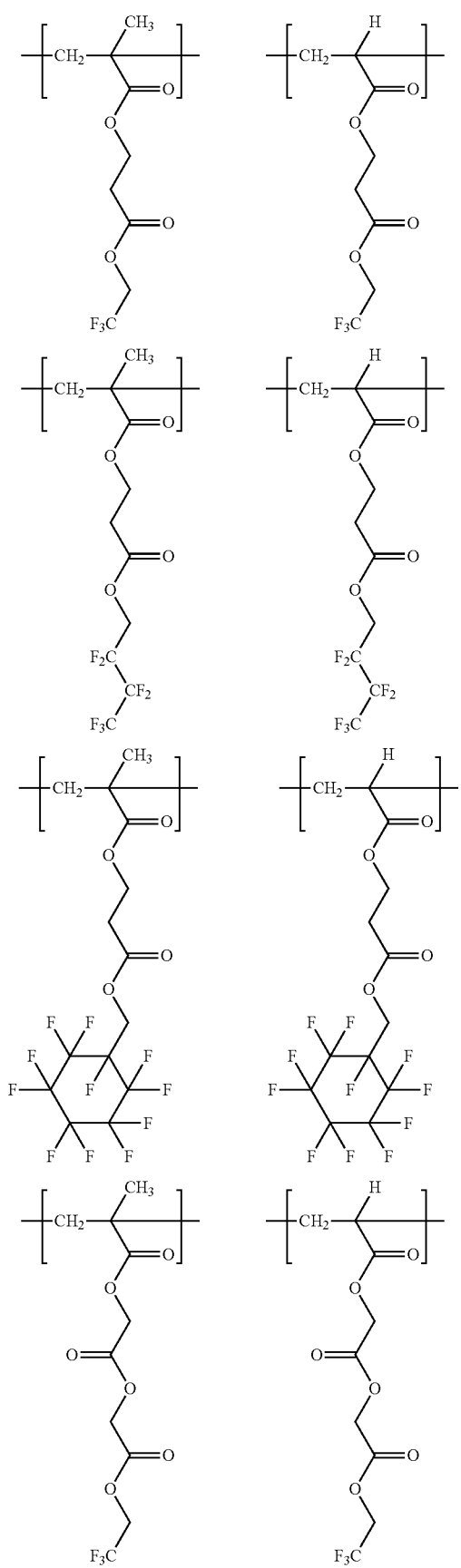
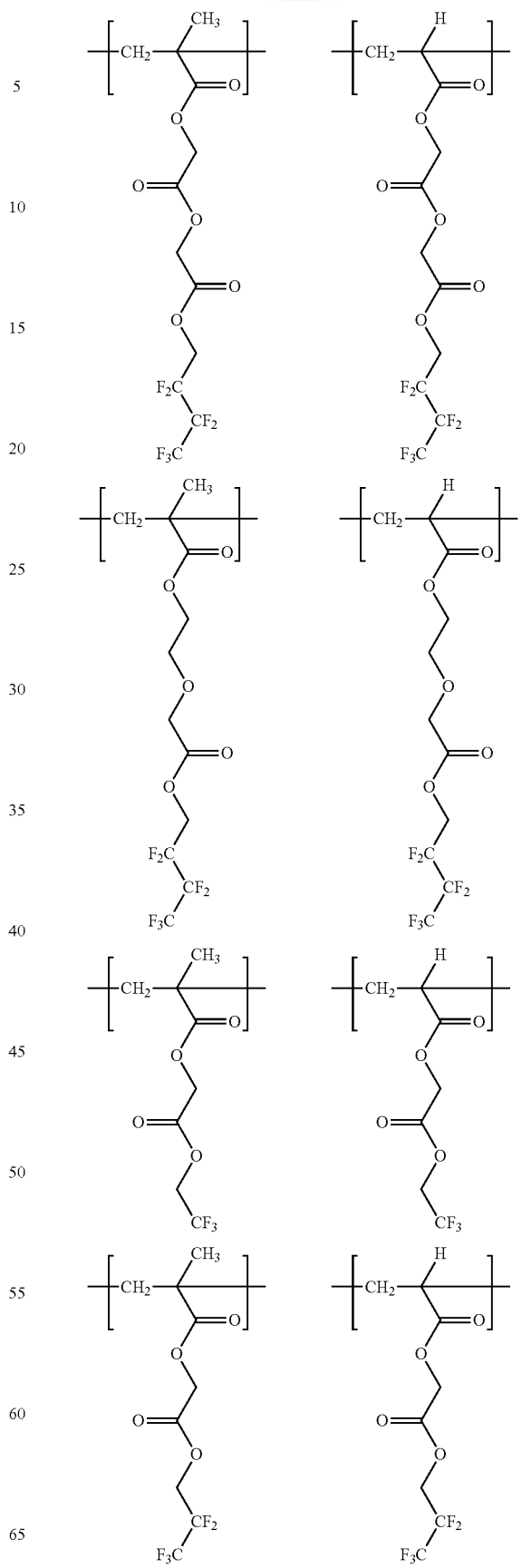

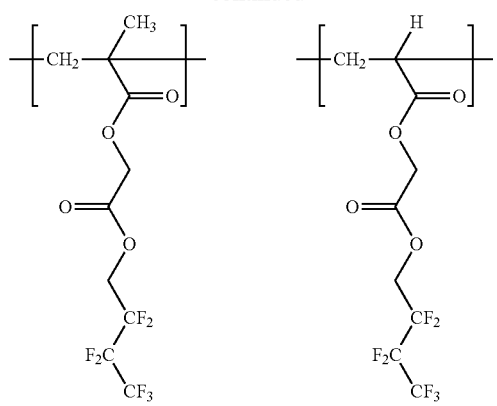
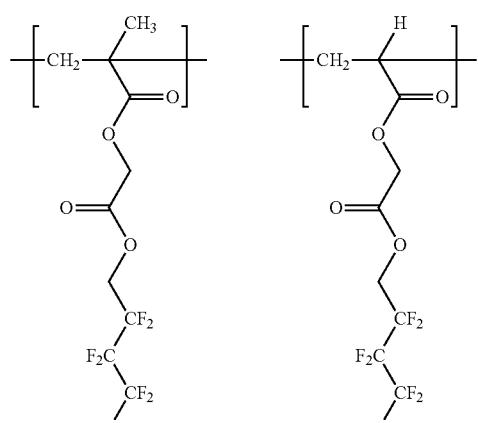
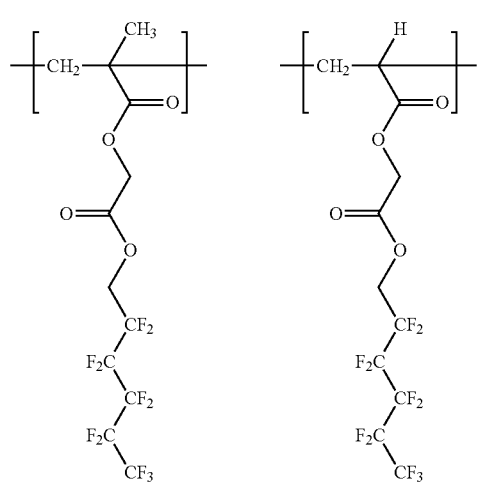
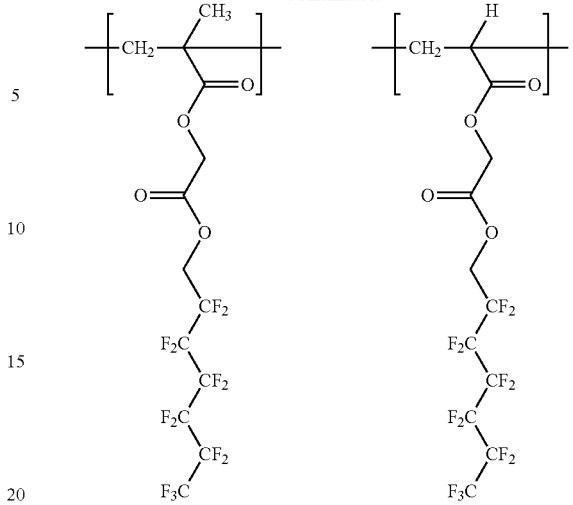

When Resin (A) comprises a structural unit having a fluorine atom, the content thereof is usually 1 to 20% by mole, preferably 2 to 15% by mole, and more preferably 3 to 10% by mole, based on total molar of all the structural units of the resin.

The structural unit which has a hydrocarbon not being removed therefrom by action of an acid may have a linear, branched or cyclic hydrocarbon, preferably an alicyclic hydrocarbon group.

Examples of the structural unit having an acid-stable hydrocarbon group include one represented by formula (a5-1).

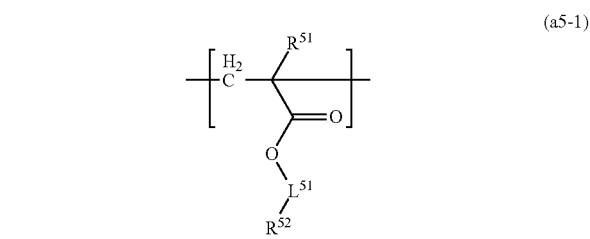

(a5-1)

where $R^{51}$ represents a hydrogen atom or a methyl group;

$R^{52}$ represents a C3-C18 monovalent alicyclic hydrocarbon group, provided that the alicyclic hydrocarbon group has no substituent on the carbon atom bonded to $L^{51}$; and $L^{51}$ represents a single bond or a C1-C8 alkanediyl group where a methylene group can be replaced by an oxygen atom or carbonyl group. The alicyclic hydrocarbon group represented by $R^{52}$ may be monocyclic or polycyclic one. Examples of the alicyclic hydrocarbon group include a monocyclic hydrocarbon group such as a C3-C18 cycloalkyl group (e.g. a cyclopropyl group, a cyclobutyl group, a cyclopentyl group, a cyclohexyl group) and a polycyclic alicyclic hydrocarbon group such as an adamantyl group, or a norbornyl group.

Examples of the alicyclic hydrocarbon group having a substituent include a 3-hydroxyadamantyl group, and a 3-methyladamantyl group.

Specific examples of the structural unit include the following ones.

(a5-1-1)
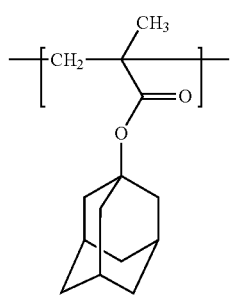
(a5-1-2)
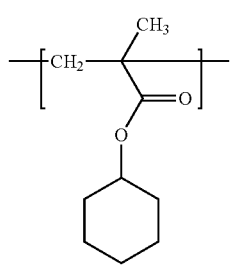
(a5-1-3)
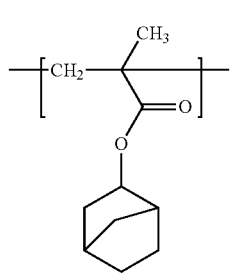
(a5-1-4)
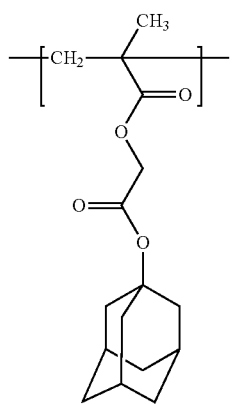
(a5-1-5)
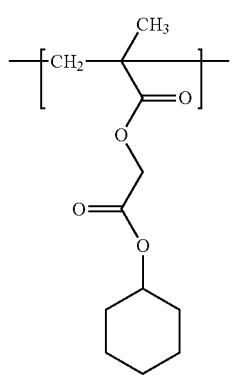
-continued
(a5-1-6)
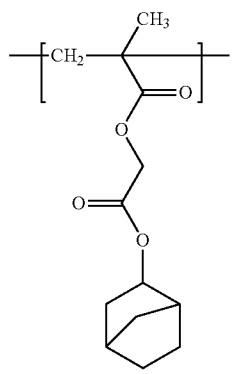
(a5-1-7)
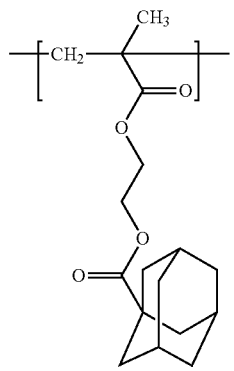
(a5-1-8)
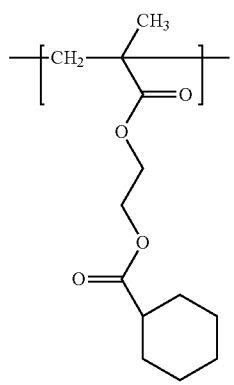
(a5-1-9)
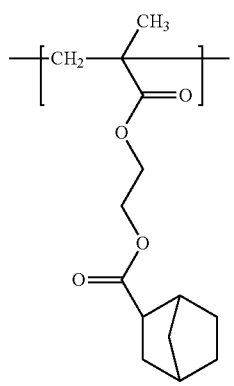

(a5-1-10) 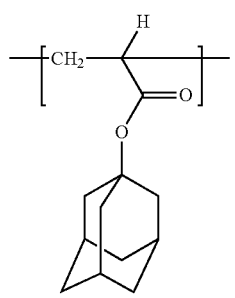
(a5-1-11) 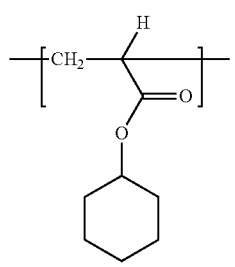
(a5-1-12) 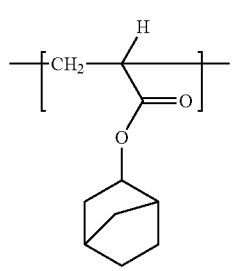
(a5-1-13) 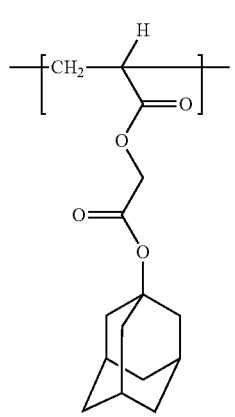
(a5-1-14) 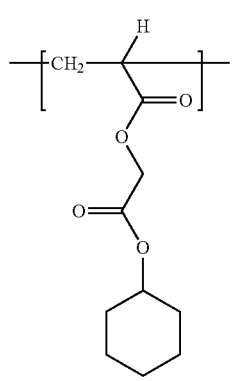
(a5-1-15) 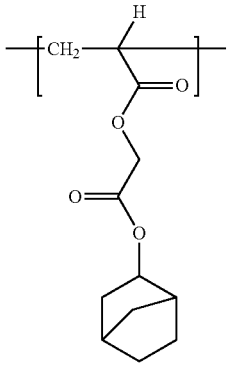
(a5-1-16) 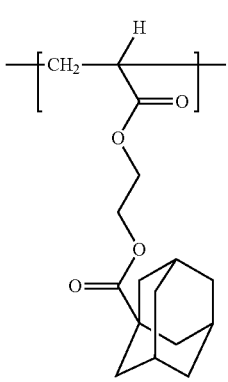
(a5-1-17) 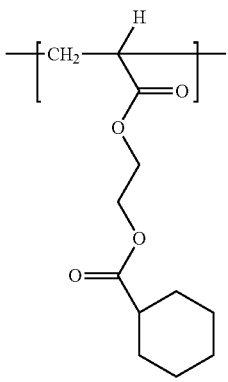
(a5-1-18) 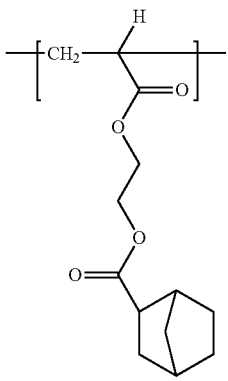
Resin (A) comprises preferably the structural unit (a) and the structural unit having no acid-labile group.
In Resin (A), the structural unit (a1) is one of the structural unit (a1-1) and the structural unit (a1-2), more preferably the structural unit (a1-2). The structural unit (a1-2) is preferably which comprises a cyclohexyl group or a cyclopentyl group.

The structural unit having no acid-labile group is preferably one of the structural unit (a2) and the structural unit (a3). The structural unit (a2) is preferably the structural unit (a2-1). The structural unit (a3) is preferably one of the structural unit (a3-1), the structural unit (a3-2) and the structural unit (a3-4). Resin (A) comprises preferably the structural unit (a) derived from a structural unit having an adamantyl group, preferably structural unit (a1-1). The content of the structural unit having an adamantyl group is preferably 15% by mole or more of the total amount of the structural unit (a). The more is the structural unit having an adamantyl group, the more improved is the resistance of the photoresist film to dry etching.

Resin (A) can be produced according to known polymerization methods such as radical polymerization.

The resin has usually 2,500 or more of the weight-average molecular weight, preferably 2,500 or more of the weight-average molecular weight, more preferably 3,000 or more of the weight-average molecular weight. The resin has usually 50,000 or less of the weight-average molecular weight, preferably more 30,000 or less of the weight-average molecular weight, and preferably more 15,000 or less of the weight-average molecular weight.

The weight-average molecular weight can be measured with gel permeation chromatography.

Examples of another resin than Resin (A) include what consists of structural units having no acid-labile group, preferably what comprises, not the structural unit (a1), but the structural unit having a fluorine atom. Here, such another resin is referred to as "Resin (x)".

Resin (X) may be one which consists of the structural unit having a fluorine atom, or one which further comprise the structural unit (a2), the structural unit (a3) or another structural unit having no acid-labile group, known in the art.

Resin (X), the content of the structural unit having a fluorine atom is preferably 80% by mole or more, more preferably 85% by mole or more, still more preferably 90% by mole or more, based on sum of the structural units in the resin.

Resin (X) usually has 8000 or more of the weight-average molecular weight, preferably 10000 or more of the weight-average molecular weight. The resin usually has 80,000 or less of the weight-average molecular weight, preferably has 60,000 or less of the weight-average molecular weight.

The weight-average molecular weight can be measured with known methods such as liquid chromatography or gas chromatography.

When the photoresist composition comprises Resin (X), the content of the resin is preferably 1 to 60 weight parts, more preferably 3 to 50 weight parts, and still more preferably 5 to 40 weight parts, and further still more preferably 7 to 30 weight parts, relative to 100 parts of Resin (A).

The total content of the resins in the photoresist composition of the present invention is usually 80% by mass or more based on sum of solid component, and usually 99% by mass or less.

In this specification, "solid component" means components other than solvent in the photoresist composition.

The photoresist composition of the present invention may comprise a solvent.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention. The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the present invention may further comprise a quencher. The "quencher" has the property that it can trap an acid, especially an acid generated from the acid generator by applying a radiation.

Examples of the quencher include a basic nitrogen-containing organic compound and a weak acid salt.

Examples of the basic nitrogen-containing organic compound include an amine compound such as an aliphatic amine, an aromatic amine and an ammonium salt. Examples of the aliphatic amine include a primary amine, a secondary amine and a tertiary amine. Examples of the aromatic amine include an aromatic amine in which an aromatic ring has an amino group such as aniline and a heteroaromatic amine such as pyridine.

Examples of the quencher include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylanine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, 2 tris [2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenyl methane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy) ethane, di(2-pyridyl) ketone, 4,4'-dipyridyl sulfide, 4,4'-dipyridyl disulfide, 2,2'-dipyridylamine, 2,2'-dipicolylamine and bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

The weak acid salt is usually lower in acidity than the acid generator as mentioned above and Salt (I), examples of which include carboxylic acid salts and sulfonic acid salts.

The acidity in the weak acid salt is shown by the acid dissociation constant (pKa).

The acid dissociation constant of acid generated from the weak acid salt is usually salt of $-3 < pKa$.

The weak acid salt is preferably a salt of $-1 < pKa < 7$, and more preferably a salt of $0 < pKa < 5$.

Specific examples of the weak acid salt include the following ones.
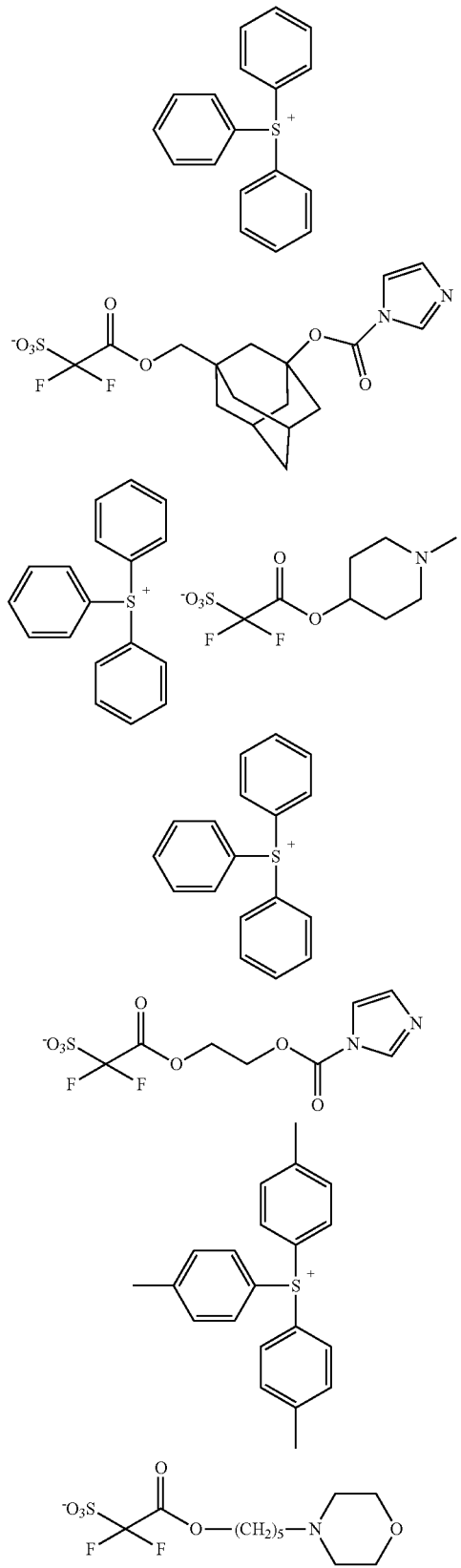
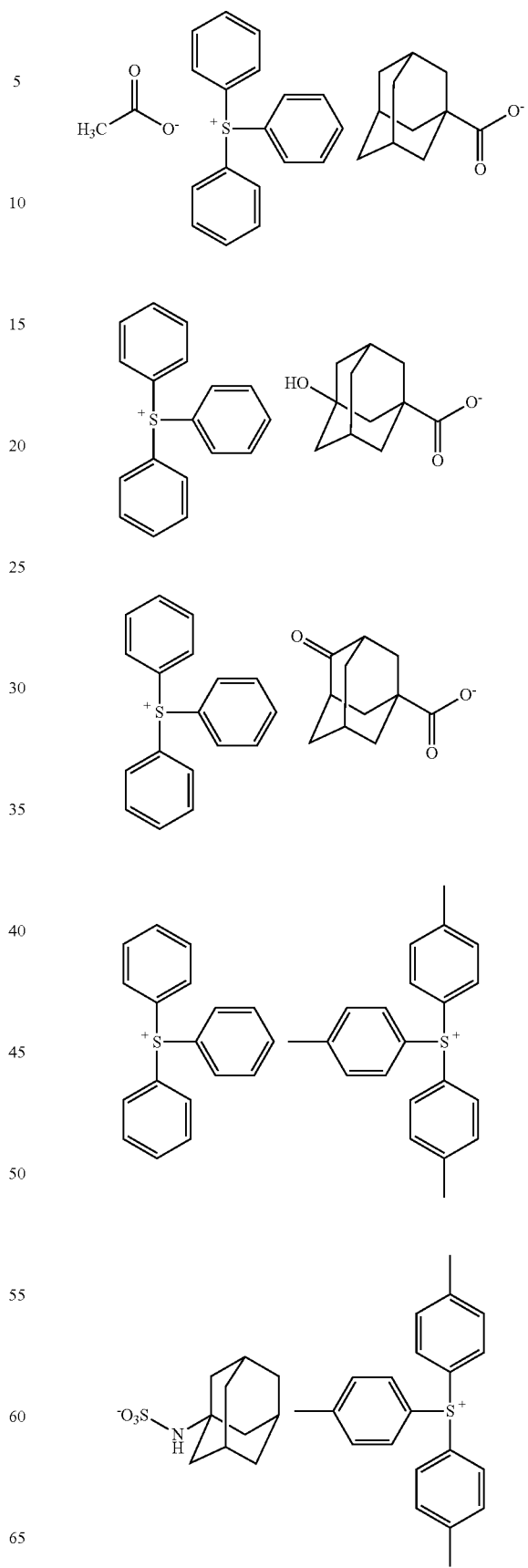

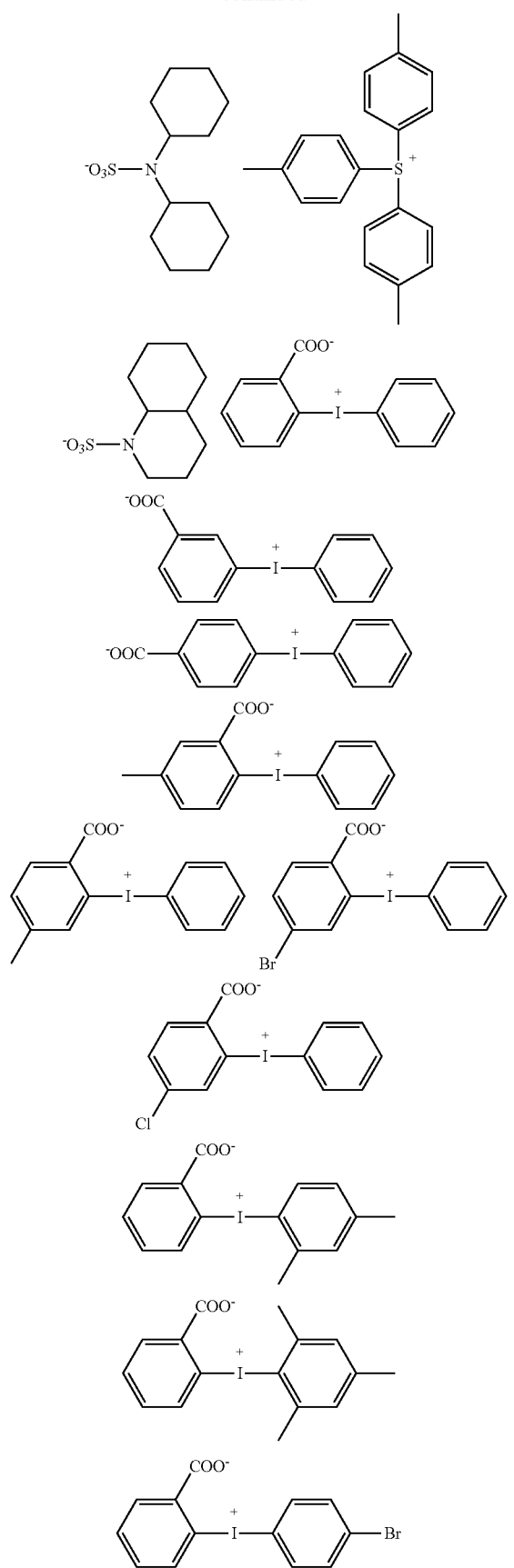
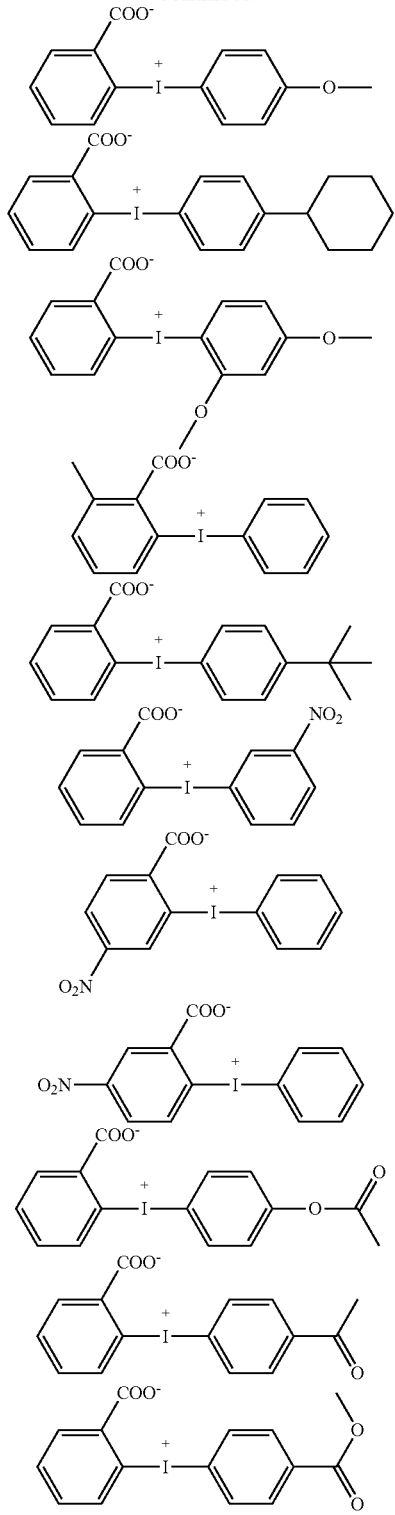

The weak acid salt is preferably an intramolecular salt, more preferably salts having a carboxylic anion and a bromide ion.

The content of quencher is preferably 0.01 to 5% by mass, more preferably 0.01 to 3% by mass, and still more preferably 0.01 to 1% by mass, based on sum of solid component.

The photoresist compositions of the present invention may comprise, if necessary, a small amount of various additives such as a sensitizer, a dissolution inhibitor, other polymers, a surfactant, a stabilizer and a dye as long as the effect of the present invention is not prevented.

The photoresist compositions of the present invention can usually be prepared by mixing, in a solvent, Salt (I) and Resin (A), and if necessary a known acid generator, a quencher, and/or additives at a suitable ratio for the composition, optionally followed by filtrating the mixture with a filter having 0.003 µm to 0.2 µm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the present invention are useful for a chemically amplified photoresist composition.

The photoresist compositions of the present invention are useful for a chemically amplified photoresist composition.

A photoresist pattern can be produced by the following steps (1) to (5):

(1) a step of applying the photoresist composition of the present invention on a substrate, (2) a step of forming a composition film by conducting drying, (3) a step of exposing the composition film to radiation, (4) a step of baking the exposed composition film, and (5) a step of developing the baked composition film with an alkaline developer.

The applying of the photoresist composition on a substrate is usually conducted using a conventional apparatus such as spin coater. The photoresist composition is preferably filtrated with filter having a pore size of 0.01 to 0.2 µm before applying. Examples of the substrate include a silicon wafer or a quartz wafer on which a sensor, a circuit, a transistor or the like is formed.

The formation of the composition film is usually conducted using a heating apparatus such as hot plate or a decompressor, and the heating temperature is usually 50 to 200° C. When the pressure is reduced during heating, the operation pressure is usually 1 to $1.0*10^5$ Pa. The heating time is usually 10 to 180 seconds.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed composition film is usually 50 to 200° C., and preferably 70 to 150° C.

The development of the baked composition film is usually carried out using a development apparatus. The development method includes dipping methods, paddle methods, spray methods and dynamic dispense method. The developing temperature is preferably 5 to 60° C., and the developing time is preferably 5 to 300 seconds.

The positive and negative type photoresist patterns can be obtained by the development depending on a developer to be used therefor.

When a positive type photoresist pattern is prepared from the photoresist composition of the present invention, the development can be conducted with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The alkaline developer may comprise a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the present invention, the development can be conducted with a developer containing an organic solvent, such developer is sometimes referred to as "organic developer".

Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 50% to 100% by weight, more preferably from 90% to 100% by weight. Preferred is that the organic developer essentially consists of butyl acetate and/or 2-heptanone. The organic developer may comprise a surfactant or a very small amount of water.

Development with an organic developer can be stopped by replacing the developer by other solvent than it such as alcohol.

The photoresist composition of the present invention provides a photoresist pattern showing good Exposure Latitude (EL), and therefore, the photoresist composition of the present invention is suitable for KrF excimer laser lithography, ArF excimer laser lithography, EUV (extreme ultraviolet) lithography, EUV immersion lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a mass basis unless otherwise specifically noted.

The weight-average molecular weight of any material used in the following examples is determined with gel permeation chromatography under the following condition.

Equipment: HLC-8120 GCP type, manufactured by TOSOH CORPORATION

Column: Three of TSKgel Multipore HXL-M with guard column, manufactured by TOSOH CORPORATION Solvent: tetrahydrofuran Flow rate: 1.0 mL/min.

Detector: RI Detector

Column temperature: 40° C.

Injection volume: 100 μL

Standard reference material: Standard polystyrene (manufactured by TOSOH CORPORATION)

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Here, The values at the peaks of spectrum are referred to as "MASS."

Example 1

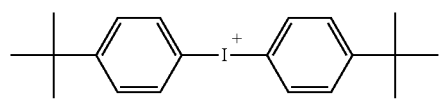

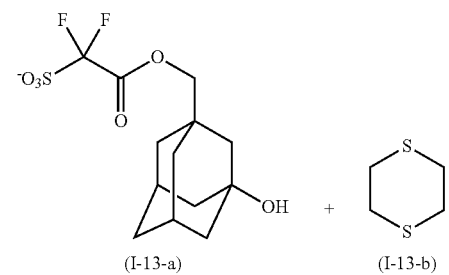

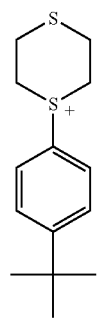
(I-13-d)

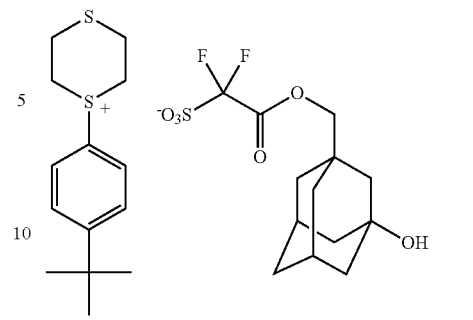

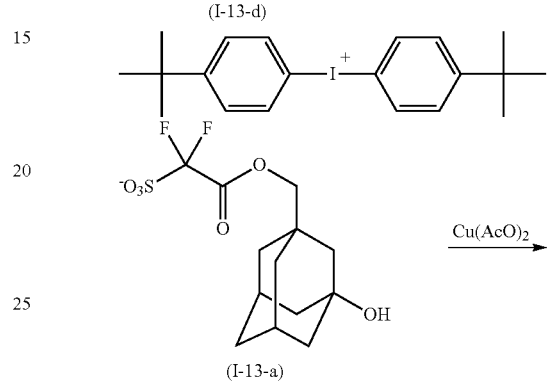

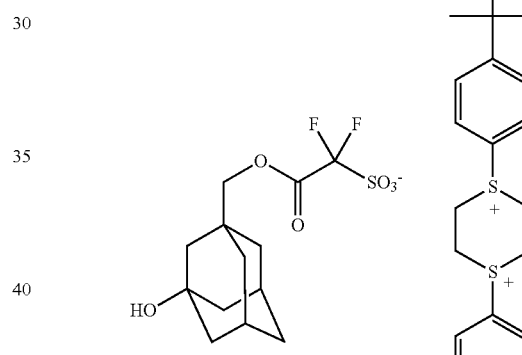

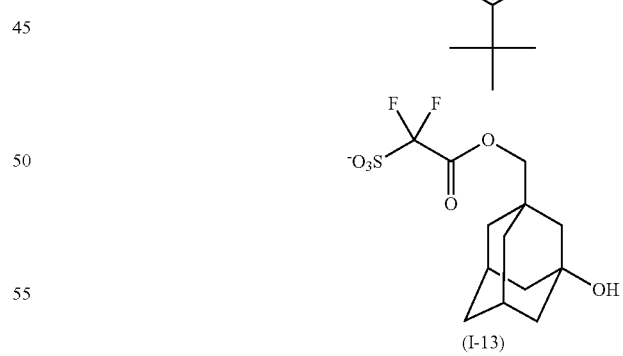

To a reactor, 4.87 parts of the salt represented by formula (I-13-a), 0.80 parts of the compound represented by formula (I-13-b) and 40 parts of chloroform were added and then they were stirred at 23° C. for 30 minutes.

To the resultant mixture, 0.02 parts of the compound represented by formula (I-13-c) was added and reflux was conducted with stirring at 60° C. for 72 hours to obtain a reaction mixture containing a salt represented by formula (I-13-d).

To the obtained reaction mixture, 4.87 parts of the compound represented by formula (I-13-a) and 0.02 parts of copper acetate were added and reflux was conducted with stirring at 60° C. for 72 hours.

The reaction mixture was cooled down to 23° C., and 15 parts of 5% aqueous oxalic acid solution was added thereto and stirred at 23° C. for 30 minutes, followed by separating into an organic phase therefrom.

To the obtained organic phase, 15 parts of ion-exchanged water was added and then stirred at 23° C. for 30 minutes, followed by separating an organic phase therefrom: This step was conducted five times.

After this step, the washed organic phase was filtrated and then the obtained filtrated solution was concentrated. To the obtained residue, 3 parts of acetonitrile and 80 parts of tert-butylmethylether were added and stirred for 30 minutes and the obtained mixture was filtrated to obtain 3.23 parts of the salt represented by formula (I-13).

MS (ESI (+) Spectrum): M⁺ 386.2
MS (ESI (−) Spectrum): M⁻ 339.1

Example 2

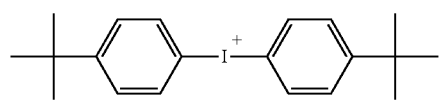
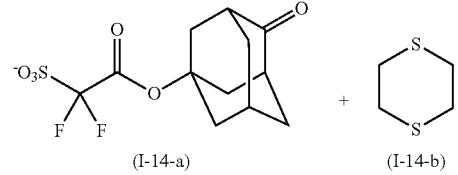

To a reactor, 4.76 parts of the salt represented by formula (I-14-a), 0.80 parts of the compound represented by formula (I-14-b) and 40 parts of chloroform were added and then they were stirred at 23° C. for 30 minutes.

To the resultant mixture, 0.02 parts of the compound represented by formula (I-14-c) was added, followed by conducting reflux with stirring at 60° C. for 72 hours to obtain a reaction mixture containing a salt represented by formula (I-14-d).

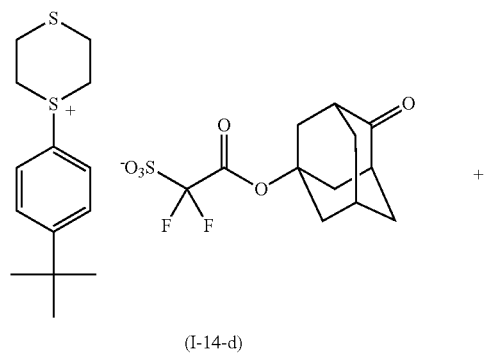

-continued

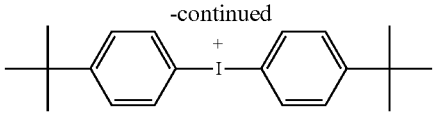

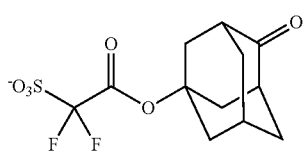

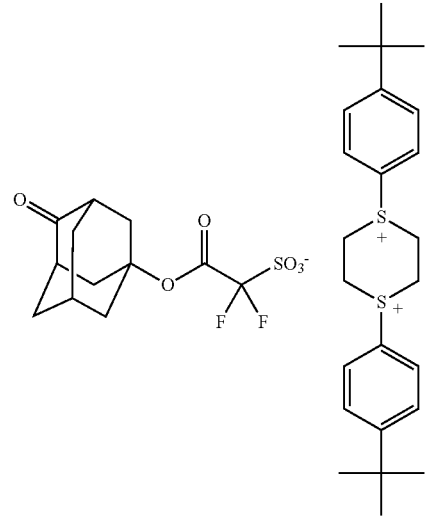

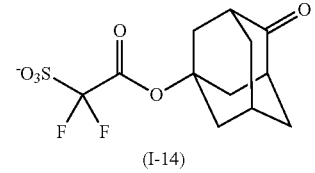

To the obtained reaction mixture, 4.76 parts of the compound represented by formula (I-14-a) and 0.02 parts of copper acetate were added and reflux was conducted with stirring at 60° C. for 72 hours.

The reaction mixture was cooled down to 23° C., and 15 parts of 5% aqueous oxalic acid solution was added thereto and stirred at 23° C. for 30 minutes, followed by separating into an organic phase therefrom.

To the obtained organic phase, 15 parts of ion-exchanged water was added and then stirred at 23° C. for 30 minutes, followed by separating an organic phase therefrom: This step was conducted five times.

After this step, the organic phase was filtrated and then the obtained filtrated solution was concentrated. To the obtained residue, 3 parts of acetonitrile and 80 parts of tert-butylmethylether were added and stirred for 30 minutes and the obtained mixture was filtrated to obtain 3.48 parts of the salt represented by formula (I-14).

MS (ESI (+) Spectrum): M⁺ 386.2
MS (ESI (−) Spectrum): M⁻ 323.0

Example 3

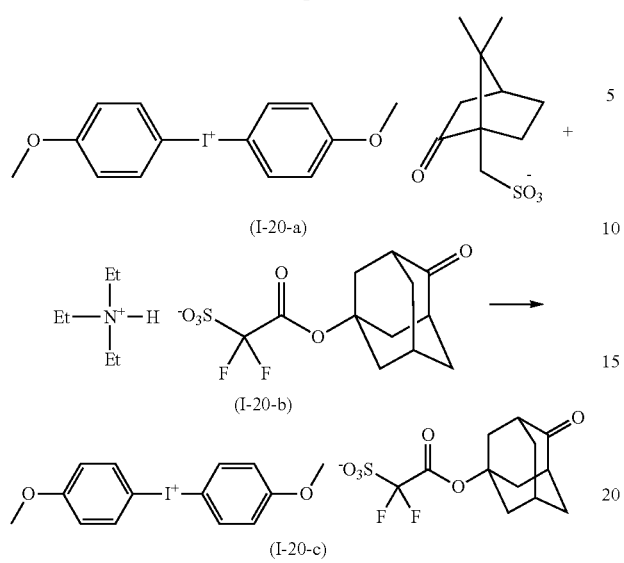

To a reactor, 6.00 parts of the salt represented by formula (I-20-a) and 60 parts of chloroform were added, and further 8.92 parts of the salt represented by formula (I-20-b) and 30 parts of ion-exchanged water were added, followed by being stirred at 23° C. for 30 minutes.

Then an organic phase was separated from the resulting reaction mixture. To the obtained organic phase, 30 parts of ion-exchanged water was added and then stirred at 23° C. for 30 minutes, followed by separating into an organic phase: This step was conducted twice. Then the organic phase was concentrated. The residue was mixed with 30 parts of tert-butylmethylether and then the supernatant was removed therefrom. Then residue was concentrated and 30 parts of n-heptane was added thereto, followed by being stirred. After stirring, the obtained one was filtrated to give 4.69 parts of the salt represented by formula (I-20-c).

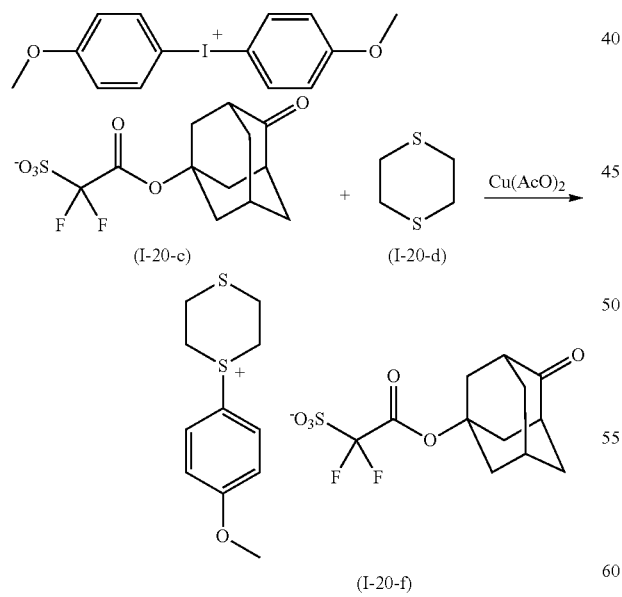

To a reactor, 4.41 parts of the salt represented by formula (I-20-c), 0.8 parts of the compound represented by formula (I-20-d) and 40 parts of Chloroform were added, and then they were stirred at 23° C. for 30 minutes.
To the obtained mixture, 0.02 parts of copper acetate was added, followed by conducting reflux with stirring at 60° C. for 72 hours to obtain a reaction mixture containing the salt represented by formula (I-20-f).

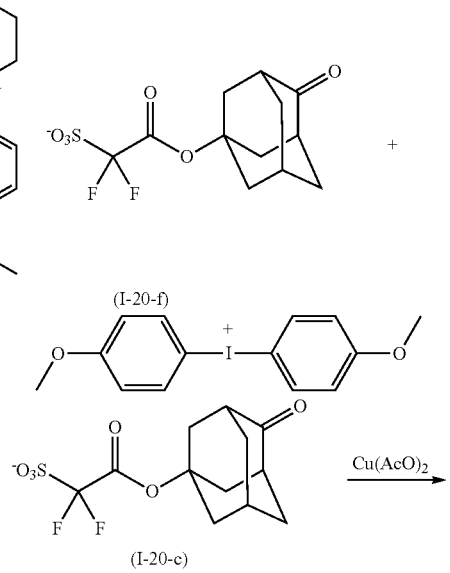

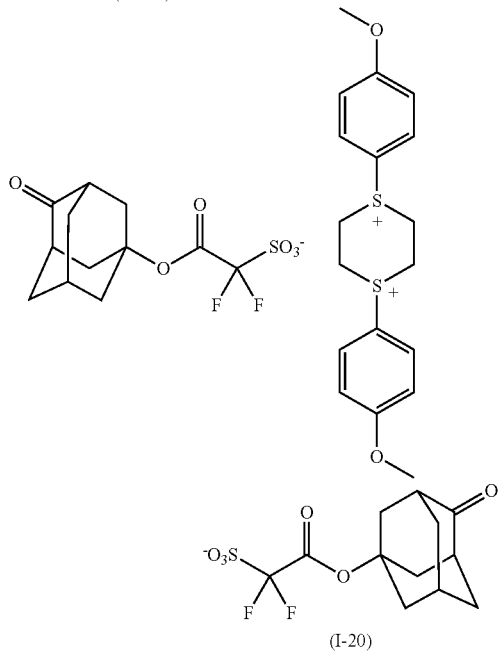

To the obtained reaction mixture, 4.41 parts of the compound represented by formula (I-20-c) and 0.02 parts of copper acetate were added and reflux was conducted with stirring at 60° C. for 72 hours.

The reaction mixture was cooled down to 23° C., and 15 parts of 5% aqueous oxalic acid solution was added thereto and stirred at 23° C. for 30 minutes, followed by separating into an organic phase therefrom.

Then the organic layer was washed with 15 parts of ion-exchanged water, followed by separating into an organic phase therefrom: This washing was conducted five times.

After washing, the organic layer was filtrated and then the filtrate was concentrated. To the obtained residue, 3 parts of acetonitrile and 80 parts of tert-butylmethylether were added and stirred for 30 minutes, followed by being concentrated to obtain 3.24 parts of the salt represented by formula (I-20).

MS (ESI (+) Spectrum): $M^+$ 334.1
MS (ESI (−) Spectrum): $M^-$ 323.0

Example 4

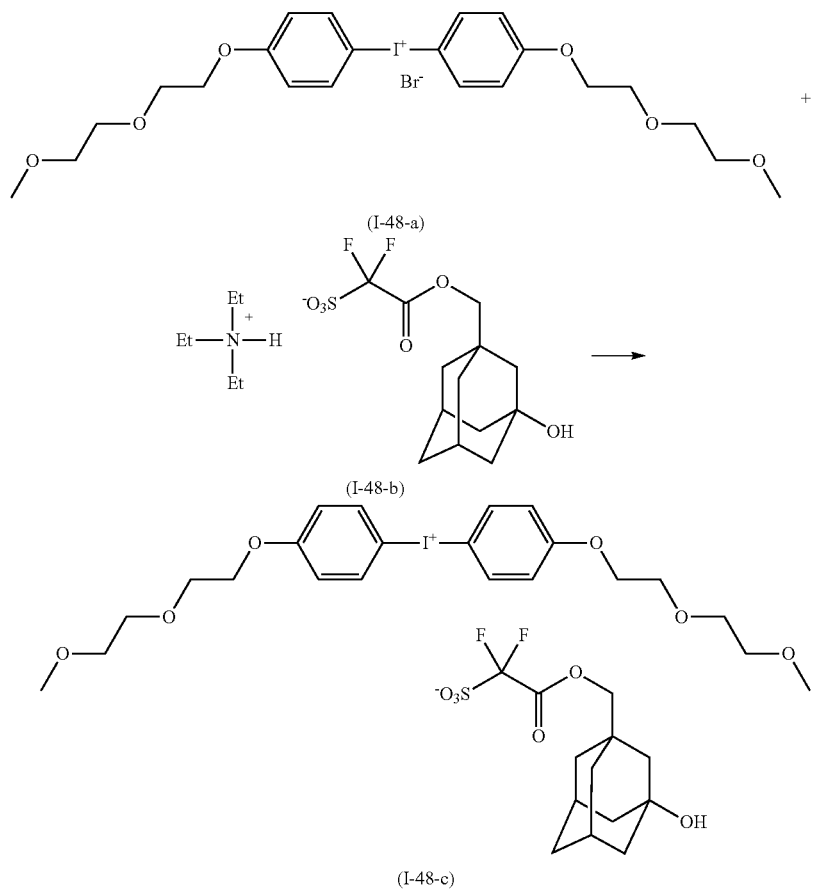

To a reactor, 8.63 parts of the salt represented by formula (I-48-a), 7.65 parts of the salt represented by formula (I-48-b), 62 parts of chloroform and 41 parts of ion-exchanged water were added and they were stirred at 23° C. for 12 hours. Then an organic phase was separated from the resulting reaction mixture.

To the obtained organic phase, 25 parts of ion-exchanged water was added and then stirred at 23° C. for 30 minutes, followed by separating into an organic phase: This step was conducted 5 times. Then the organic phase was concentrated. To the residue, 10.2 parts of acetonitrile and 24.08 parts of tert-butylmethylether were added and then stirred, followed by being filtrated to obtain 4.96 parts of the salt represented by formula (I-48-c).

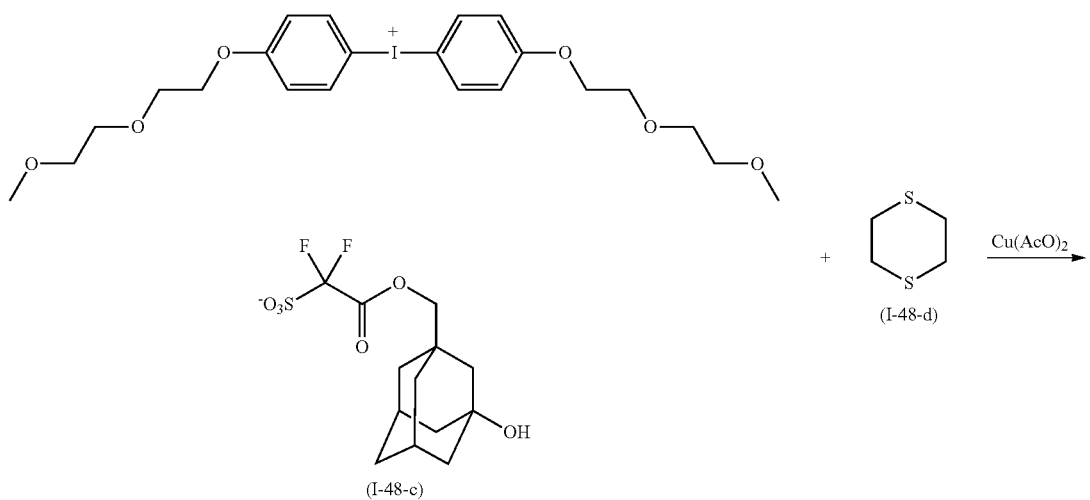

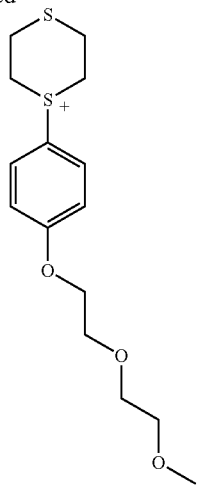
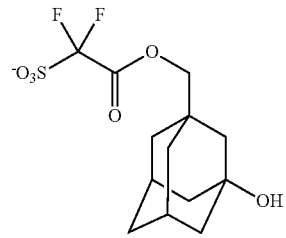

(I-48-f)

To a reactor, 5.69 parts of the salt represented by formula (I-48-c), 0.8 parts of the compound represented by formula (I-48-d) and 40 parts of chloroform were added, and then they were stirred at 23° C. for 30 minutes.

To the obtained mixture, 0.02 parts of copper acetate was added, followed by conducting reflux with stirring at 60° C. for 72 hours to obtain a reaction mixture containing the salt represented by formula (I-48-f).

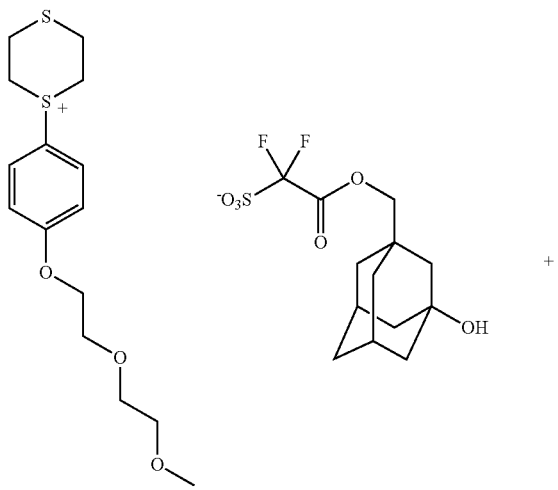

(I-48-f)

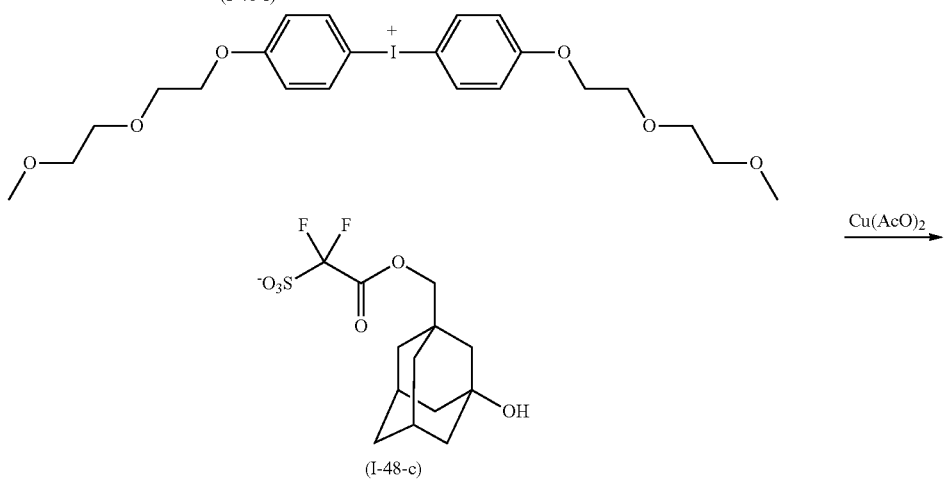

(I-48-c)

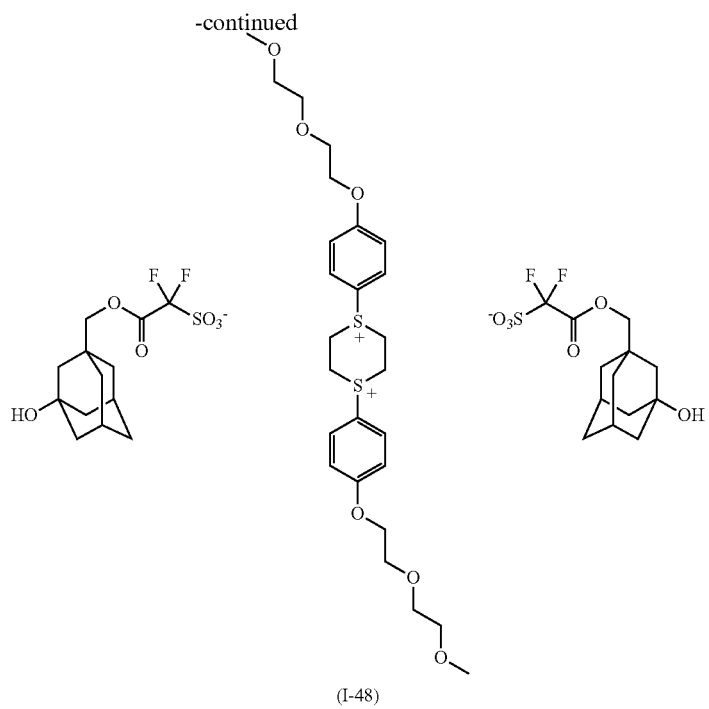

(I-48)

To the obtained reaction mixture, 5.69 parts of the compound represented by formula (I-48-c) and 0.02 parts of copper acetate were added and reflux was conducted with stirring at 60° C. for 72 hours.

The reaction mixture was cooled down to 23° C., and 15 parts of 5% aqueous oxalic acid solution was added thereto and stirred at 23° C. for 30 minutes, followed by separating into an organic phase therefrom.

Then the organic layer was washed with 15 parts of ion-exchanged water, followed by separating into an organic phase therefrom: This washing was conducted five times. After washing, the organic layer was filtrated and then the filtrate was concentrated. To the obtained residue, 3 parts of acetonitrile and 80 parts of tert-butylmethylether were added and stirred for 30 minutes, followed by being concentrated to obtain 3.62 parts of the salt represented by formula (I-48).

MS (ESI (+) Spectrum): $M^+$ 510.2
MS (ESI (−) Spectrum): $M^-$ 339.1

Synthesis Example 1

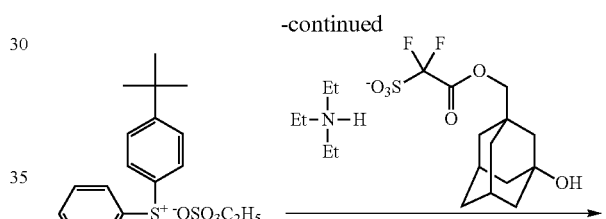

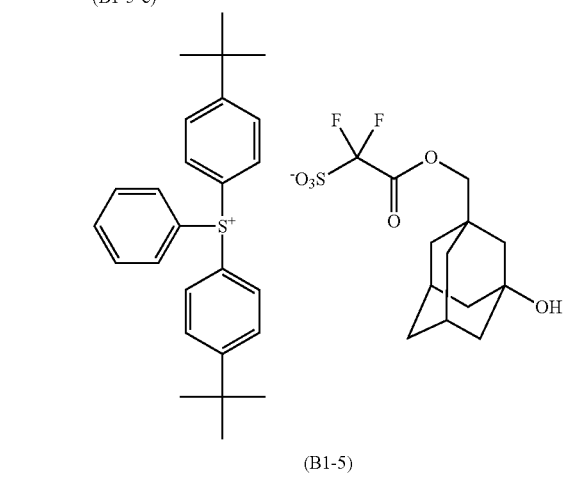

To a reactor, 50.49 parts of the salt represented by formula (B1-5-a) and 252.44 parts of chloroform were added and they were stirred at 23° C. for 30 minutes. Then 16.27 parts of the salt represented by formula (B1-5-b) was dropped thereto and then stirred at 23° C. for an hour to obtain a solution containing the salt represented by formula (B1-5-c).

To the obtained solution, 48.8 parts of the salt represented by formula (B1-5-d) and 84.15 parts of ion-exchanged water were added then stirred at 23° C. for 12 hours to obtain a reaction solution with two separated phases. Then chloroform layer was separated therefrom, and 84.15 parts of ion-exchanged water was added thereto for washing: This washing step was conducted 5 times.

To the washed chloroform layer, 3.88 parts of active carbon was added and then they were stirred, followed by conducting filtration.

The collected filtrate was concentrated. To the obtained residue, 125.87 parts of acetonitrile was added and stirred, followed by being concentrated.

To the obtained residue, 20.62 parts of acetonitrile and 309.30 parts of tert-butylmethylether were added and stirred at 23° C. for 30 minutes, followed by removing its supernatant therefrom. Then To the residue, 200 parts of n-heptane was added and stirred at 23° C. for 30 minutes, followed by being filtrated to obtain 61.54 parts of the salt represented by formula (B1-5).

MS (ESI (+) Spectrum): M⁺ 375.2
MS (ESI (−) Spectrum): M⁻ 339.1

Synthesis Example 2

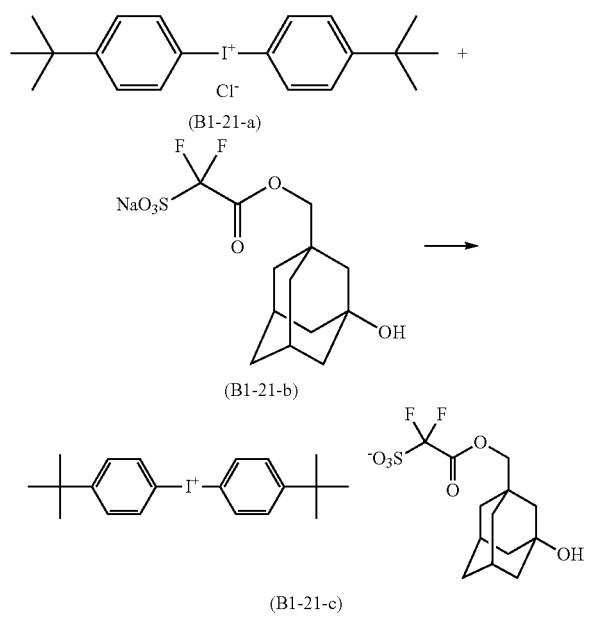

In a reactor, 30.00 parts of the salt represented by formula (B1-21-b) which had been produced according to the method described in JP 2008-209917 A, 35.50 parts of the salt represented by formula (B1-21-a), 100 parts of chloroform and 50 parts of ion-exchanged water were fed and stirred at 23° C. for 15 hours. From the obtained reaction mixture which had two phases, a chloroform phase was collected with separation.

The chloroform phase was washed with 30 parts of ion-exchanged water for washing: This washing was conducted five times.

The washed chloroform phase was concentrated. To the obtained residue, 100 parts of tert-butylmethylether was added and then stirred at 23° C. for 30 minutes, followed by being filtrated to obtain 48.57 parts of the salt represented by formula (B1-21-c).

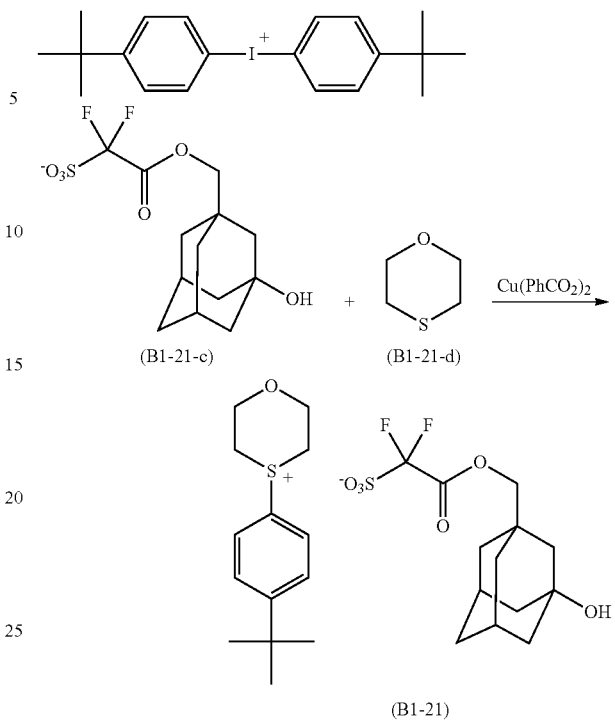

Into a reactor, 20.00 parts of the salt represented by formula (B1-21-c), 2.84 parts of the compound represented by formula (B1-21-d) and 250 parts of monochlorobenzene were fed and then they were stirred at 23° C. for 30 minutes.

To the resultant mixture, 0.21 part of copper (II) dibenzoate was added. The resultant mixture was stirred at 100° C. for 1 hour. The obtained mixture was concentrated, and then 200 parts of chloroform and 50 parts of ion-exchanged water were added to the obtained residue, followed by being stirred at 23° C. for 30 minutes.

Then the organic phase was collected by separation. Then 50 parts of ion-exchanged water was added to the organic layer and stirred at 23° C. for 30 minutes, followed by collecting an organic phase by separation: This washing was conducted five times.

The washed organic layer was concentrated. To the residue, 53.51 parts of acetonitrile was added, and the resultant mixture was concentrated. To the residue, 113.05 parts of tert-butylmethylether was added and then they were stirred, followed by being filtrated to obtain 10.47 parts of the salt represented by formula (B1-21).

MS (ESI (+) Spectrum): M⁺ 237.1
MS (ESI (−) Spectrum): M⁻ 339.1

Synthesis Example 3

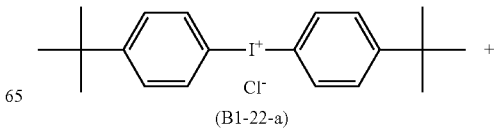

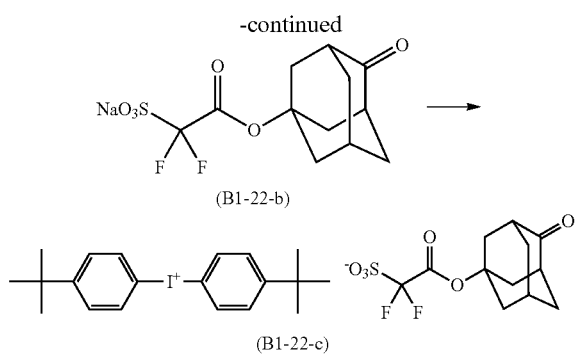

(B1-22-b)

(B1-22-c)

Into a reactor, 11.26 parts of the salt represented by formula (B1-22-a), 10.00 parts of the compound represented by formula (B1-22-b), 50 parts of chloroform and 25 parts of ion-exchanged water were fed and then stirred at 23° C. for 15 hours.
From the obtained reaction mixture which had two phases, a chloroform phase was collected with separation.
Then 15 parts of ion-exchanged water was added to the chloroform for washing phase: This washing was conducted five times.
The washed chloroform phase was concentrated. To the obtained residue, 50 parts of tert-butylmethylether was added and then stirred at 23° C. for 30 minutes, followed by being filtrated to obtain 11.75 parts of the salt represented by formula (B1-22-c).

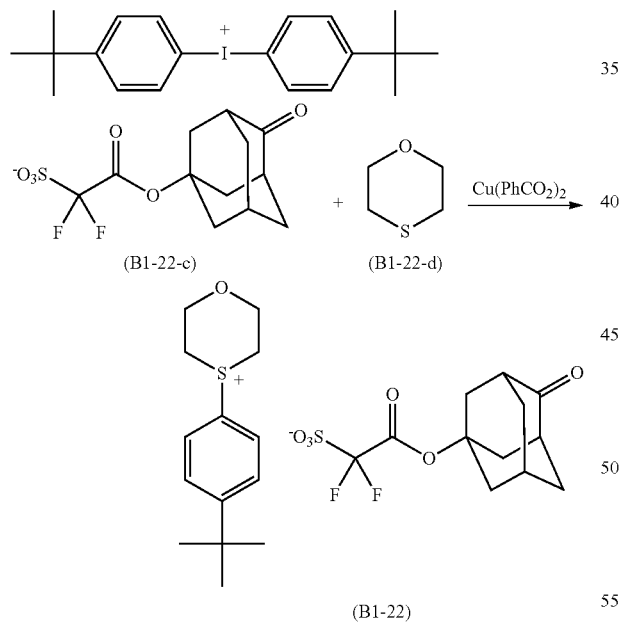

(B1-22-c)   (B1-22-d)

(B1-22)

Into a reactor, 11.71 parts of the salt represented by formula (B1-22-c), 1.70 parts of the compound represented by formula (B1-22-d) and 46.84 parts of monochlorobenzene were fed and then they were stirred at 23° C. for 30 minutes.
To the resultant mixture, 0.12 part of copper (II) dibenzoate was added. The resultant mixture was stirred at 100° C. for 30 minutes.
The mixture was concentrated, and then 50 parts of chloroform and 12.50 parts of ion-exchanged water were added to the obtained residue, followed by being stirred at 23° C. for 30 minutes. Then the organic phase was collected by separation. Then 12.50 parts of ion-exchanged water was added to the organic layer and stirred at 23° C. for 30 minutes, followed by collecting an organic phase by separation: This washing was conducted eight times.

The washed organic layer was concentrated. To the residue, 50 parts of tert-butylmethylether was added, followed by being filtrated to obtain 6.84 parts of the salt represented by formula (B1-22).

MS (ESI (+) Spectrum): $M^+$ 237.1

MS (ESI (−) Spectrum): $M^-$ 323.0

Compounds used as monomers in the following Synthesis Examples are shown as follow.

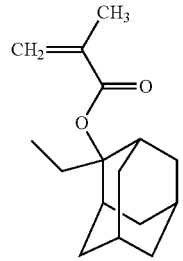

(a1-1-2)

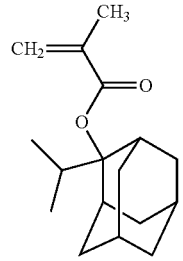

(a1-1-3)

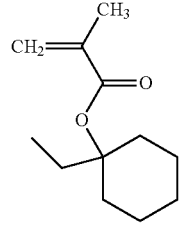

(a1-2-3)

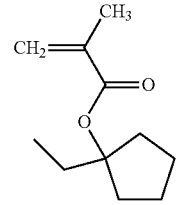

(a1-2-9)

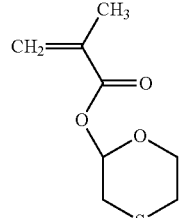

(a1-5-1)

(a1-0-10)
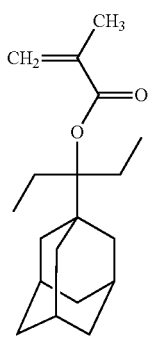

(a2-1-1)
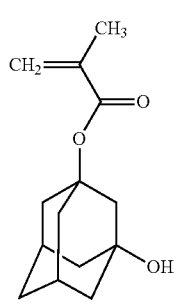

(a2-1-3)
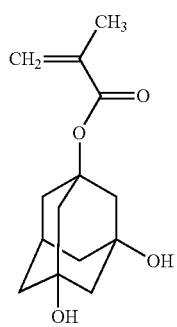

(a3-1-1)
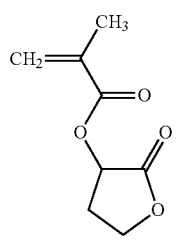

(a3-2-3)
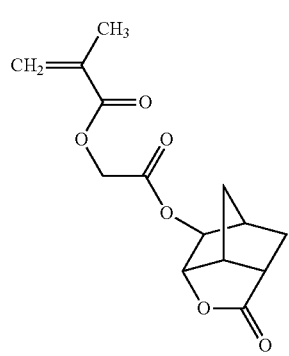

(a3-4-2)
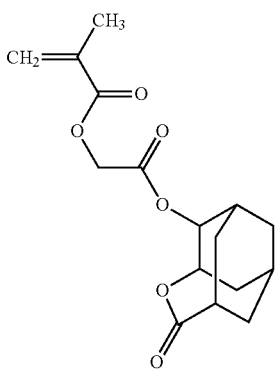

(a4-0-1)
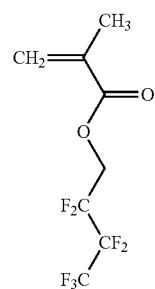

(a4-1-7)
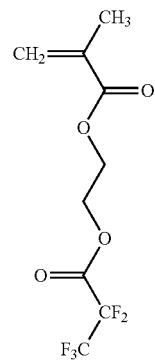

(a5-1-1)
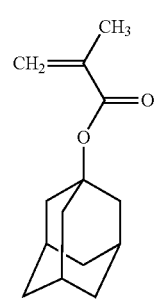

Here, each of the compounds is referred as to "monomer (X)" where "X" is the symbol of the formula representing the monomer.

Synthesis Example 4

There were mixed monomers (a1-1-3), (a1-2-9), (a2-1-3) and (a3-4-2) in a molar ratio of 45/14/2.5/38.5 (monomer (a1-1-3)/monomer (a1-2-9)/monomer (a2-1-3)/monomer (a3-4-2)) as well as propyleneglycolmonomethylether acetate in 1.5 times part based on total parts of all monomers to prepare a mixture. To the mixture, azobisisobutyronitrile as an initiator in the ratio of 1 mol % based on all monomer molar amount and azobis (2,4-dimethylvaleronitrile) as an initiator in the ratio of 3 mol % based on all monomer molar amount were added, and the obtained mixture was heated at 73° C. for about 5 hours. The reaction mixture was poured into a large amount of a mixture of methanol and water to cause precipitation. The precipitate was collected by filtration.

Then the filtrates were dissolved in propyleneglycolmonomethylether acetate and poured the resultant solution into a large amount of a mixture of methanol and water to cause precipitation, followed by being filtrated: This operation was conducted twice for purification.

As a result, a resin having a weight-average molecular weight of about $7.6 \times 10^3$ was obtained in yield of 68%. This resin is called as resin A1. Resin A1 had the following structural units.

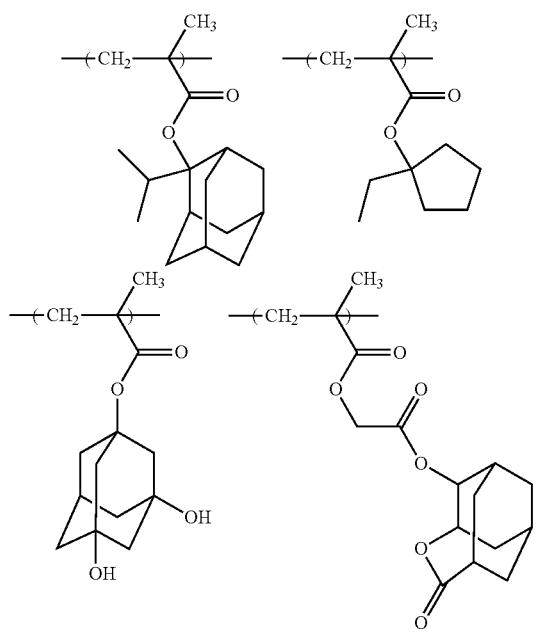

Synthesis Example 5

There were mixed monomers (a1-1-3), (a1-5-1), (a2-1-3) and (a3-4-2) in a molar ratio of 45/14/2.5/38.5 [monomer (a1-1-3)/monomer (a1-5-1)/monomer (a2-1-3)/monomer (a3-4-2)] as well as propyleneglycolmonomethylether acetate in 1.5 times part based on total parts of all monomers to prepare a mixture.

To the mixture, azobisisobutyronitrile as an initiator in the ratio of 1 mol % based on all monomer molar amount and azobis(2,4-dimethylvaleronitrile) as an initiator in the ratio of 3 mol % based on all monomer molar amount were added, and the obtained mixture was heated at 73° C. for about 5 hours. The reaction mixture was poured into a large amount of a mixture of methanol and water to cause precipitation. The precipitate was collected by filtration.

Then the filtrates were dissolved in propyleneglycolmonomethylether acetate and poured the resultant solution into a large amount of a mixture of methanol and water to cause precipitation, followed by being filtrated: This operation was conducted twice for purification.

As a result, a resin having a weight-average molecular weight of about $7.9 \times 10^3$ was obtained in yield of 70%. This resin is called as resin A2. Resin A2 had the following structural units.

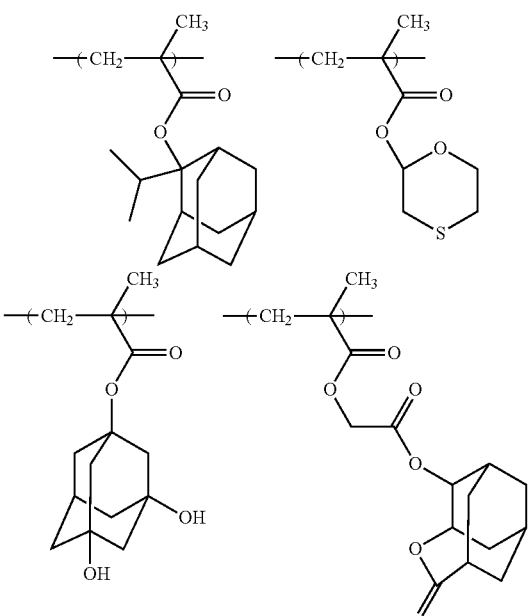

Synthesis Example 6

There were mixed monomers (a1-0-10), (a1-2-9), (a2-1-3) and (a3-4-2) in a molar ratio of 45/14/2.5/38.5 [monomer (a1-0-10)/monomer (a1-2-9)/monomer (a2-1-3)/monomer (a3-4-2)] as well as propyleneglycolmonomethylether acetate in 1.5 times part based on total parts of all monomers to prepare a mixture.

To the mixture, azobisisobutyronitrile as an initiator in the ratio of 1.6 mol % based on all monomer molar amount and azobis(2,4-dimethylvaleronitrile) as an initiator in the ratio of 4.8 mol % based on all monomer molar amount were added, and the obtained mixture was heated at 73° C. for about 5 hours. The reaction mixture was poured into a large amount of a mixture of methanol and water to cause precipitation. The precipitate was collected by filtration.

Then the filtrates were dissolved in propyleneglycolmonomethylether acetate and poured the resultant solution into a large amount of a mixture of methanol and water to cause precipitation, followed by being filtrated: This operation was conducted twice for purification.

As a result, a resin having a weight-average molecular weight of about $7.5 \times 10^3$ was obtained in yield of 60%. This resin is called as resin A3. Resin A3 had the following structural units.

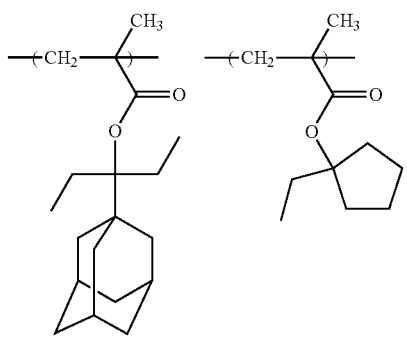

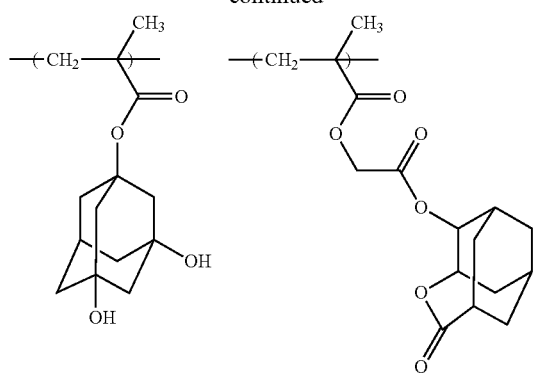

Synthesis Example 7

There were mixed monomers (a1-1-2), (a1-2-3), (a2-1-1), (a3-1-1) and (a3-2-3) in a molar ratio of 30/14/6/20/30 [monomer (a1-1-2)/monomer (a1-2-3)/monomer (a2-1-1)/monomer (a3-1-1)/monomer (a3-2-3)] as well as 1,4-dioxane in 1.5 times part based on total parts of all monomers to prepare a mixture.

To the mixture, azobisisobutyronitrile as an initiator in the ratio of 1 mol % based on all monomer molar amount and azobis(2,4-dimethylvaleronitrile) as an initiator in the ratio of 3 mol % based on all monomer molar amount were added, and the obtained mixture was heated at 75° C. for about 5 hours.

The reaction mixture was poured into a large amount of a mixture of methanol and water, in mixture ratio of 4/1, to cause precipitation.

The precipitate was collected by filtration: This operation was conducted three times for purification.

As a result, a resin having a weight-average molecular weight of about $7.2 \times 10^3$ was obtained in yield of 78%. This resin is called as resin A4. Resin A4 had the following structural units.

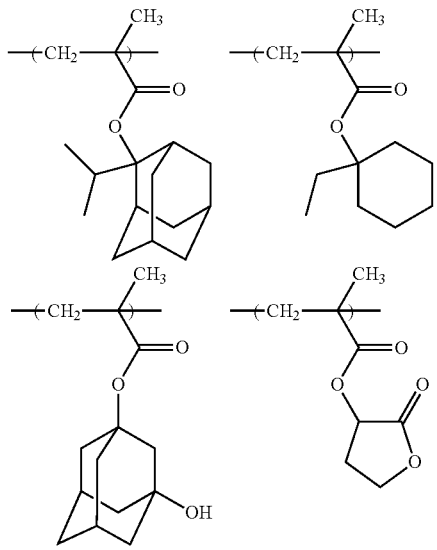

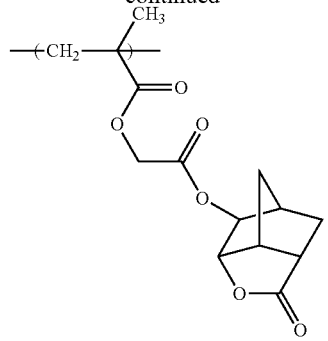

Synthesis Example 8

There were mixed monomers (a1-1-2), (a2-1-1) and (a3-1-1) in a molar ratio of 50/25/25 [monomer (a1-1-2)/monomer (a2-1-1)/monomer (a3-1-1)] as well as 1,4-dioxane in 1.5 times part based on total parts of all monomers to prepare a mixture.

To the mixture, azobisisobutyronitrile as an initiator in the ratio of 1 mol % based on all monomer molar amount and azobis(2,4-dimethylvaleronitrile) as an initiator in the ratio of 3 mol % based on all monomer molar amount were added, and the obtained mixture was heated at 80° C. for about 8 hours.

The reaction mixture was poured into a large amount of a mixture of methanol and water, in mixture ratio of 4/1, to cause precipitation.

The precipitate was collected by filtration: This operation was conducted three times for purification.

As a result, a resin having a weight-average molecular weight of about $9.2 \times 10^1$ was obtained in yield of 60%. This resin is called as resin A5. Resin A5 had the following structural units.

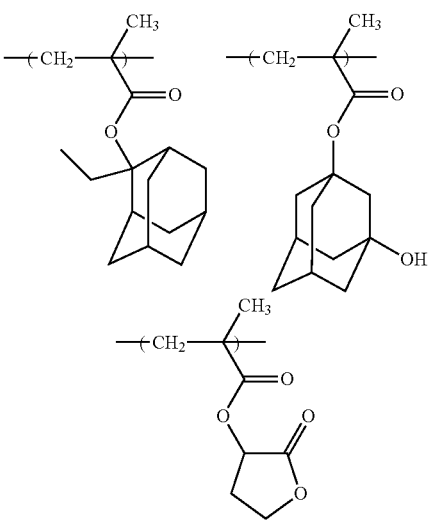

Synthesis Example 9

There were mixed monomer (a4-1-7) and 1,4-dioxane in 1.5 times part based on total parts of all monomers to prepare a mixture. To the mixture, azobisisobutyronitrile as an initiator in the ratio of 0.7 mol % based on all monomer molar amount and azobis(2,4-dimethylvaleronitrile) as an initiator in the ratio of 2.1 mol % based on all monomer molar amount were added, and the obtained mixture was heated at 75° C. for about 5 hours.

The reaction mixture was poured into a large amount of a mixture of methanol and water to cause precipitation. The precipitate was collected by filtration.

Then the reaction mixture was poured into a large amount of a mixture of methanol and water to cause precipitation. The precipitate was collected by filtration: This operation was conducted twice for purification.

As a result, a resin having a weight-average molecular weight of about $1.8 \times 10^4$ was obtained in yield of 77%. This resin is called as resin X1. Resin X1 had the following structural unit.

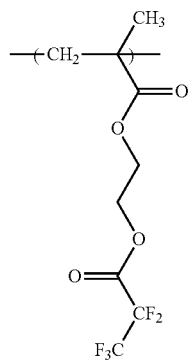

Synthesis Example 10

There were mixed monomers (a5-1-1) and (a4-O-1) in a molar ratio of 50/50 [monomers (a5-1-1)/monomer (a4-O-1)] as well as methylisobutylketone in 1.2 times part based on total parts of all monomers to prepare a mixture.

To the mixture, azobisisobutyronitrile as an initiator in the ratio of 4 mol % based on all monomer molar amount was added, and the obtained mixture was heated at 70° C. for about 5 hours.

The reaction mixture was poured into a large amount of a mixture of methanol and water to cause precipitation.

As a result, a resin having a weight-average molecular weight of about $1.1 \times 10^4$ was obtained in yield of 89%. This resin is called as resin X2. Resin X2 had the following structural units.

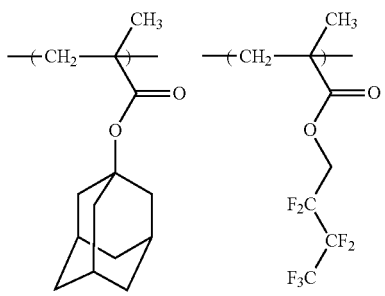

Examples 5 to 18 and Comparative Example 1

<Production of Photoresist Compositions>
The following components as listed in Table 3 were mixed and dissolved in the solvent as mentioned below, and then filtrated through a fluorine resin filter having pore diameter of 0.2 μm, to prepare photoresist compositions.

TABLE 3

| Comp. No. | Resin (kind/amount (part)) | Salt (I) (kind/amount (part)) | Acid generator (kind/amount (part)) | Quencher (kind/amount (part)) | PB (° C.)/ PEB (° C.) |
|---|---|---|---|---|---|
| Comp. 1 | A1/10 | I-13/0.8 | None | D1/0.28 | 90/85 |
| Comp. 2 | A1/10 | I-13/0.4 | B1-5/0.2 B1-22/0.2 | D1/0.28 | 90/85 |
| Comp. 3 | A1/10 | I-13/0.4 | B1-21/0.2 B1-22/0.2 | D1/0.28 | 90/85 |
| Comp. 4 | A2/10 | I-13/0.4 | B1-21/0.2 B1-22/0.2 | D1/0.28 | 90/85 |
| Comp. 5 | A3/10 | I-13/0.4 | B1-21/0.2 B1-22/0.2 | D1/0.28 | 90/85 |
| Comp. 6 | A4/10 | I-13/0.4 | B1-21/0.2 B1-22/0.2 | D1/0.28 | 105/100 |
| Comp. 7 | A1/10 X1/0.7 | I-13/0.4 | B1-21/0.2 B1-22/0.2 | D1/0.28 | 90/85 |
| Comp. 8 | A2/10 X1/0.7 | I-13/0.4 | B1-21/0.2 B1-22/0.2 | D1/0.28 | 90/85 |
| Comp. 9 | A2/10 X2/0.7 | I-13/0.4 | B1-21/0.2 B1-22/0.2 | D1/0.28 | 90/85 |
| Comp. 10 | A5/10 | I-13/0.8 | None | D1/0.28 | 90/85 |
| Comp. 11 | A1/10 X2/0.7 | I-13/0.4 | B1-21/0.2 B1-22/0.2 | D1/0.28 | 96/85 |
| Comp. 12 | A1/10 X2/0.7 | I-14/0.4 | B1-21/0.4 | D1/0.28 | 90/85 |
| Comp. 13 | A1/10 X2/0.7 | I-20/0.4 | B1-21/0.4 | D1/0.28 | 90/85 |
| Comp. 14 | A1/10 X2/0.7 | I-48/0.4 | B1-21/0.2 B1-22/0.2 | D1/0.28 | 90/85 |
| Comparative Comp. 1 | A5/10 | None | B1-x/0.8 | D1/0.28 | 105/100 |

In Table 3, each of symbols represents the following component:

<Resin>

A1: Resin A1, A2: Resin A2, A3: Resin A3, A4: Resin A4,

A5: Resin A5, X1: Resin X1, X2: Resin X2

<Salt (I)>

I-13: Salt represented by formula (I-13)

I-14: Salt represented by formula (I-14)

I-20: Salt represented by formula (I-20)

I-48: Salt represented by formula (I-48)

<Acid Generator>

B1-5: Salt represented by formula (B1-5)

B1-21: Salt represented by formula (B1-21)

B1-22: Salt represented by formula (B1-22)

B1-x:

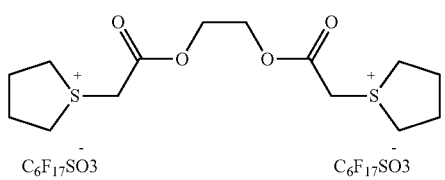

<Quencher>

D1: The compound of the following formula, which was manufactured by Tokyo Chemical Industries, Co., Ltd.

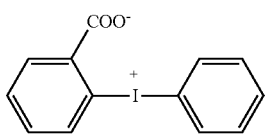

<Solvent>
E1: Mixture of the following solvents

| | |
|---|---|
| propyleneglycolmonomethylether acetate | 265 parts |
| propyleneglycolmonomethylether | 20 parts |
| 2-heptanone | 20 parts |
| γ-butyrolactone | 3.5 parts |

<Evaluation>

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating.

Each of the photoresist compositions prepared as above was spin-coated over the anti-reflective coating so that the thickness of the resulting film became 100 nm after drying. The silicon wafers thus coated with the respective photoresist compositions were each prebaked on a direct hotplate at a temperature shown in the column "PB" in Table 3 for 60 seconds. Using an ArF excimer stepper for immersion exposure ("XT: 1900Gi" manufactured by ASML, NA-1.35, ¾ Annular, X-Y polarization), each wafer thus formed with the respective resist film was subjected to contact hole pattern exposure using a photomask for forming a trench pattern having a pitch of 120 nm and a trench width of 40 nm with the exposure quantity being varied stepwise. Ultrapure water was used as an immersion medium.

After the exposure, each wafer was subjected to post-exposure baking on a hotplate at a temperature shown in the column "PEB" in Table 3 for 60 seconds and then to development in the manner of dynamic dispense method at 23° C. for 20 seconds with butyl acetate (manufactured by Tokyo Chemical Industries, Co., Ltd) to make a negative type photoresist pattern.

Effective sensitivity (ES): It was expressed as the exposure quantity that the trench width of the pattern became 40 nm after exposure and development.

Line Edge Roughness (LER): Each of the obtained photoresist patterns was observed with a scanning electronic microscope, and the deviation in its profile was determined.

The results of evaluation were marked as follow, and listed in Table 4. In each column, the number represents the deviation [in nm].

◯: The deviation was not more than 4 nm.
X: The deviation was over 4 nm.

TABLE 4

| Ex. No. | Composition | LER [nm] |
|---|---|---|
| Ex. 5 | Comp. 1 | ◯ (2.72) |
| Ex. 6 | Comp. 2 | ◯ (2.74) |
| Ex. 7 | Comp. 3 | ◯ (2.72) |
| Ex. 8 | Comp. 4 | ◯ (2.70) |
| Ex. 9 | Comp. 5 | ◯ (3.22) |
| Ex. 10 | Comp. 6 | ◯ (3.01) |
| Ex. 11 | Comp. 7 | ◯ (2.73) |
| Ex. 12 | Comp. 8 | ◯ (2.74) |
| Ex. 13 | Comp. 9 | ◯ (2.72) |

TABLE 4-continued

| Ex. No. | Composition | LER [nm] |
|---|---|---|
| Ex. 14 | Comp. 10 | ◯ (3.26) |
| Ex. 15 | Comp. 11 | ◯ (2.69) |
| Ex. 16 | Comp. 12 | ◯ (2.71) |
| Ex. 17 | Comp. 13 | ◯ (2.68) |
| Ex. 18 | Comp. 14 | ◯ (2.62) |
| Comparative Ex. 1 | Compar. Comp. 1 | x (5.39) |

The salt of the present invention is suitable for an acid generator and the photoresist composition comprising the salt of the present invention provides a good photoresist pattern with reduced line edge roughness.

What is claimed is:

1. A salt represented by formula (I):

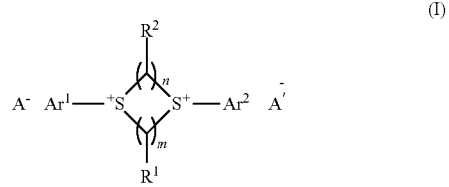

wherein $R^1$ and $R^2$ independently in each occurrence represent a hydrogen atom, a hydroxy group or a C1-C12 hydrocarbon group where a methylene group can be replaced by an oxygen atom or a carbonyl group;

$Ar^1$ and $Ar^2$ each independently represent a C6-C36 aromatic hydrocarbon group which can have a substituent or a C6-C36 heteroaromatic hydrocarbon group which can have a substituent;

$A^-$ and $A'^-$ each independently represent an organic anion; and

"m" and "n" independently each represent an integer of 1 to 2.

2. The salt according to claim 1 where at least one of $A^-$ and $A'^-$ is an anion represented by formula (I-A)

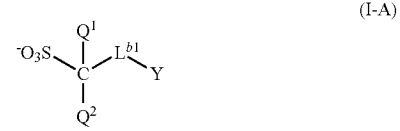

wherein $Q^1$ and $Q^2$ each independently represent a fluorine atom or a C1-C6 perfluoroalkyl group;

$L^{b1}$ represents a C1-C24 divalent saturated hydrocarbon group where a methylene group can be replaced by an oxygen atom or a carbonyl group and where a hydrogen atom can be replaced by a fluorine atom or a hydroxyl group, and Y represents a methyl group or a C3-C18 alicyclic hydrocarbon group where a methylene group can be replaced by an oxygen atom, a carbonyl group or a sulfonyl group and where a hydrogen atom can be replaced by a substituent.

3. An acid generator which comprises the salt according to claim 1.

4. A photoresist composition which comprises the salt according to claim 1 and a resin having an acid-labile group.

5. A process for producing a photoresist pattern comprising the following steps (1) to (5):
   (1) a step of applying the photoresist composition according claim 4 on a substrate,
   (2) a step of forming a composition film by conducting drying,
   (3) a step of exposing the composition film to radiation,
   (4) a step of baking the exposed composition film, and
   (5) a step of developing the baked composition film.

* * * * *